United States Patent

Wuonola et al.

[11] Patent Number: 6,022,983
[45] Date of Patent: Feb. 8, 2000

[54] PYRONIN ANTIBACTERIALS, PROCESS AND NOVEL INTERMEDIATES THERETO

[75] Inventors: Mark A. Wuonola, Waltham; Gary R. Gustafson, Bedford; James S. Panek, Randolph; Tao Hu, Boston; Jennifer V. Schaus, Brookline, all of Mass.

[73] Assignees: Scriptgen Pharmaceuticals, Inc., Waltham; Trustees of Boston University, Boston, both of Mass.

[21] Appl. No.: 09/002,541

[22] Filed: Jan. 2, 1998

Related U.S. Application Data

[63] Continuation-in-part of application No. 08/822,323, Mar. 21, 1997.

[60] Provisional application No. 60/013,874, Mar. 22, 1996.

[51] Int. Cl.[7] .......................... C07C 33/03; C07C 45/26; C07C 67/30; C07D 309/32

[52] U.S. Cl. ..................... 549/291; 549/292; 549/356; 560/211; 568/449; 568/840; 568/909.5

[58] Field of Search ..................... 549/291, 292, 549/356; 568/449, 840, 909.5; 560/211

[56] References Cited

PUBLICATIONS

Kohl et al., Die Biosynthase des Antibiotikume Myxopyronin A aus *Myxococcus fulvus* Stamm Mx f50, Liebigs Ann. Chem. 1984 1088–1093.
Jansen et al., Chemical Abstract, 103:3291, 1985.
Jarolim et al., Chemical Abstract, 85:123296, 1976.
Kohl et al., Chemical Abstract, 101:87146, 1984.
Sharma et al., Chemical Abstract, 99:38646, 1982.

*Primary Examiner*—Johann Richter
*Assistant Examiner*—Taofiq A. Solola
*Attorney, Agent, or Firm*—Darby & Darby

[57] ABSTRACT

The present invention provides convergent processes for preparing myxopyronins and corallopyronins, compounds useful as antibacterial therapeutics. The present invention also provides novel compositions of matter which are useful for the preparation of pyronin antibiotics.

15 Claims, 25 Drawing Sheets

R = H, CH3 or CN

SEMCl, DIPEA
CH₂Cl₂
→
92% yield

A ———————————— A

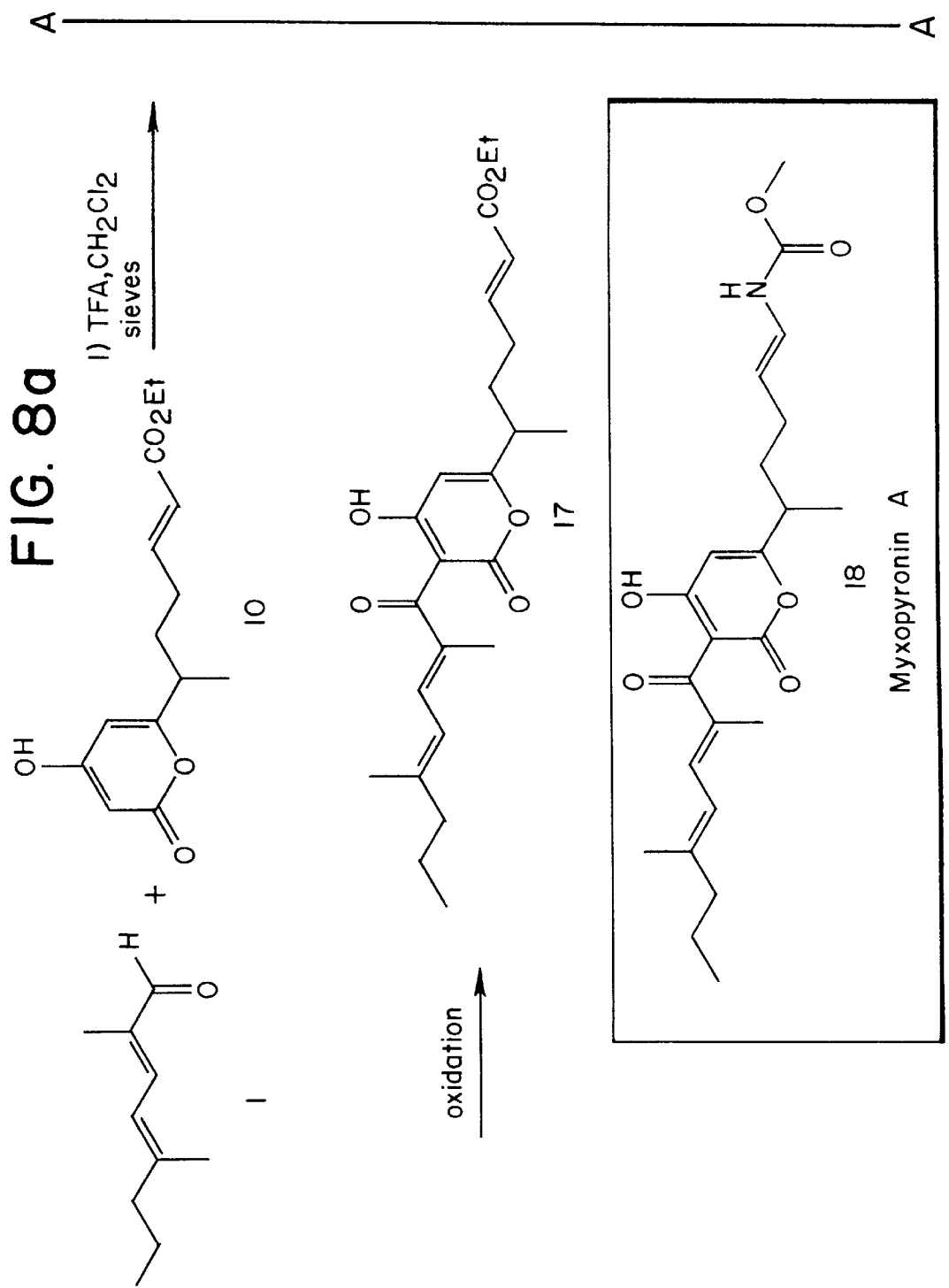

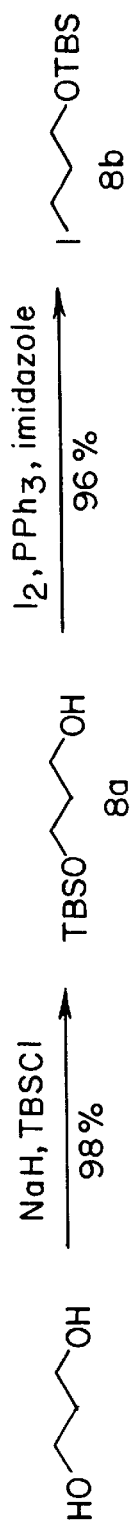
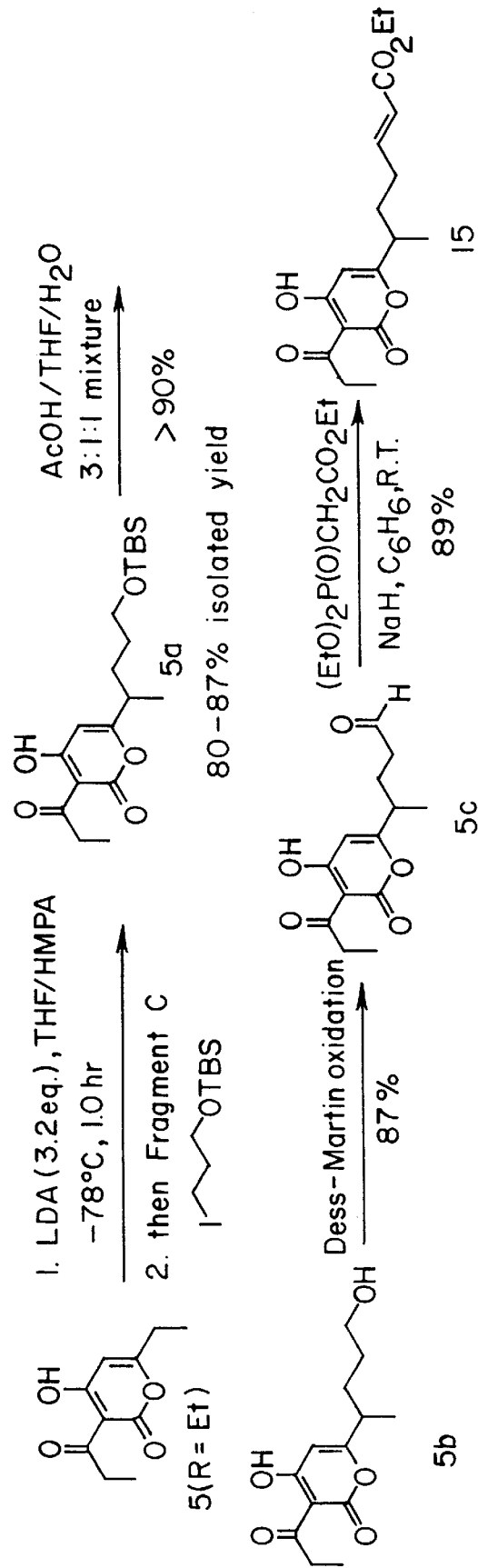
FIG. 12c
FIG. 13a

PYRONIN ANTIBACTERIALS, PROCESS AND NOVEL INTERMEDIATES THERETO

This application is a continuation-in-part of U.S. Ser. No. 08/822,323, filed Mar. 21, 1997, which is based on U.S. Provisional Application Serial No. 60/013,874, filed Mar. 22, 1996, the contents of which are hereby incorporated by reference into this application.

FIELD OF THE INVENTION

The present invention is in the field of pyronin antibiotics. In particular, the present invention relates to processes for the preparation of myxopyronins and corallopyronins, compounds useful as antibacterial therapeutics. The present invention also provides novel compositions of matter which are useful as intermediates for preparing the pyronin antibiotics.

Throughout this application, various publications are referred to, each of which is hereby incorporated by reference in its entirety into this application to more fully describe the state of the art to which the invention pertains.

BACKGROUND OF THE INVENTION

Myxopyronins and corallopyronins are 2-pyrone-containing antibiotics which present a significant opportunity in antibacterial therapy. They constitute a synthetically accessible, unexploited series of low molecular weight bacterial RNA polymerase (RNAP) inhibitors with favorable properties: selectivity vs. human RNAP, cell penetration (minimal inhibitory concentrations (MICs) at concentrations comparable to in vitro bacterial RNAP $IC_{50}S$), and potency against rifampicin-resistant *S. aureus* equal to that against a rifampicin-susceptible strain.

Corallopyronin A/B and myxopyronin A/B are natural products isolated from gliding bacteria (*Corallococcus coralloides; Myxococcus fulvus*) and discovered to be RNAP inhibitors. Reichenbach, H., et al., *Liebigs Ann. Chem.*, 1983, 1656; Reichenbach, H., et al., *Liebigs Ann. Chem.*, 1984, 1088; Reichenbach, H., et al., *Liebigs Ann. Chem.*, 1985, 822. The structures of these compounds are closely related having in common a 3-acyl4-hydroxy-2-pyrone with an alkyl chain at the 6-position bearing a vinyl carbamate functionality, a feature atypical of natural products. They differ only in the substitution on the alkyl chain attached to the 3-position of the pyrone, the corallopyronins being more elaborate (FIG. 1 (*a*)). The pyronins have good intrinsic activity in antibacterial assays against both *E. coli* and *S. aureus* RNA polymerase. This activity is specific with respect to human or SP6 polymerases. MIC data (see Table I) show that these compounds, like rifampicin, are not absorbed well by *E. coli* but that they have intrinsic activity against both gram positive and gram negative bacteria.

An attractive feature of this series of compounds is their activity against strains resistant to rifampicin. The MIC for rifampicin is ca. 10 nM against susceptible strains, but falls off against resistant strains (MIC>10 $\mu$M). The use of rifampicin is limited by the development of bacterial resistance. Both myxo- and corallopyronins are equiactive against Rif-susceptible and Rif-resistant *S. aureus*.

Pyrones have been used in the prior art to elicit a biological effect in a few instances, but in none of these instances have they been used as an antibacterial agent. 2H-Pyran-2,6(3H)-dione derivatives are reported to be active at reasonable doses in a passive cutaneous anaphylaxis model in rats when administered by either the intravenous or oral route. Snader, K. M. et al., *J. Med. Chem.*, 1979, 22, 706; Chahrin, L. W., Snader, K. M., Williams, C. R., 2H-Pyran-2,6(3H)-dionederivate. German Patent 25 33 843. In a second case, simple 3-(1-oxoalkyl)-4-hydroxy-6-alkyl-2-pyrones were found to be effective in vitro in the inhibition of human sputum elastase. Cook, L., Ternai, B., Ghosh, P., *J. Med. Chem.*, 1987, 30, 1017. Lastly, a series of pyrone derivatives were found to be effective inhibitors of HIV protease in both enzymatic assays and cell culture (FIG. 1 (*b*)). Skulnick, H. I., et al., *J. Med. Chem.*, 1995, 38, 4968. No synthetic investigations or medicinal uses of pyronin antibacterials have been reported in the literature.

The present invention provides novel intermediates useful in the synthesis of myxopyronins A and B and derivatives thereof. In addition, the present invention provides processes for synthesizing myxopyronins A and B and derivatives thereof as well as corallopyronins. The myxopyronins of the invention are useful against gram negative and positive bacteria.

SUMMARY OF THE INVETNION

One object of the present invention is to provide processes for the preparation of myxopyronins and corallopyronins, compounds useful as antibacterial therapeutics. In particular, the present invention provides myxopyronins A and B.

Another object of the present invention is to provide various compositions of matter useful as intermediates in the preparation of the antibiotic myxopyronin.

A further object of the present invention is to provide methods of preparing such intermediates.

BRIEF DESCRIPTION OF THE DRAWINGS

FIG. 1(*b*) illustrates coumarin derivatives which inhibit HIV protease in enzymatic assays and cell culture. Skulnick, H. I., et al., *J. Med. Chem.*, 1995, 38, 4968.

TABLE 1

| | In Vitro $IC_{50}$ ($\mu$M) | | | | MIC ($\mu$g/ml) | | | |
|---|---|---|---|---|---|---|---|---|
| | *E. coli* | *S. aureus* | Human | | SP6 | | *E. coli* | *E. coli* |
| Compound | RNAP | RNAP | RNAP | RNAP | Rev/RRE | *S. aureus* | MCR | BAS |
| Myxopyronin A/B | 10 | 10 | >200 | >200 | 100 | 4 | 180 | 1.6 |
| Corallopyronin A/B | 6 | 10 | >200 | >200 | 100 | 4 | >200 | 0.4 |

Figure 3:
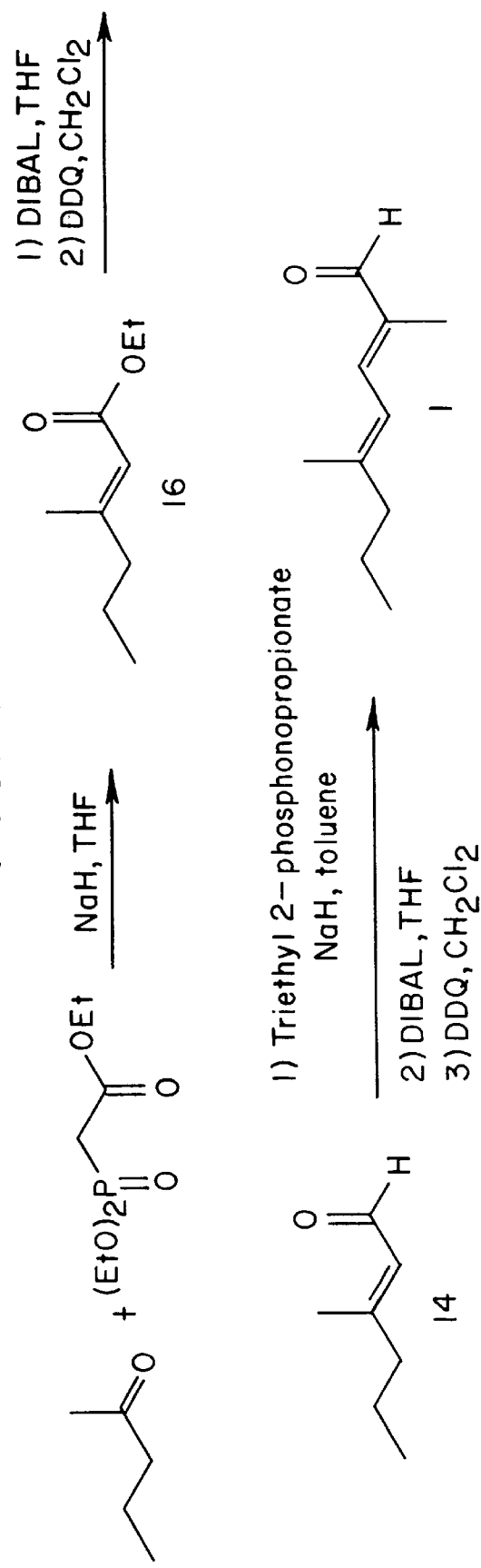

FIG. 3 illustrates the synthesis of compound 1 in accord with the present invention. (The natural products have been illustrated with the natural occurring (R)-configuration, however all materials in this paper were synthesized in racemic form.)

Figure 4:
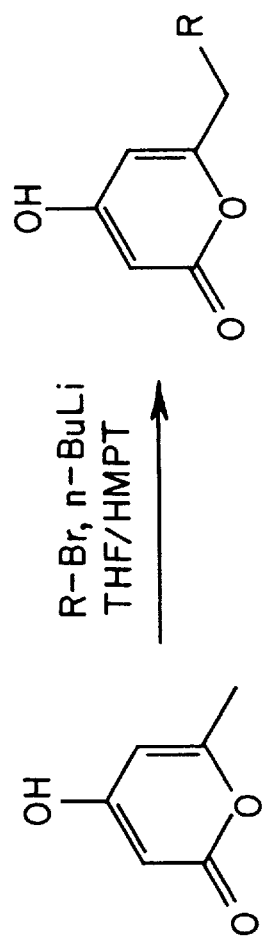

FIG. 4 illustrates alkylation of the 7-position of compound 3 for the preparation of compound 10.

Figure 5:
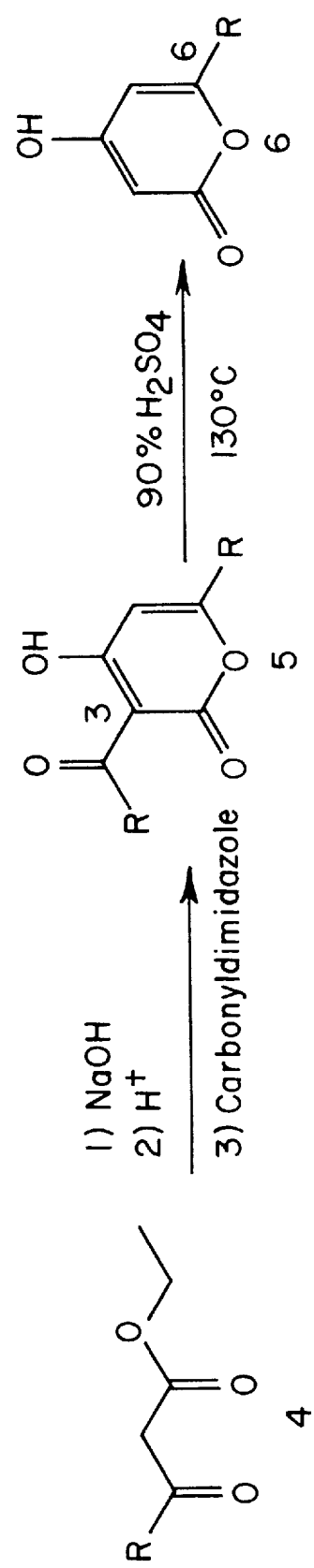

FIG. 5 illustrates the synthesis of compound 6 in accord with the present invention.

Figure 6A:
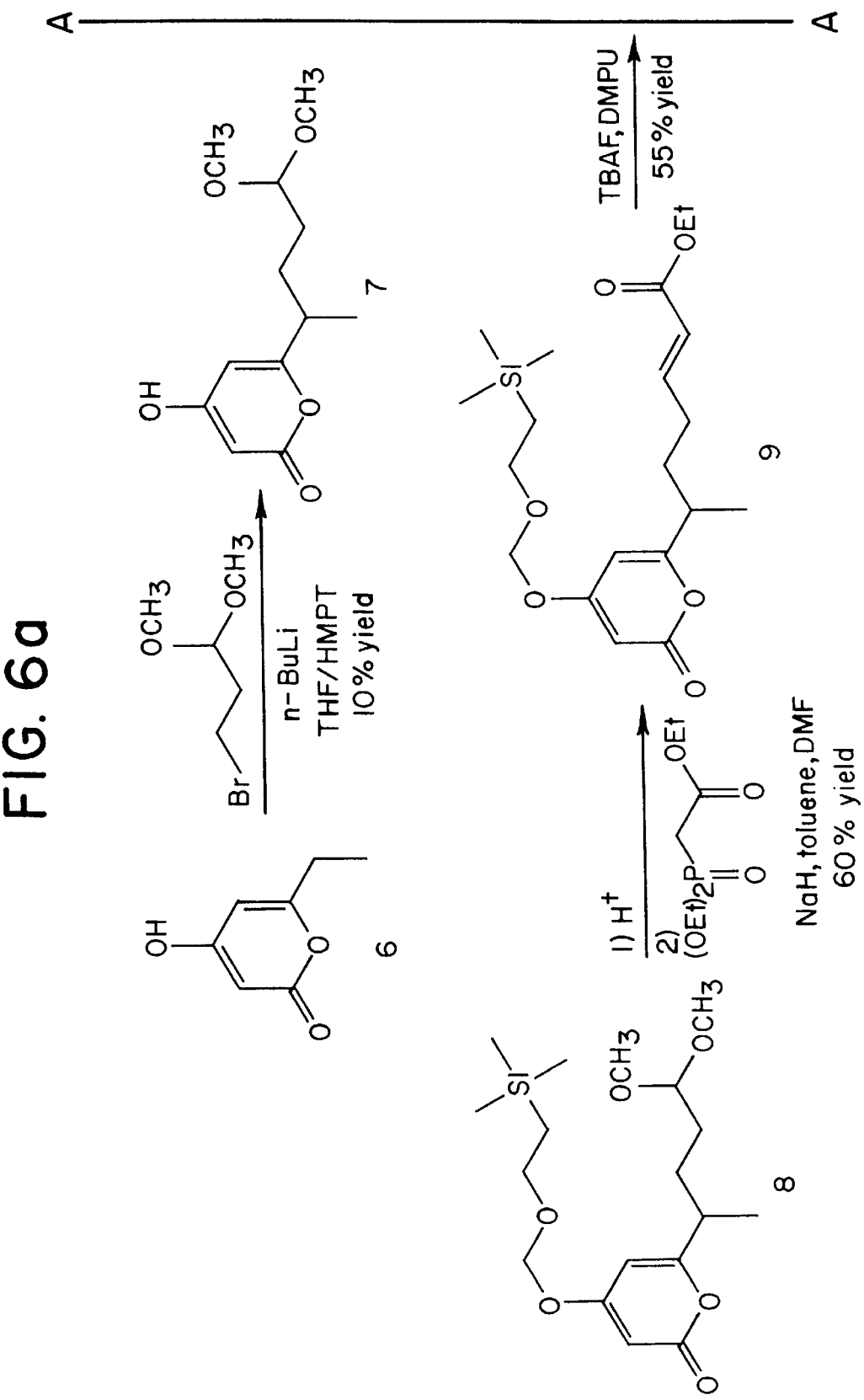
Figure 6B:
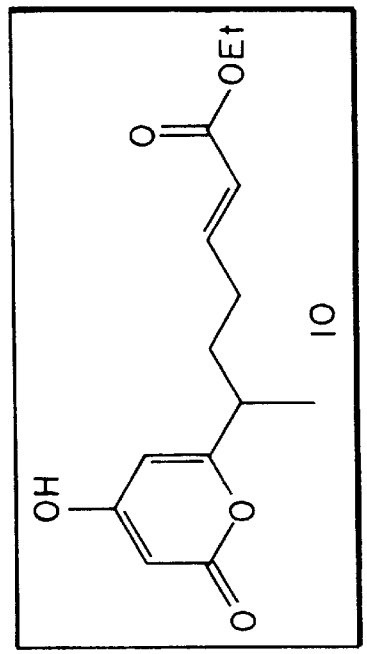

FIG. 6 illustrates the synthesis of compound 10 in accord with the present invention.

Figure 7:
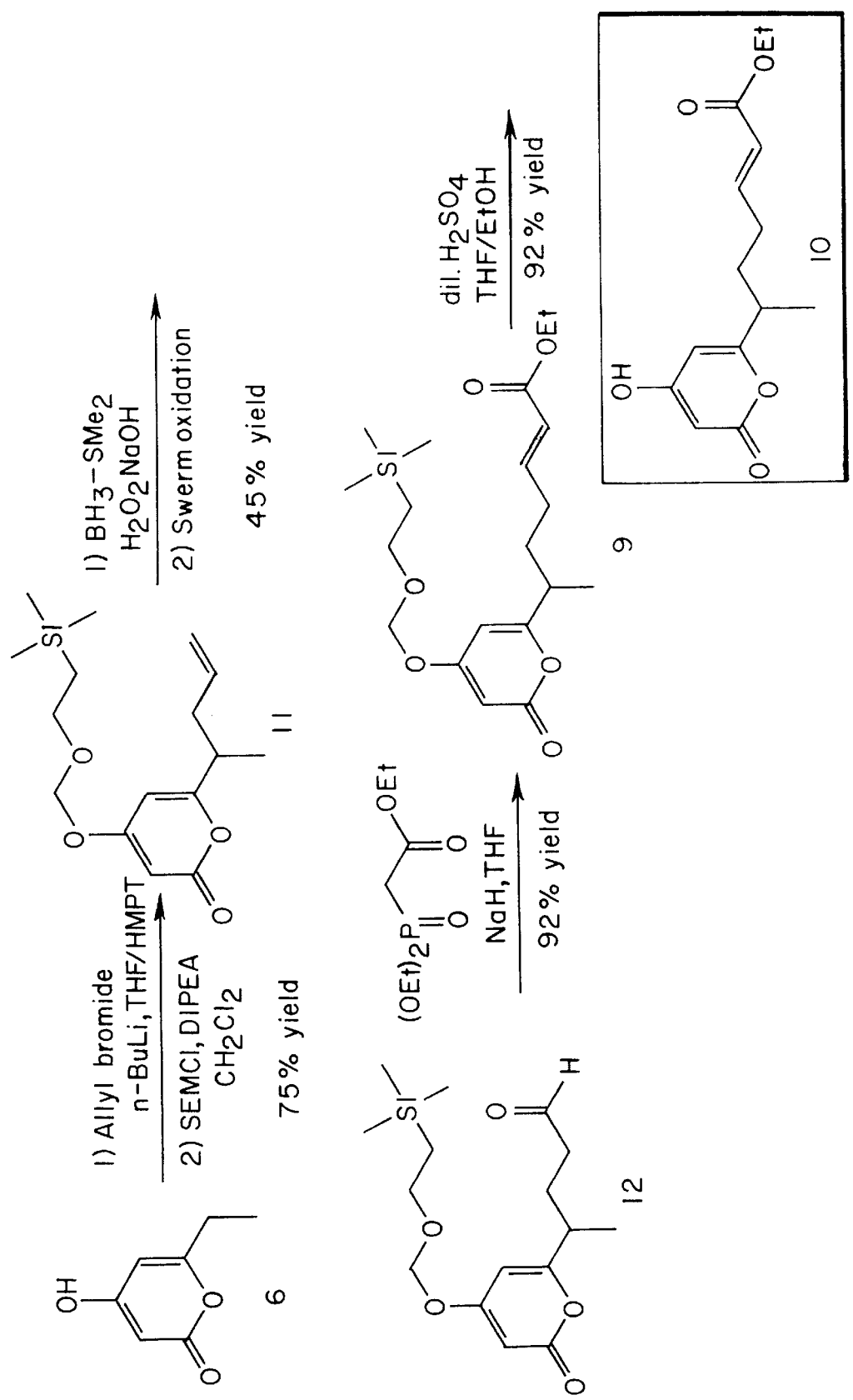

FIG. 7 illustrates an alternative synthesis of compound 10 in accord with the present invention.

Figure 8B:
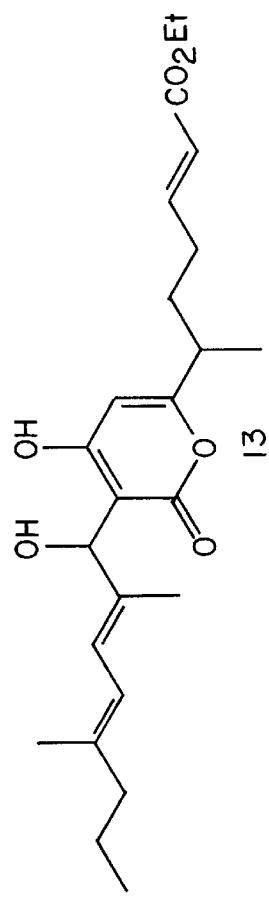

FIG. 8 illustrates the synthesis of compound 18 in accord with the present invention.

Figure 9:
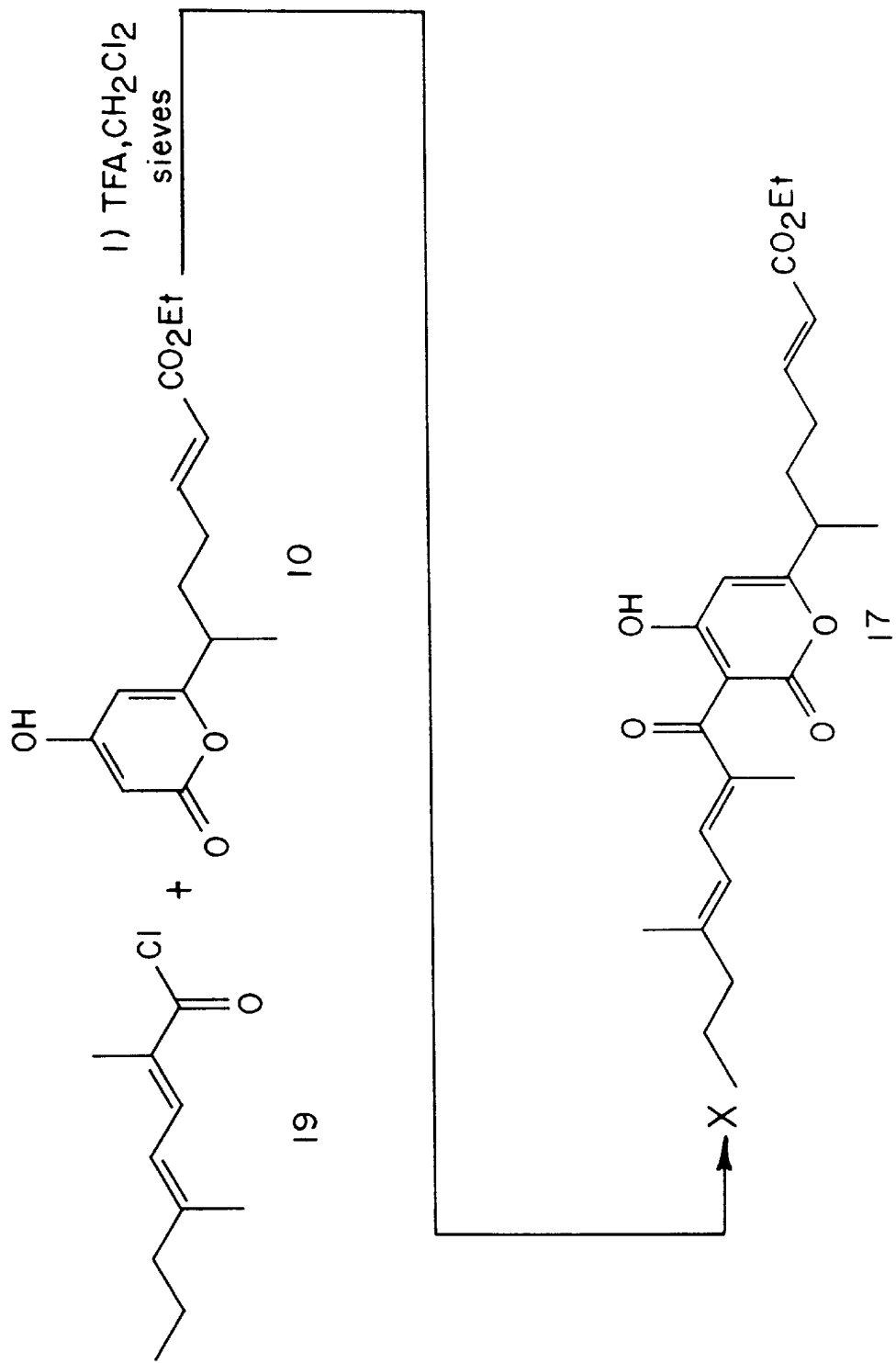

FIG. 9 illustrates the attempted acylation of pyrone 10 with acyl chloride 19.

Figure 10A:
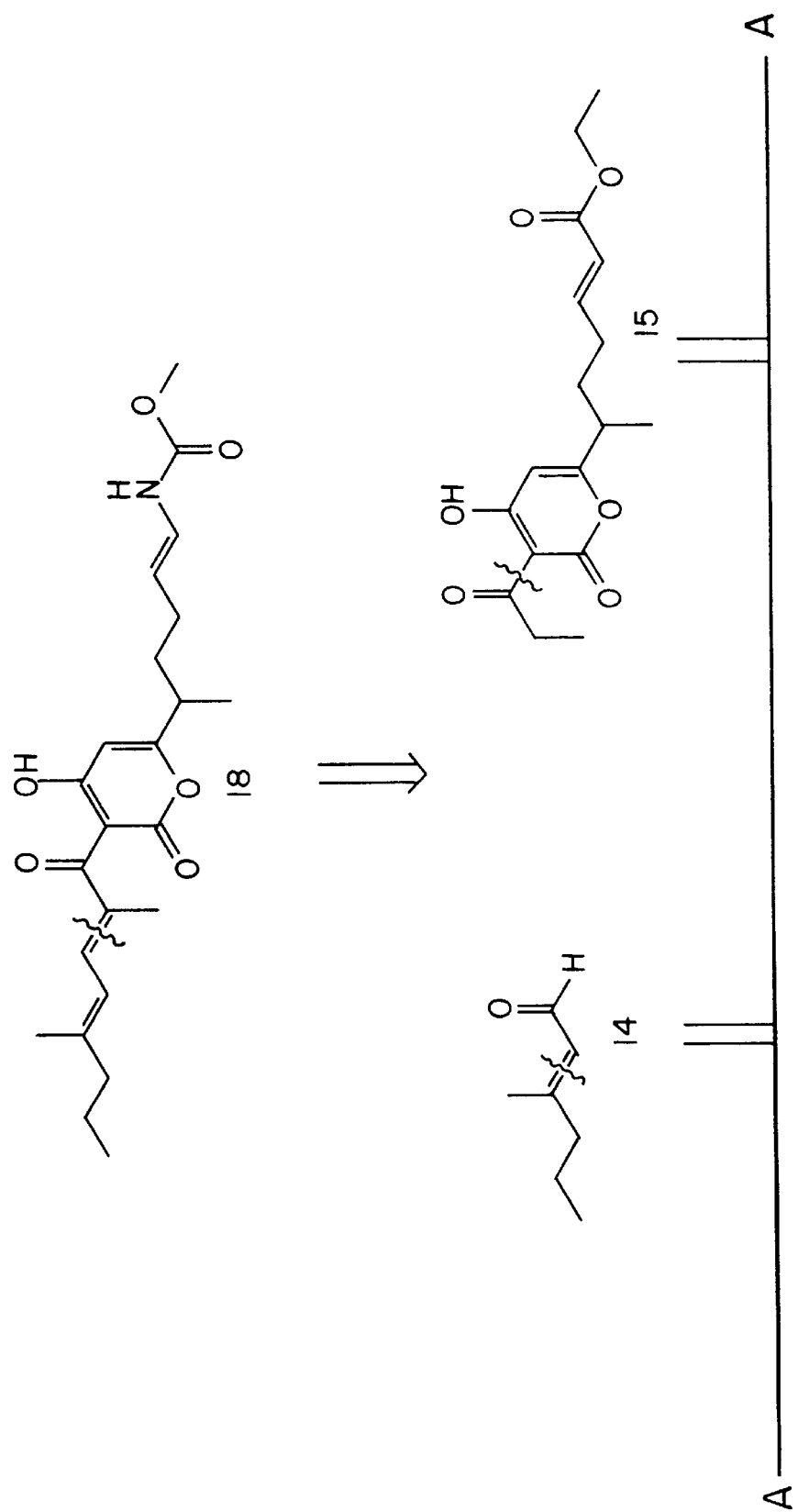
Figure 10B:
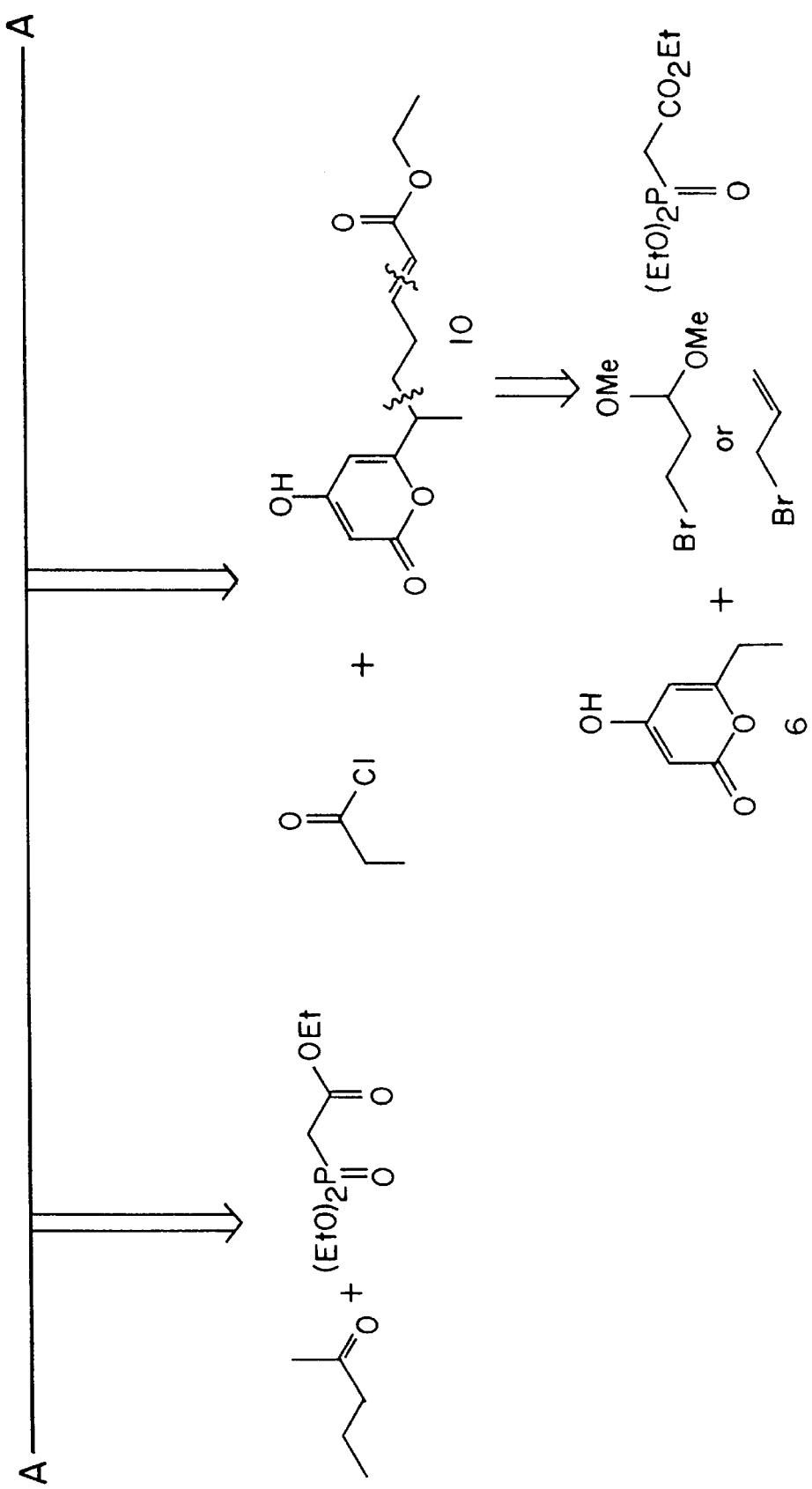

FIG. 10 illustrates an alternative retrosynthetic analysis for the preparation of myxopyronin A.

Figure 11A:
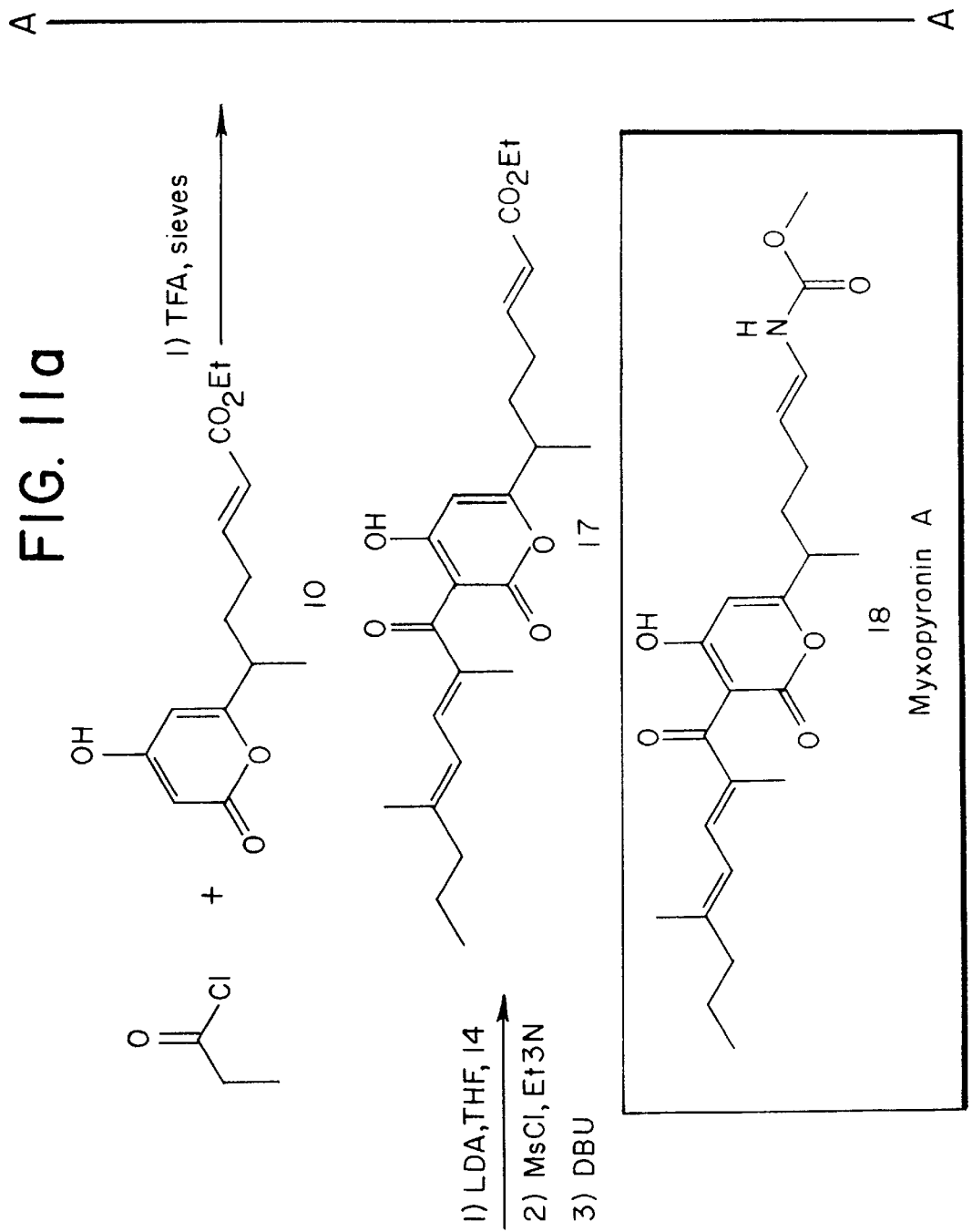
Figure 11B:
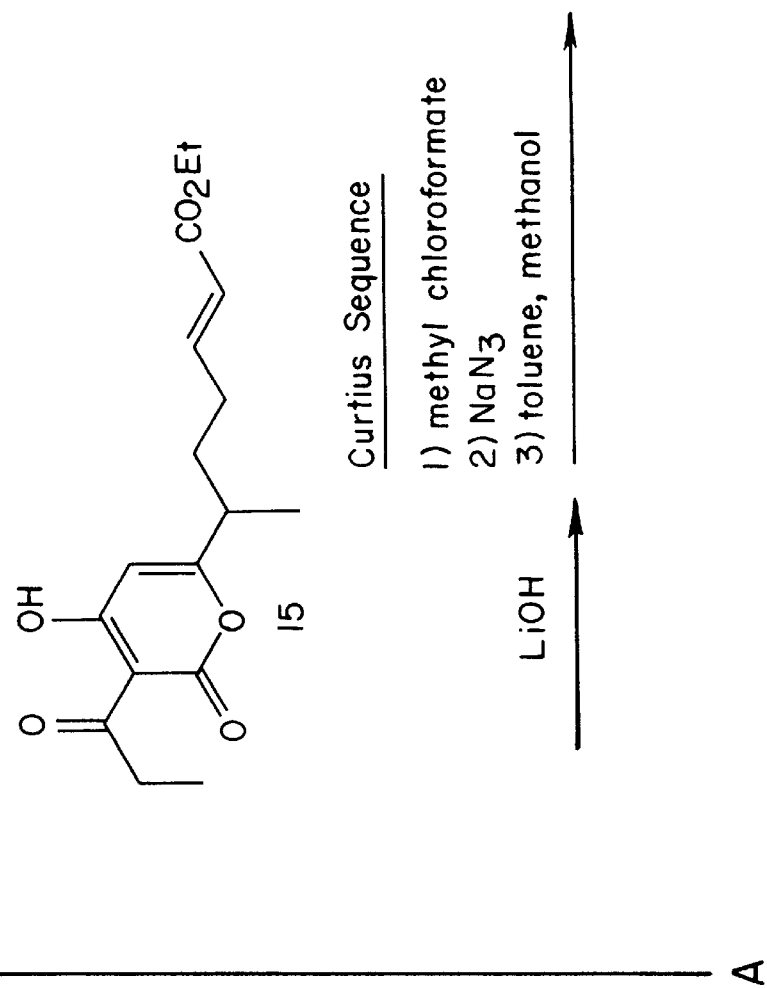

FIG. 11 illustrates the acylation of pyrone 10 with propionyl chloride and subsequent elaboration to myxopyronin A.

Figure 12:
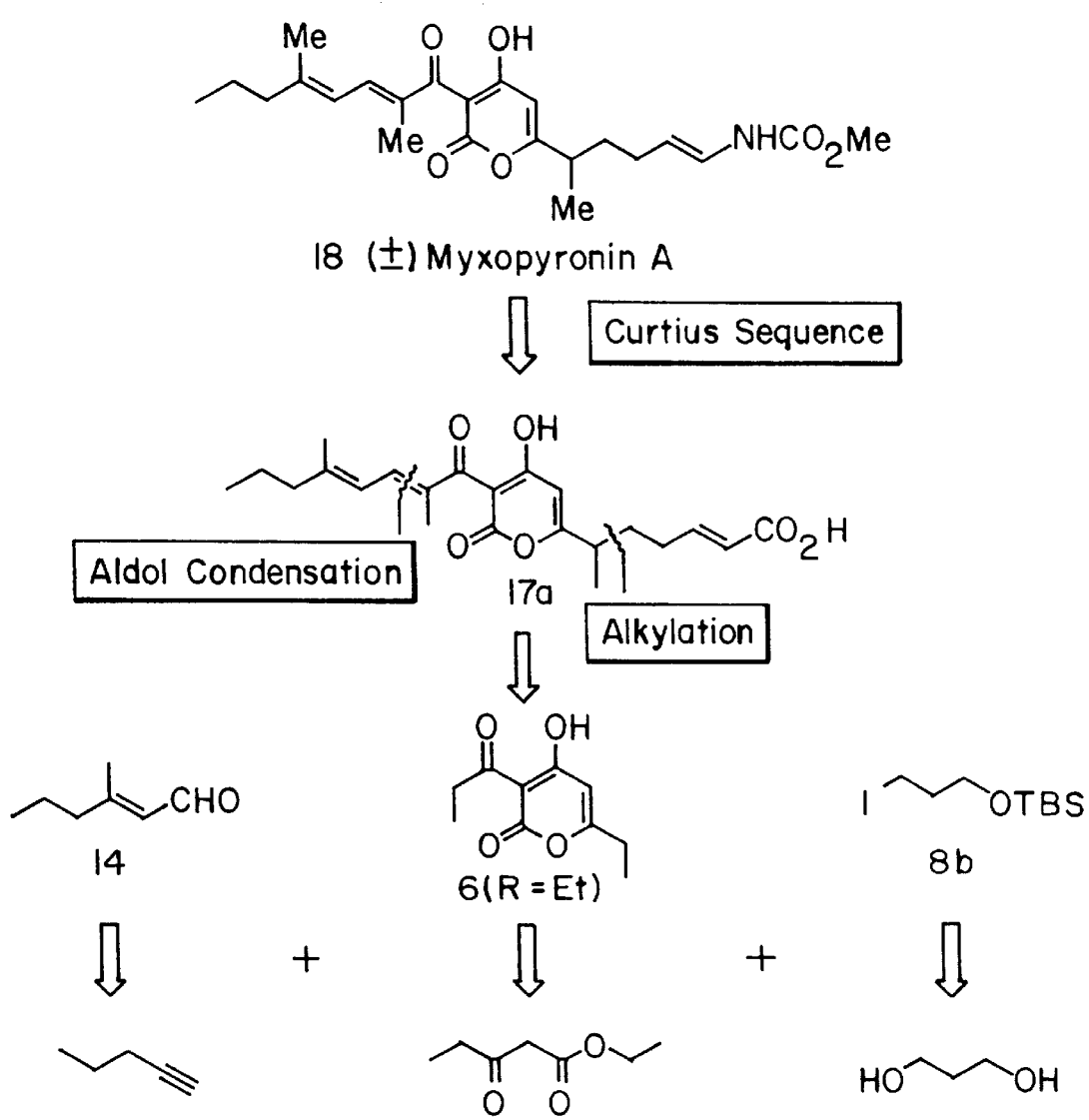

FIG. 12 shows a retrosynthetic analysis of myxopyronin A.

Figure 12A:
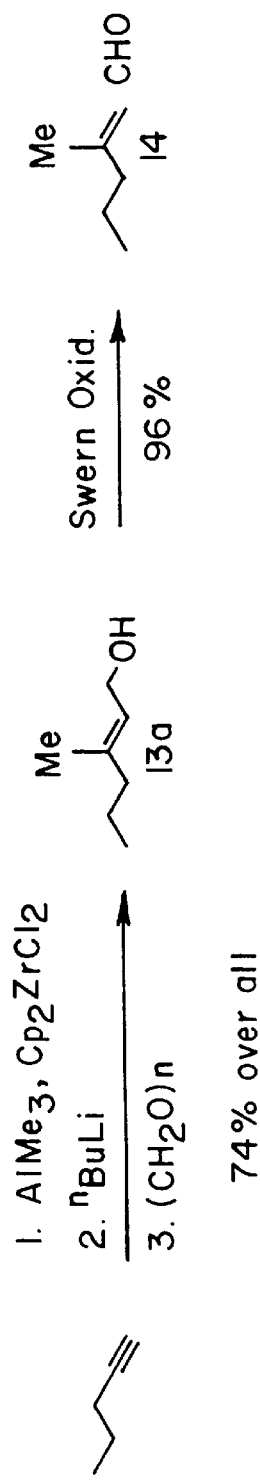

FIG. 12(a) shows the preparation of allyl aldehyde 14.

Figure 12B:
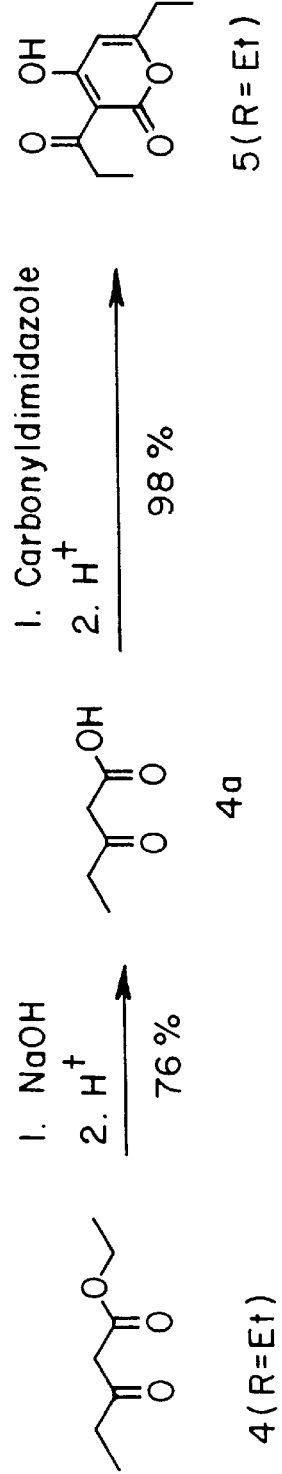

FIG. 12(b) shows the preparation of acylated pyrone 5.

FIG. 12(c) shows the preparation of iodide 8b.

FIG. 13(a) provides a synthetic route to acyl pyrone intermediate 15.

Figure 13B:
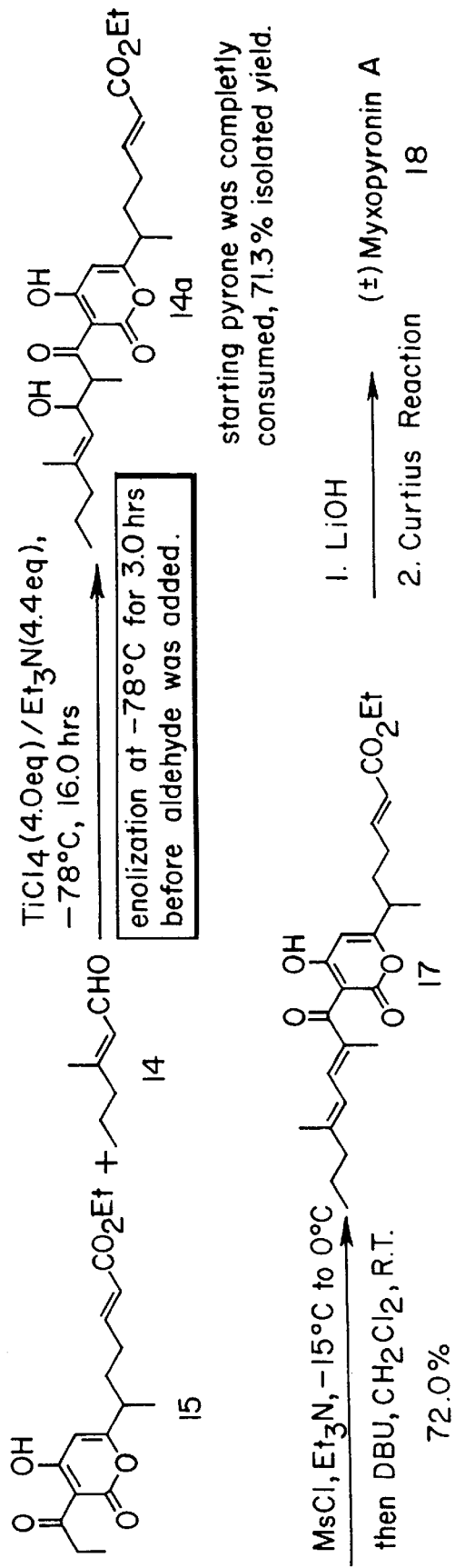

FIG. 13(b) illustrates the condensation reaction of intermediates 14 and 15 and subsequent elaboration to myxopyronin A.

Figure 14:
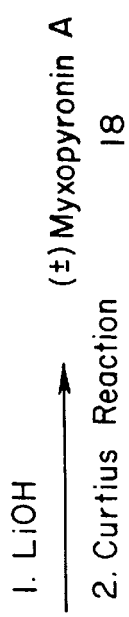

FIG. 14 shows the preparation of allyl aldehyde 14.

Figure 15:
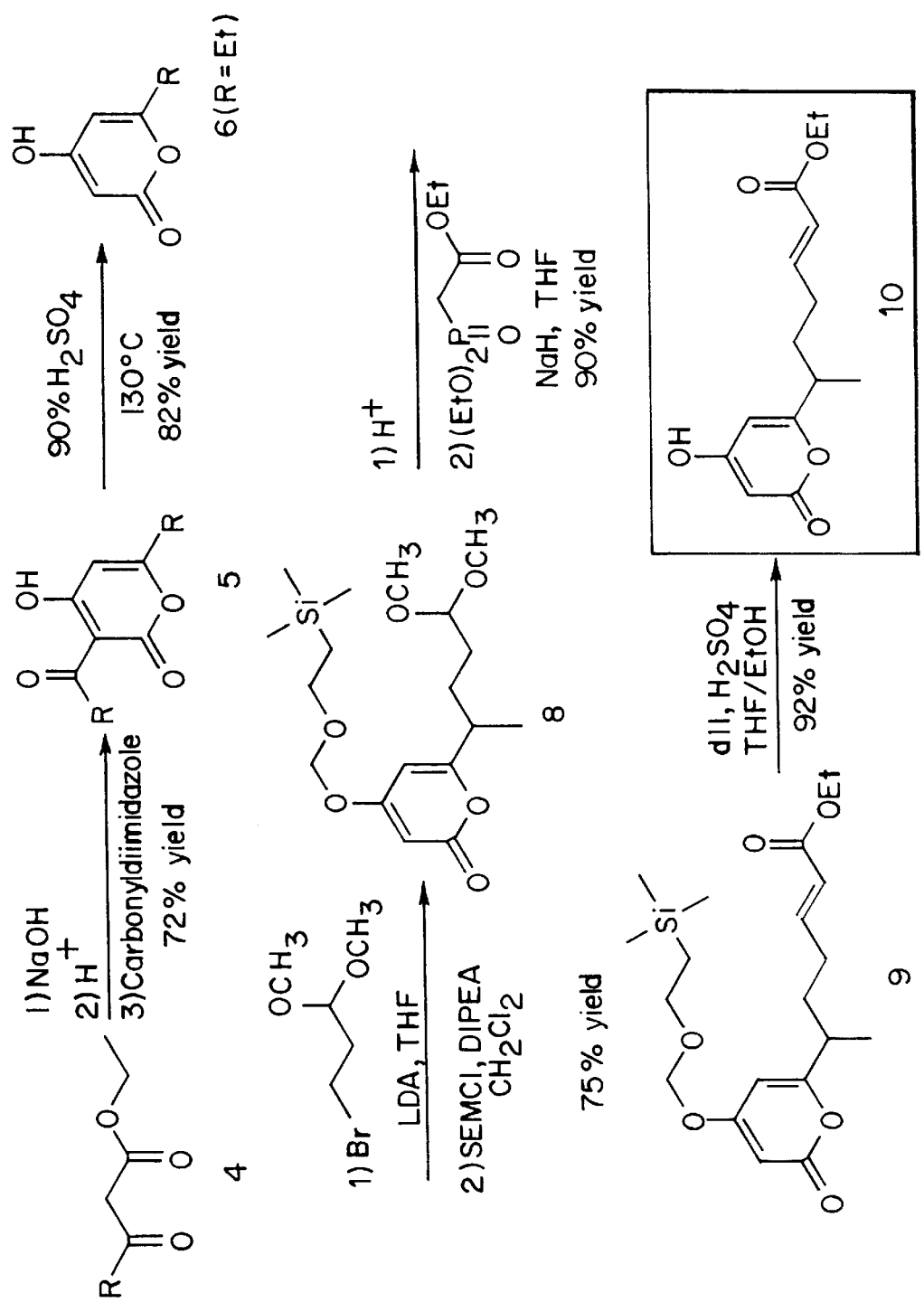

FIG. 15 provides a synthetic route to intermediate pyrone 10.

Figure 16:
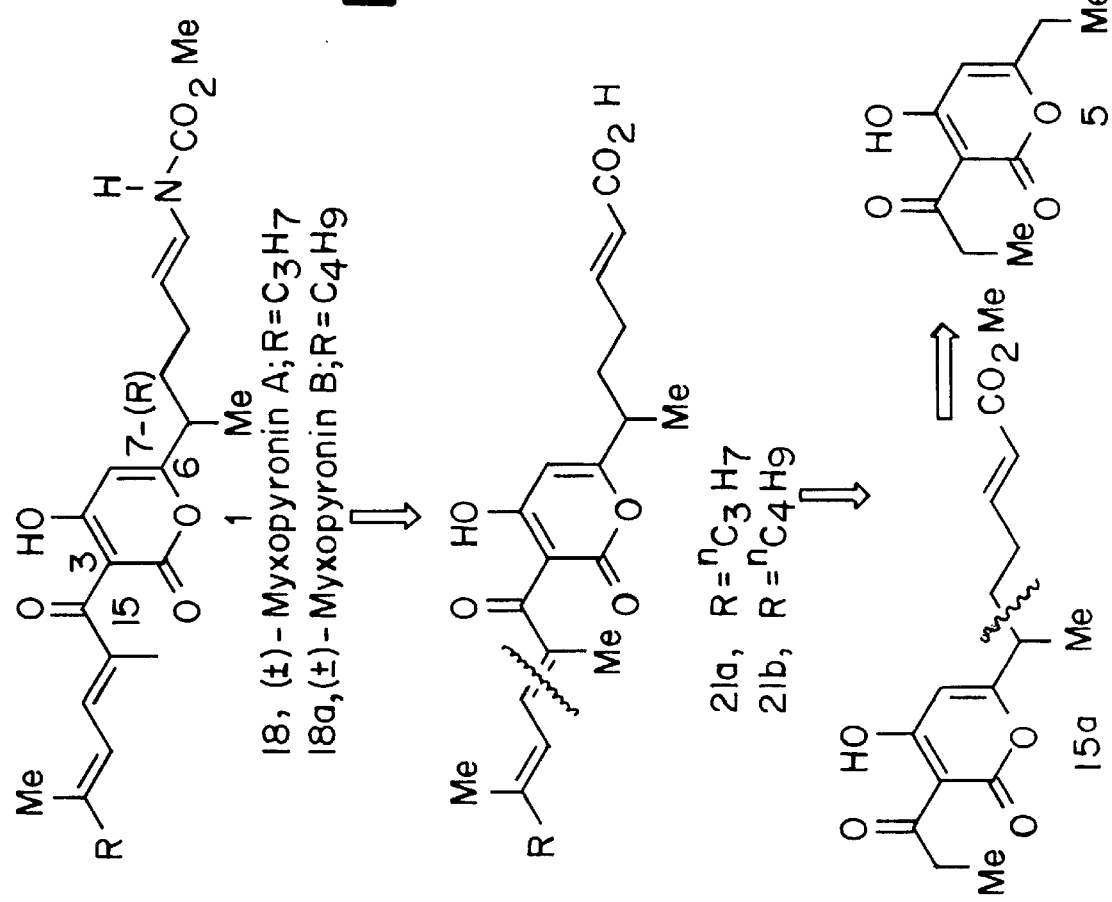

FIG. 16 illustrates a retrosynthetic analysis of myxopyronin A and B.

Figure 17:
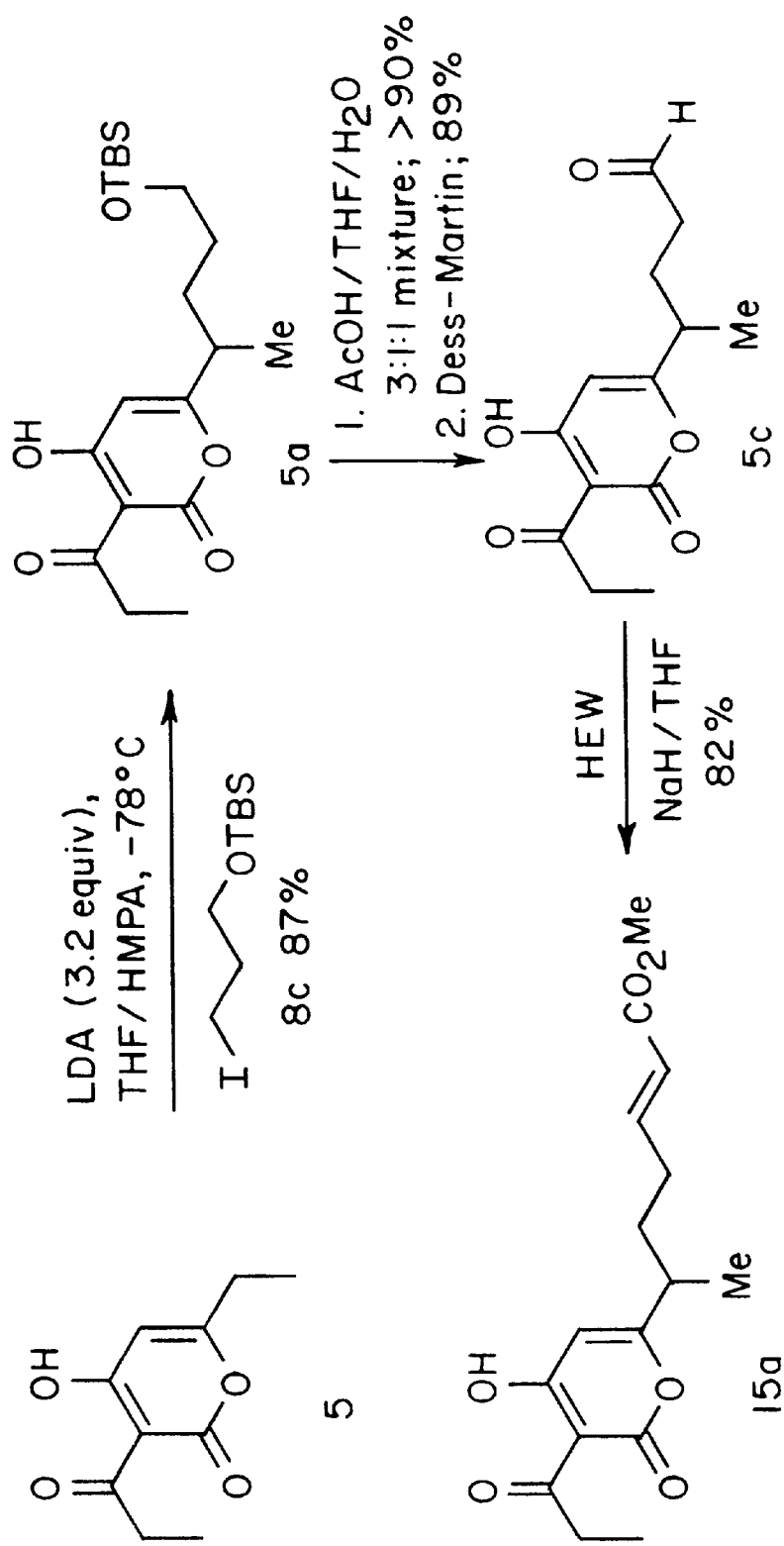

FIG. 17 provides a synthetic route to compound 15a.

Figure 18:
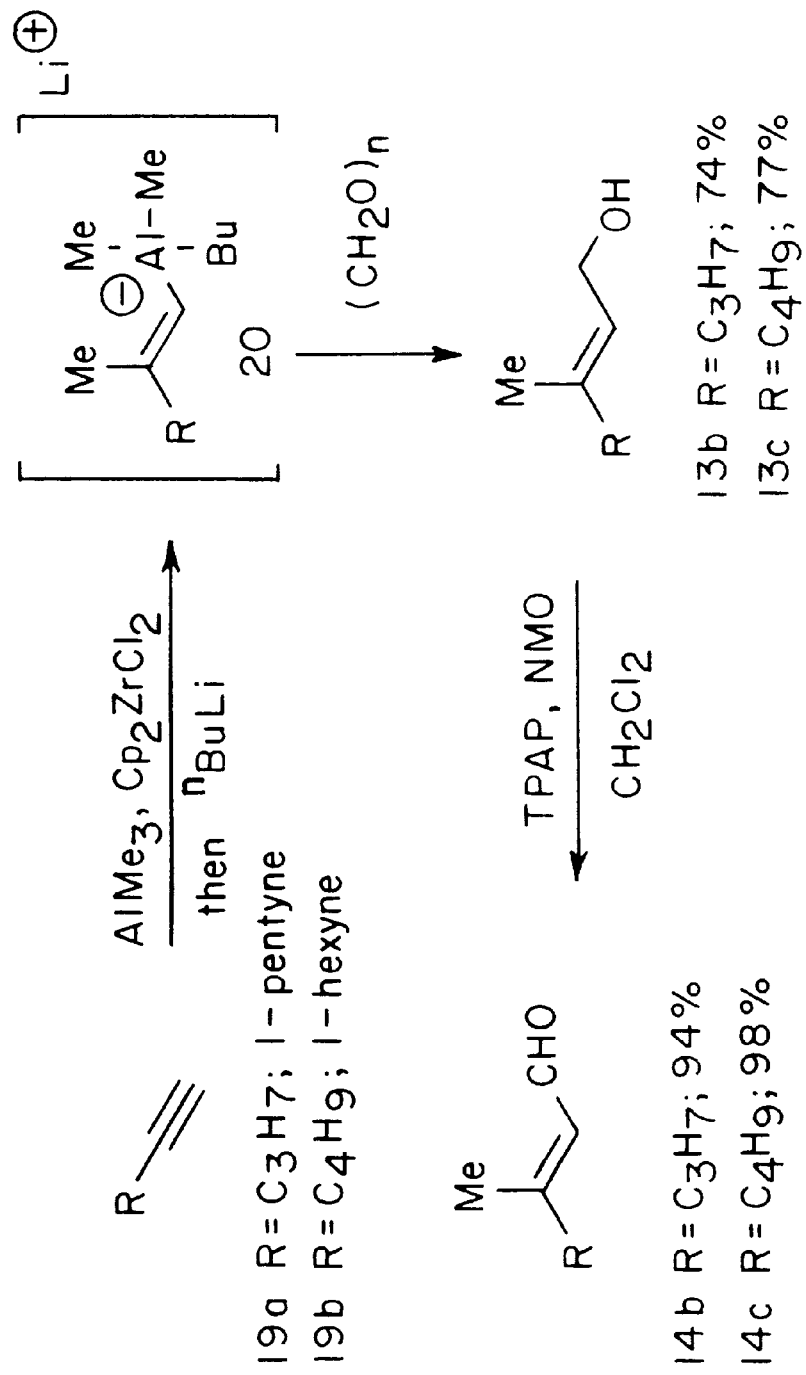

FIG. 18 shows a method for preparing α,β-unsaturated aldehydes useful as intermediates in the synthesis of myxopyronins.

Figure 19:
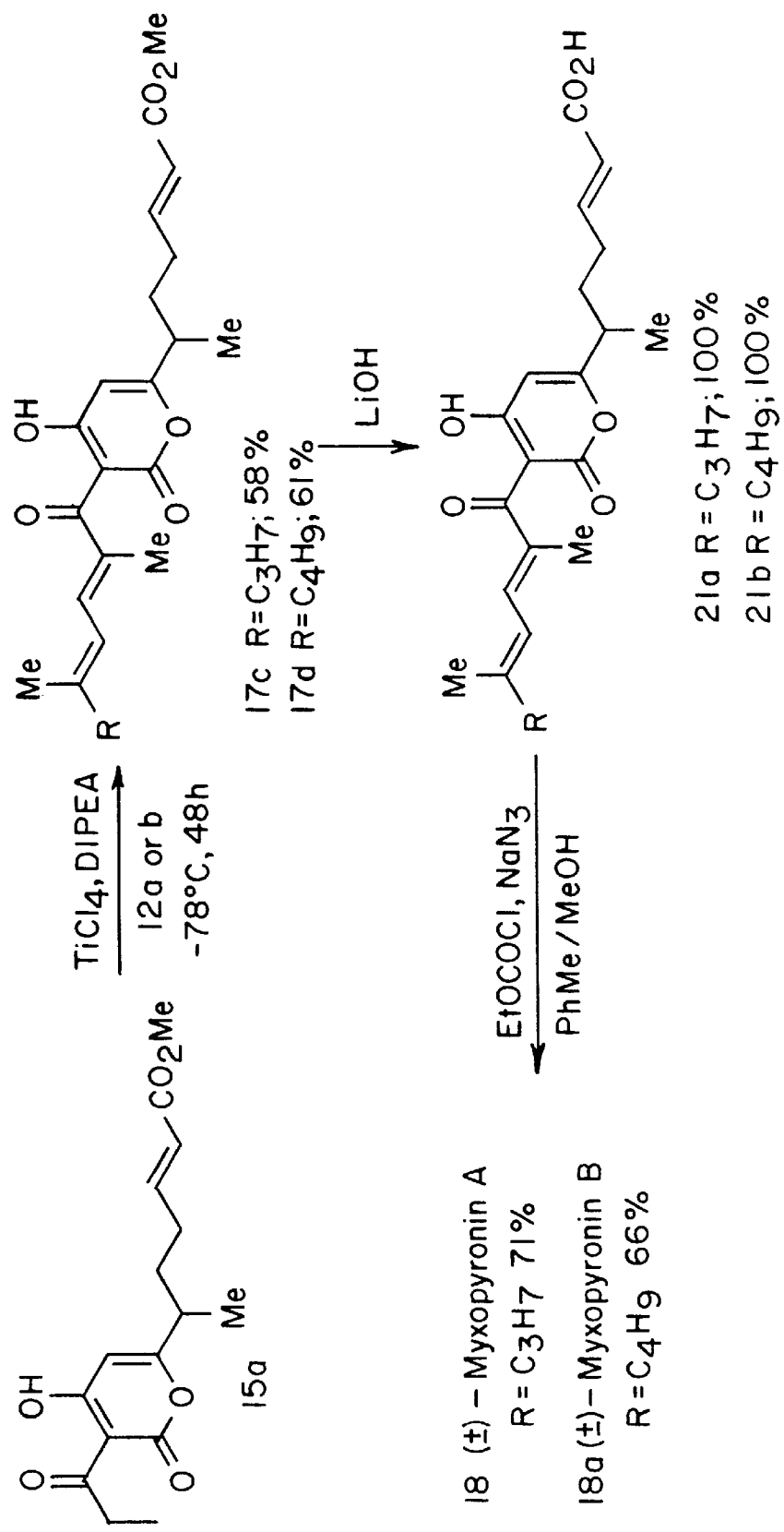

FIG. 19 shows a synthetic route to myxopyronin A and B starting from intermediate 15a.

Figure 20A:
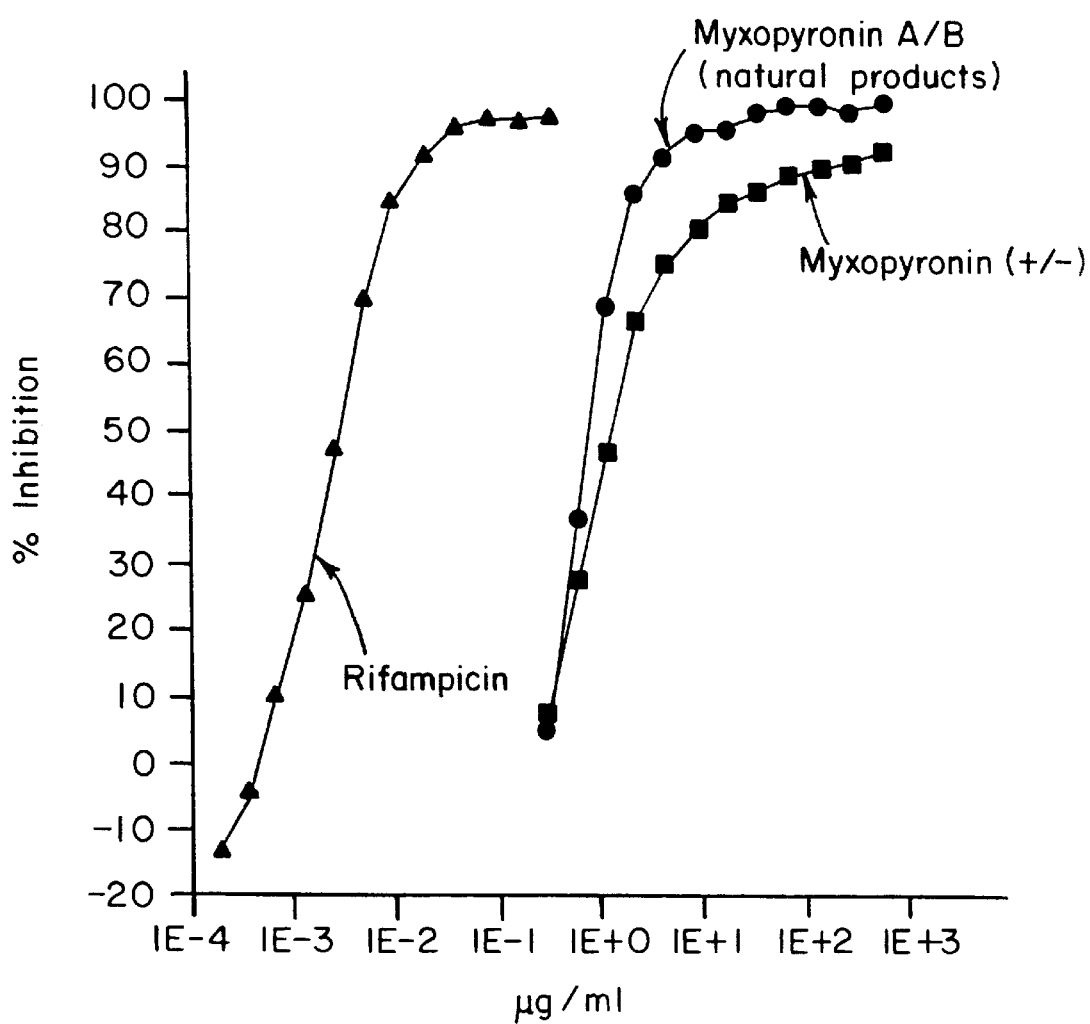

FIG. 20(a) provides a graphical representation of the inhibitory effect as a function of 2 0 concentration of a mixture of isolated natural myxopyronins A and B, compared with synthetic racemic myxopyronin A and rifampicin, in an in vitro transcription assay using *E. coli* RNA polymerase.

Figure 20B:
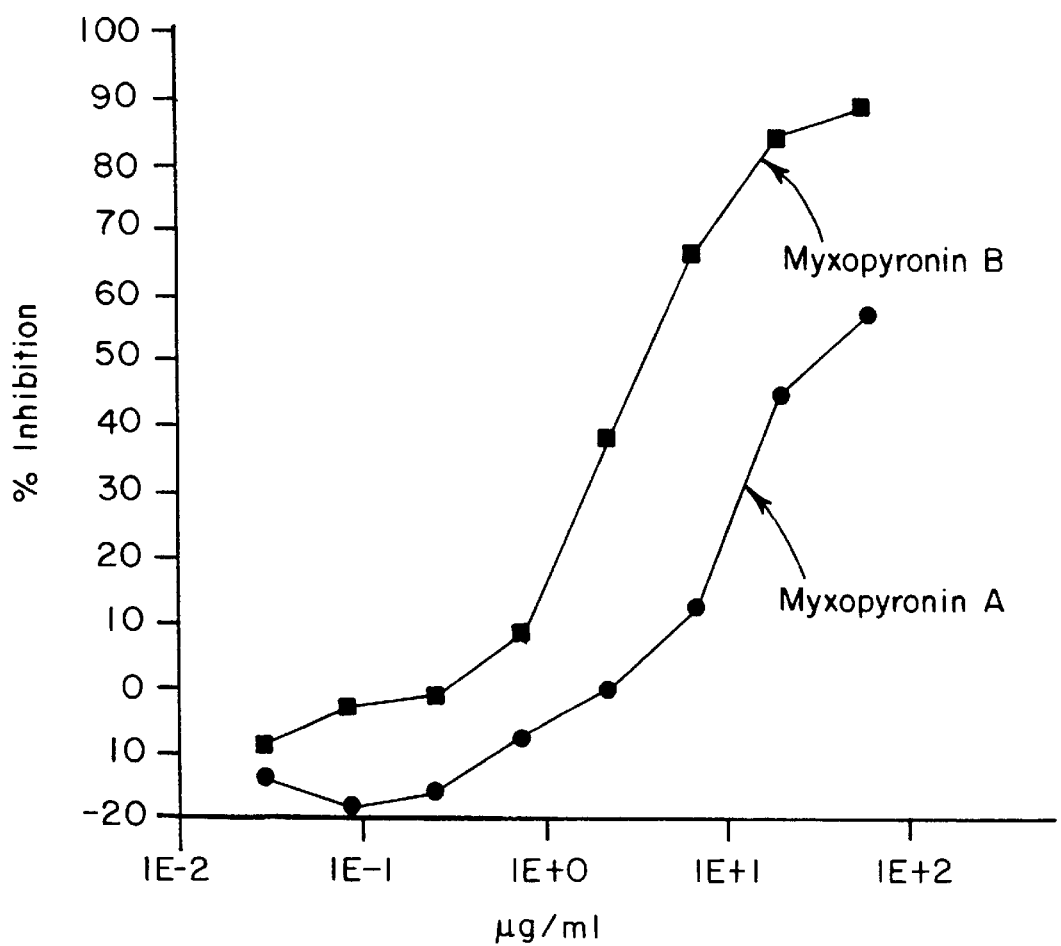

FIG. 20(b) provides a graphical representation of the inhibitory effect as a function of concentration of synthetic myxopyronins A and B in an in vitro transcription assay using *E. coli* RNA polymerase.

DETAILED DESCRIPTION OF THE INVENTION

Figure 1A:
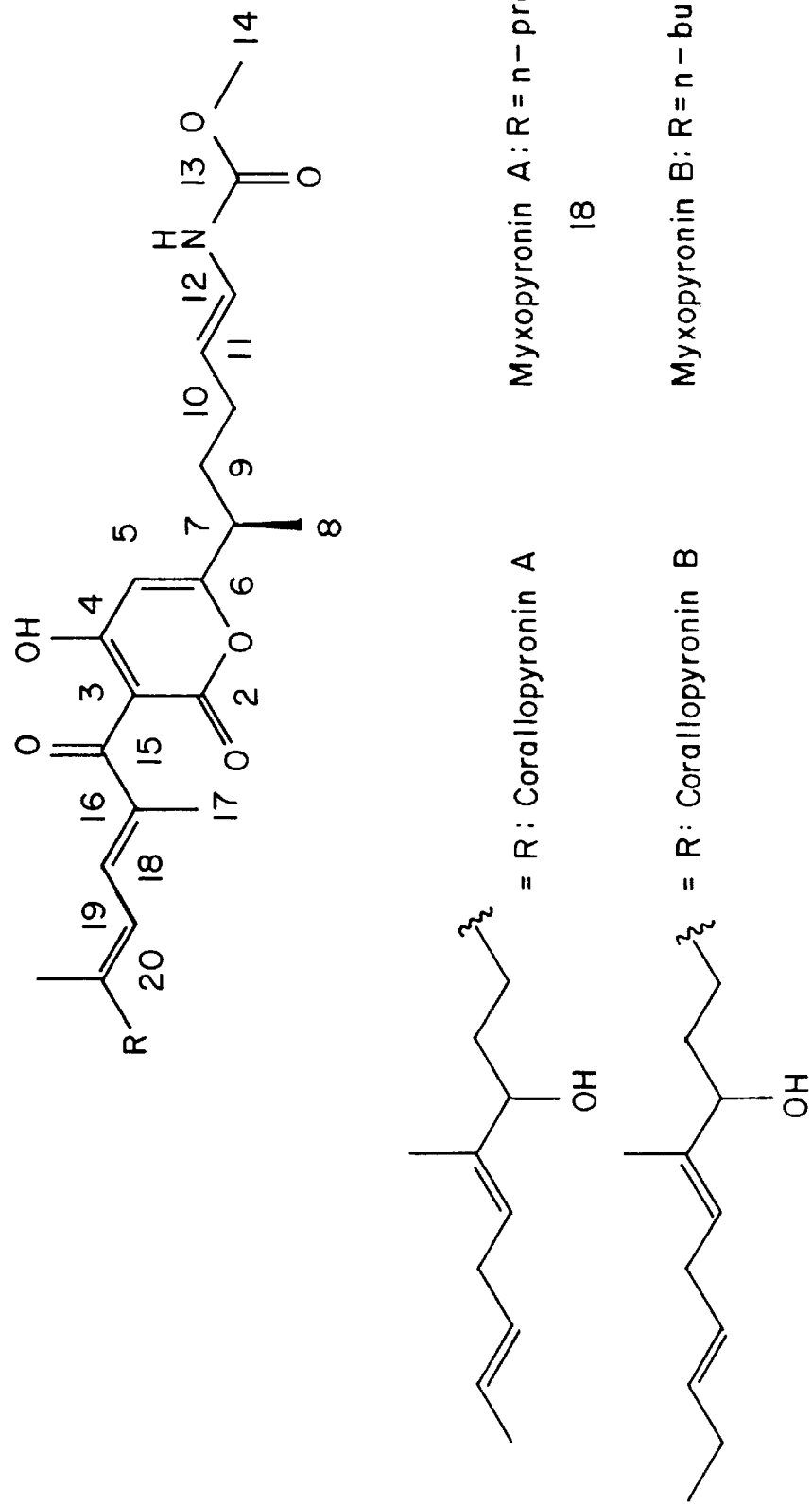
FIG. 1(*a*) shows the structures of corallopyronin A/B and myxopyronin A/B.
Figure 1B:
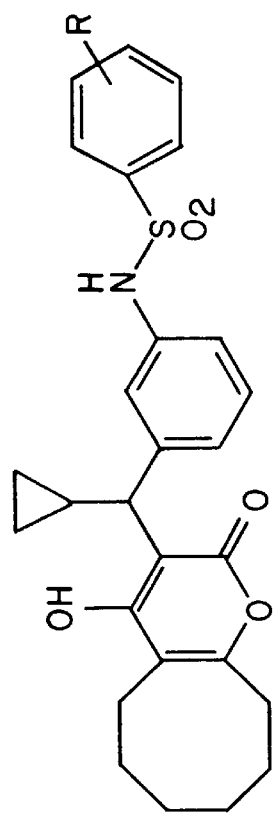

The present invention provides a convergent synthetic route to prepare myxopyronin compounds, including myxopyronins A and B (FIG. 1). The invention provides two variant pathways based on alternative approaches to install the side chain at the pyrone 3-position.

Pathway A

Starting with 2-pentanone, a Wadsworth-Emmons reaction is performed with triethyl phosphonoacetate in THF in the presence of NaH. Ester 16 (see FIG. 3) is sequentially reduced with DIBAL and oxidized with DDQ to produce aldehyde 14. A Wadsworth-Emmons reaction is used to condense aldehyde 14 and triethyl 2-phosphonopropionate in THF in the presence of NaH. The resulting product is sequentially reduced with DIBAL and oxidized with DDQ to produce aldehyde 1. This constitutes the 3-position side chain precursor.

The pyrone portion is constructed as follows. Ethyl propionylacetate is hydrolyzed with aqueous NaOH. Two equivalents of the resulting acid are condensed with an equivalent of carbonyldiimidazole to produce pyrone 5 (see FIG. 5). The 3-propionyl group is hydrolyzed using concentrated $H_2SO_4$ at elevated temperature to afford pyrone 6, which is then alkylated with 3-bromopropionaldehyde dimethylacetal using n-BuLi and THF/HMPT as a solvent to give 7. The 4-position hydroxyl is converted to SEM ether 8 using SEM-Cl and diisopropylamine in $CH_2Cl_2$. The dimethylacetal is removed under acidic conditions and the resulting aldehyde is alkylated under Wadsworth-Emmons conditions with triethylphosphonoacetate in THF in the presence of NaH to produce the unsaturated ester 9. The SEM ether is cleaved using TBAF and DMPU to give key intermediate 10.

Intermediate 10 can be synthesized by an alternate pathway. Pyrone 6 is deprotonated with n-BuLi and then alkylated with allyl bromide in THF/HMPT. The 4-position hydroxyl is converted to SEM ether 11 by treatment with SEM-Cl and diisopropylamine in $CH_2Cl_2$. The allyl group is hydroborated using a borane reagent and the subsequent borate is removed oxidatively to give the alcohol. The resulting alcohol is oxidized under standard Swern conditions to give aldehyde 12. Aldehyde 12 was alkylated with triethylphosphonoacetate in THF in the presence of NaH to produce unsaturated ester 9. The SEM ether is removed under acidic conditions, e.g., using $H_2SO_4$ in THF/EtOH, to give the key intermediate 10. An aldol reaction between compounds 1 and 10 catalyzed by TFA in $CH_2Cl_2$ provides intermediate 13. The synthesis can be finished by oxidation to produce intermediate 17 followed by a Curtius sequence to produce myxopyronin A 18.

Pathway B

The second route takes advantage of the convenient availability of intermediates 10 and 14 by processes disclosed below. Pyrone 10 is acylated with propionyl chloride in TFA at elevated temperature to afford intermediate 15 (FIG. 11). A base-catalyzed aldol between compounds 14 and 15 using LDA in THF forms an intermediate that is sequentially treated with mesyl chloride and triethylamine in $CH_2Cl_2$ followed by DBU to afford compound 17, which is also an intermediate in pathway A. Myxopyronin A results after a Curtius sequence.

The present invention provides a process of preparing a myxopyronin having the structure:

which comprises:

(a) condensing an aldehyde having the structure:

with a pyronye having the structure:

under suitable conditions to form an adduct having the structure:

(b) oxidizing the adduct formed in step (a) under suitable conditions to form a pyrone ketone having the structure:

and (c) (i) saponifying the pyrone ketone formed in step (b) under suitable conditions to form a pyrone acid;

(ii) acylating the pyrone acid formed in step (c)(i) under suitable conditions to form a pyrone anhydride; and (iii) treating the pyrone an hydride formed in step (c)(ii) with an azide salt to form a pyrone acyl azide; and (iv) heating the pyrone acyl azide formed in step (c)(iii) in methanol under suitable conditions to form myxopyronin A.

As practiced in the present invention, the 1,2-addition step (a) recited above is performed using an acid catalyst, such as trifluoroacetic acid (TFA), hydrochloric acid, sulfuric acid, or p-toluenesulfonic acid, preferably in the presence of a dehydrating agent, such as molecular sieves, more preferably using 4Å molecular sieves, in an inert organic solvent, such as dichloromethane or p-dioxane. Alcohol oxidation step (b) is carried out using various oxidants, such as 2,3-dichloro-5,6-dicyano-1,4-benzoquinone (DDQ), manganese dioxide or chromium chlorochromate. Saponifying step (c)(i) is carried out using a hydroxide base, such as LiOH, NaOH, KOH or CsOH, in a solvent mixture comprising water and at least one organic co-solvent, such as methanol, ethanol, or tetrahydrofuran (THF). A preferred solvent composition is methanol/THF/water in the proportion 2:2:1. In the Curtius sequence, step (c)(ii) is effected using an alkyl or aryl chloroformate, including, but not limited to, methyl chloroformate, ethyl chloroformate, isopropyl and phenyl chloroformate, in the presence of a base, such as DIPEA, in an inert organic solvent, preferably miscible with water, preferably, acetone. The resulting product may be purified, or used directly in the subsequent step. Step (c)(iii) is carried out using an azide salt, such as lithium azide, sodium azide, or tetraalkylammonium azide, preferably in the presence of water. Rearrangement step (c)(iv) entails heating the acid azide formed in step (c)(iii) in a solvent mixture, containing an alcohol, such as ethanol, methanol, or phenol, preferably, methanol, and an inert solvent such as benzene or toluene, at elevated temperatures, preferably, at the reflux temperature of the solvent mixture.

The present invention also provides a process of preparing a myxopyronin having the structure:

which comprises:
(a) treating a pyrone having the structure:

[structure: 4-hydroxy-6-substituted-2H-pyran-2-one with CH(CH₃)CH₂CH=CHCO₂Et side chain]

with propionyl chloride under suitable conditions to form a ketone adduct having the structure:

[structure: 3-propionyl-4-hydroxy pyrone with CO₂Et side chain]

(b) (i) condensing the ketone adduct formed in step (a) under suitable conditions with an aldehyde having the structure:

[structure: CH₃CH₂CH₂C(CH₃)=CHCHO]

to form a pyrone aldol; (ii) mesylating the pyrone aldol formed in step (b)(i) under suitable conditions to form a pyrone aldol mesylate; and (iii) reacting the pyrone aldol mesylate under suitable basic conditions to form a pyrone ketone having the structure:

[structure: pyrone ketone with diene chain and CO₂Et side chain]

and (c) (i) saponifying the pyrone ketone formed in step (b)(iii) under suitable conditions to form a pyrone acid;
(ii) acylating the pyrone acid formed in step (c)(i) under suitable conditions to form a pyrone anhydride; and
(iii) treating the pyrone anhydride formed in step (c)(ii) with an azide salt to form a pyrone acyl azide, and (iv) heating the pyrone acyl azide formed in step (c)(iii) under suitable conditions to form the myxopyronin.

Acylation step (a) may be effected using an acid catalyst, such as TFA, hydrochloric acid, or p-toluenesulfonic acid, preferably in the presence of a dehydrating agent, such as molecular sieves, preferably using 4Å molecular sieves, in an inert organic solvent, such as dichloromethane. Condensation step (b)(i) is performed using a strong, non-nucleophilic base, such as LDA, potassium t-butoxide, or sodium hydride, preferably, LDA, in an inert organic solvent, such as THF. Mesylation step (b)(ii) is carried out using an acylating agent, such as mesyl chloride, p-tosyl chloride, acetic anhydride, preferably, mesyl chloride, in the presence of a non-nucleophilic organic base, such as DIPEA or triethylamine. Elimination step (b)(iii) may be performed using a variety of reagents effective to cause elimination, preferably, a strong non-nucleophilic base such as DBU. The Curtius rearrangement is effected as described above.

The present invention also provides a process of preparing an unsaturated aldehyde having the structure:

[structure: unsaturated aldehyde CH₃CH₂CH₂C(CH₃)=CHC(CH₃)=CHCHO]

which comprises:
(a) condensing triethyl phosphonoacetate with 2-pentanone under suitable conditions to form an unsaturated ester having the structure:

[structure: CH₃CH₂CH₂C(CH₃)=CHCO₂Et]

(b) (i) reducing the unsaturated ester formed in step (a) under suitable conditions to form an unsaturated alcohol; and (ii) oxidizing the unsaturated alcohol under conditions suitable to form a monounsaturated aldehyde having the structure:

[structure: CH₃CH₂CH₂C(CH₃)=CHCHO]

and (c) (i) condensing triethyl phosphonopropionate with the monounsaturated aldehyde formed in step (b)(ii) under suitable conditions to form a diene ester;
(ii) reducing the diene ester formed in step (c)(i) under suitable conditions to form a diene alcohol; and
(iii) oxidizing the unsaturated alcohol under suitable to form the unsaturated aldehyde.

As implemented in the present invention, the condensation step, preferably of the Wadsworth-Emmons type, is favorably performed in the presence of a non-nucleophilic base, such as LDA or sodium hydride, in an inert polar, aprotic organic solvent, such as THF. The ester reduction step (b)(i) may be carried out using any of a variety of reducing agents, such as diisobutylaluminum hydride (DIBAL) in an inert aprotic organic solvent, such as THF. Oxidation step (b)(ii) may be effected using any of a range of mild oxidants, preferably, DDQ, in an inert organic solvent, such as dichloromethane. The subsequent condensation step (c)(i) may be performed in the presence of a non-nucleophilic base, such as sodium hydride, in an inert organic solvent, preferably, THF. Reduction step (c)(ii) may be carried out using various reducing agents, preferably, diisobutylaluminum hydride (DIBAL) in an aprotic organic solvent, such as THF. Finally, oxidation step (c)(iii) may be effected using a variety of oxidants, such as DDQ, in dichloromethane.

In one embodiment, the present invention provides a process of preparing the unsaturated ester having the structure:

[structure: CH₃CH₂CH₂C(CH₃)=CHCO₂Et]

which comprises (a) condensing ethyl butyryl acetate with diethyl phosphorochloridate under suitable conditions to form an enol phosphonate; and (b) alkylating the enol phosphonate formed in step (a) with an organometallic reagent under suitable conditions to form the unsaturated ester.

As practiced in the invention, condensing step (a) is performed using a non-nucleophilic base, including, but not limited to, potassium t-butoxide, sodium hydride, LDA, and lithium diethylamide, preferably, sodium hydride, in an inert aprotic organic solvent, such as THF or diethyl ether. Alkylation step (b) is effected using an organometallic reagent, such as lithium dimethyl cuprate, methyl lithium, methyl magnesium bromide or chloride, preferably, lithium dimethyl cuprate, in an inert aprotic solvent, preferably, diethyl ether, at a temperature ranging from about −100° C. to about 0° C., more preferably, from about −90° C. to about −50° C., most preferably, at −78° C.

In addition, the present invention provides a process of preparing a pyrone ester having the structure:

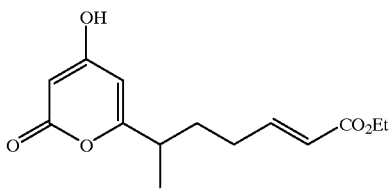

which comprises:

(a) treating a dicarbonyl compound having the structure:

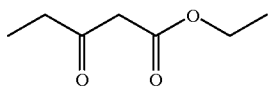

acidifying and dimerizing under suitable conditions to form an acyl pyrone having the structure:

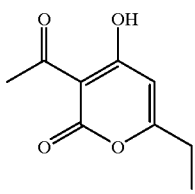

(b) hydrolyzing the acyl pyrone formed in step (a) under suitable conditions to form a pyrone having the structure:

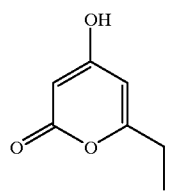

(c) alkylating the pyrone formed in step (b) under suitable conditions to form a pyrone acetal having the structure:

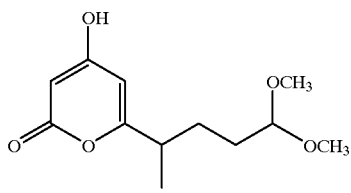

(d) etherifying the pyrone acetal formed in step (c) under suitable conditions to form an ether pyrone acetal having the structure:

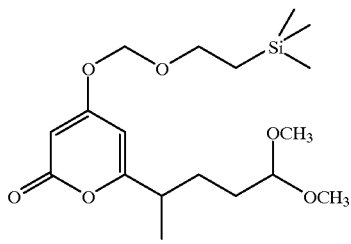

(e) (i) acidolytically cleaving the pyrone acetal under suitable conditions; and (ii) reacting with triethyl phosphonoacetate under suitable conditions to form a protected pyrone ester having the structure:

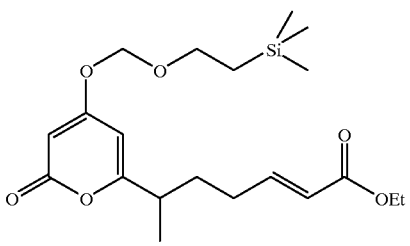

and (f) deprotecting the protected pyrone ester under suitable conditions to form the pyrone ester.

Hydrolysis in step (a) recited above is carried out using a hydroxide base, such as LiOH, NaOH, or KOH, preferably NaOH, followed by acidification with a variety of acids, including, but not limited to, hydrochloric acid, sulfuric acid, phosphoric acid, nitric acid, and TFA, preferably, hydrochloric acid. Dimerization in step (a) is effected using a condensing agent, such as carbonyl diimidazole, or an equivalent reagent known in the art. Hydrolysis step (b) is performed using a strong acid such as hydrochloric acid, hydrobromic, trifluoroacetic or sulfuric acid, preferably 90% sulfuric acid, at elevated temperature, in the range from about 65° C. to about 160° C., preferably between about 100° C. and about 140° C., more preferably, at 130° C. Alkylation step (c) with fluor-, Clair-or bromopropionaldehyde dimethyl acetal is carried out using a strong base such as n-butyl lithium, t-butyl lithium, sec-butyl lithium or phenyl lithium, in an inert polar aprotic solvent, such as THF in the presence or absence of a co-solvent, such as HMPT. Etherification step (d) is effected using a strong non-nucleophilic base such DIPEA or triethylamine in an inert organic solvent, such as dichloromethane. Acetal cleavage step (e)(i) is carried out using a strong acid, such as sulfuric acid or p-tonic acid, in a solvent mixture preferably comprising THF and water in a ratio of 10:1. Condensation step (e)(ii) employs a strong non-nucleophilic base, such as sodium hydride, in a solvent mixture favorably comprising toluene and DMF. Deprotection step (f) utilizes an organic fluoride salt, preferably tetrabutylammonium fluoride.

The present invention further provides a process of preparing a pyrone ester having the structure:

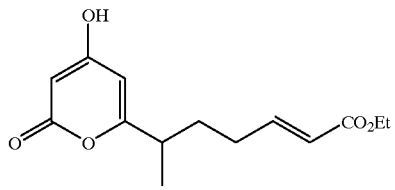

which comprises:

(a) (i) alkylating a pyrone having the structure:

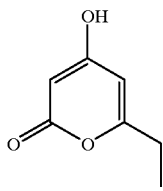

(ii) etherifying the pyrone formed in step (i) under suitable conditions to form protected pyrone having the structure:

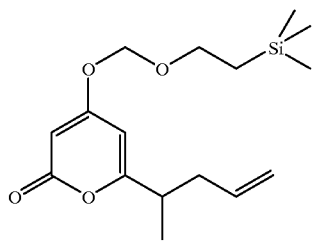

(b) (i) hydroborating the protected pyrone formed in step (a)(ii) under suitable basic conditions; and (ii) oxidizing under suitable conditions to form a pyrone aldehyde having the structure:

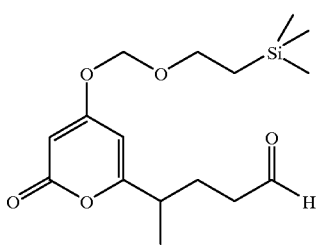

(c) condensing the pyrone aldehyde formed in step (b)(ii) with triethyl phosphonoacetate under suitable conditions to form a protected pyrone ester having the structure:

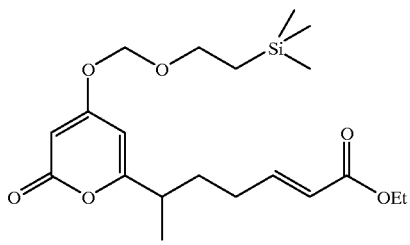

and (d) cleaving the protected pyrone ester under suitable conditions to form the pyrone ester.

As practiced in the invention, allylation step (a)(i) is effected using allyl chloride, bromide or fluoride as the halide and a strong base, such as sodium hydride or n-butyl lithium, in a polar aprotic solvent mixture favorably made up of THF and HMPT. Protection step (a)(ii) is carried out using a strong non-nucleophilic base, such as DIPEA or triethylamine, in an inert organic solvent, such as dichloromethane. Hydroboration (b)(i) is performed with a borane complex, such as $BH_3$-$SMe_2$, followed by treatment with hydrogen peroxide and inorganic base, such as NaOH. Oxidation (b)(ii) preferably utilizes standard Swern conditions. Condensation step (c) is performed using a strong non-nucleophilic base such as sodium hydride. Deprotection step (d) is effected using a strong acid such as sulfuric acid in the presence of a protic solvent, such as ethanol, and a miscible aprotic organic solvent, such as THF.

Generally, the Wadsworth-Emmons reaction is applied in the pathway leading to both 1 and 9, and tolerates the use of aprotic, anhydrous solvents. While both toluene and THF have been used effectively, higher yields are obtained with THF. The preferred base is NaH although other anhydrous bases are also effective. Other reactions generating carbon-carbon double bonds could be equivalently used. Intermediate ester 16 may alternatively be prepared by an addition reaction involving lithium dimethyl cuprate, or an equivalent organometallic reagent. The reductions of the two esters on the pathway to 1 are both performed with DIBAL, although a number of hydride reagents could have been used. Any aprotic, anhydrous solvent would be permissible as long as its melting point is below –78° C. The reaction proceeds rapidly at -78° C, but may optionally be carried out at temperatures up to –40° C. without untoward consequences. The oxidations on the pathway to 1 have been efficiently performed both under Swern conditions and with DDQ, or any reagent proficient in the oxidation of allylic alcohols or primary alcohols, including, but not limited to, manganese oxide, pyridinium chlorochromate, and pyridinium dichromate. The pathway using DDQ is more effective with unsaturated alcohols. The oxidation reaction is preferably performed using a variety of aprotic, anhydrous solvents.

With respect to the production of the pyrone, ethyl propionylacetate is hydroyzed with aqueous NaOH. The reaction may be carried out using any hydroxylic base. The dimerization of the acid to produce pyrone 5 is preferably effected in aprotic, anhydrous solvents. Other carbonyldiimidazole equivalents (e.g., phosphene) can be similarly used. The hydroysis of the propionyl groups to yield 6 occurs in strong acids, including, but not limited to, hydrochloric acid, phosphoric acid, nitric acid. The alkylation of 6 with either 3-bromopropionaldehyde dimethyl acetal or allyl bromide is preferably performed in the presence of hexamethylphosphoric triamide (HMPT) to help solubilize the anion.

The SEM ether is a preferred protecting group. For the installation step, various amine bases may be used, including, but not limited to, diisopropylethylamine (DIPEA), triethylamine, DBU (1,8-diazbicyclo[5.4.0] undec-7-ene), and pyridine. The reaction may be performed in various polar aprotic solvents, including, but not limited to, chloroform, carbon tetrachloride and dimethyl formamide (DMF). The removal of the dimethyl acetal using dilute $H_2SO_4$ in $THF/H_2O$ may be carried out with mild acids which do not cleave the SEM group. In general, if $H_2O$ is used as a co-solvent rather than an alcohol, the SEM group is not affected. The removal of the SEM group in intermediate 9 to produce compound 10 is effected using either TBAF/DMPU or dilute $H_2SO_4$ in THF/EtOH, acidic conditions being the more effective.

The hydroboration of intermediate 11 is carried out with a number of borane reagents, e.g., $BH_3 \cdot THF$ or borane-dimethyl sulfide complex (FIG. 7). Yields are limited by the reactivity of the pyrone under these conditions. The aldol reaction between compounds 1 and 10 is best performed using TFA in $CH_2Cl_2$. In the alternate route used to attach the 3-position side chain, the acylation of compound 10 with propionyl chloride to produce intermediate 15 proceeds efficiently in the presence of TFA at elevated temperature. Lithium diisopropylamide (LDA) is an efficient base for the aldol reaction of between compounds 14 and 15 yielding intermediate 17. A variety of other bases are also useful for the purpose, including, but not limited to, hydroxide bases, lithium-containing bases and alkoxides.

The present invention provides a process of preparing a myxopyronin having the structure:

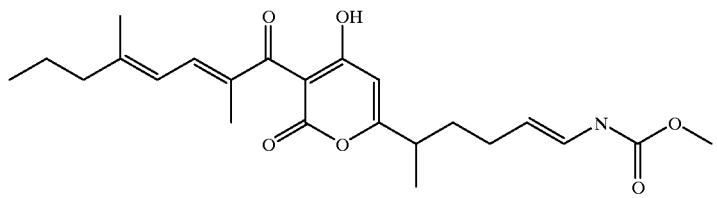

which comprises:

(a) treating an acyl pyrone having the structure:

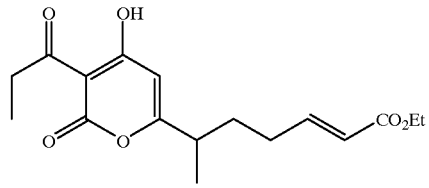

with an unsaturated aldehyde having the structure:

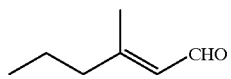

under suitable conditions to form a pyrone aldol having the structure:

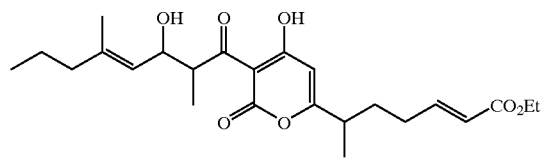

(b)(i) mesylating the pyrone aldol formed in step (a) under suitable conditions to form a pyrone aldol mesylate; and (ii) reacting the pyrone aldol mesylate formed in step (b)(i) under suitable basic conditions to form a pyrone diene having the structure:

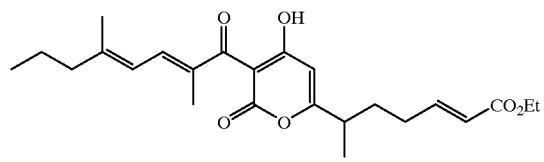

and (c) saponifying the pyrone diene formed in step (b)(ii) under suitable conditions to form a pyrone acid; (d) converting the pyrone acid formed in step (c) under suitable conditions to a pyrone acyl azide; and (e) solvolyzing the pyrone acyl azide formed in step (d) with methanol under suitable conditions to form the myxopyronin.

In one embodiment, the present invention provides a process as disclosed above wherein the acyl pyrone in step (a) is treated with the unsaturated aldehyde in the presence of a Lewis acid catalyst. In a certain embodiment, the present invention provides a process wherein the acid catalyst is titanium tetrachloride/triethylamine combination. In another embodiment, the present invention provides a process as disclosed above wherein the pyrone aldol in step (b)(i) is mesylated with methanesulfonyl (mesyl) chloride in the presence of triethylamine. In another embodiment, the present invention provides a process as disclosed above wherein the pyrone aldol mesylate in step (b)(ii) is reacted with DBU. In another embodiment, the present invention provides a process as above wherein the pyrone diene in step (c) is saponified with lithium hydroxide. In yet another embodiment, the present invention provides a process as above wherein the pyrone acid in step (d) is converted using diphenylphosphoryl azide in the presence of triethylamine.

The aldol condensation of step (a) may be effected at subambient temperatures, preferably at $-78°$ C. Mesylation step (b)(i) is carried out preferably using mesyl chloride but an equivalent reaction sequence would result using another acylating agent, such as p-tosyl chloride, acetic anhydride. Step (b)(i) occurs efficiently in the presence of a non-nucleophilic organic base, such as DIPEA or triethylamine. Elimination step (b)(ii) may be performed using a reagent effective to cause elimination, preferably, a strong non-nucleophilic base such as DBU. Saponifying step (c) is effected using a base such as lithium hydroxide, sodium hydroxide or potassium hydroxide under aqueous or mixed aqueous/dipolar solvent conditions. Converting step (d) is carried out by heating the pyrone acid with diphenylphosphoryl azide, or an equivalent reagent, in the present of a strong non-nucleophilic base, such as triethylamine or diethylisopropylamine, in a noninteracting organic solvent, such as benzene, toluene or xylene, at a temperature above room temperature, preferably at the reflux temperature of the solvent. Solvolyzing step (e) is effected by heating the pyrone acyl azide in methanol at a temperature above room temperature, preferably at the reflux temperature of methanol.

The present invention provides a process of preparing an acyl pyrone having the structure:

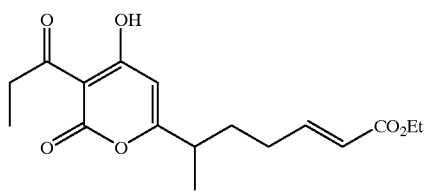

which comprises:

(a) oxidizing a pyrone diol having the structure:

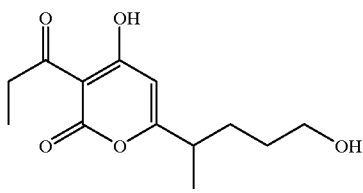

under suitable oxidizing conditions to form a pyrone aldehyde having the structure:

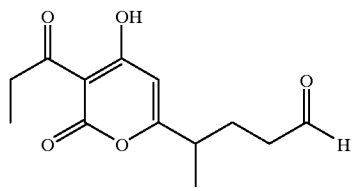

and (b) condensing the pyrone aldehyde formed in step (a) with triethylphosphonoacetate under suitable basic conditions to form the pyrone ester. In one embodiment, the present invention provides a process as shown above wherein the pyrone diol in step (a) is oxidized with a Dess-Martin periodinate. In another embodiment, the present invention provides a process as above wherein the condensing step is effected with sodium hydride.

Oxidizing step (a) is carried out using any oxidant known in the art suited to the purpose, including chromium oxide, pyridinium chlorochromate, dicyclo-hexylcarbodiimide/dimethylsulfoxide, aluminum oxide/acetone, lead tetra acetate, etc. A preferred oxidant is the Dess-Martin periodinate. Condensing step (b) is effected in the presence of a strong non-nucleophilic base, such as sodium hydride or potassium t-butoxide, in an inert organic solvent such as benzene, toluene, or xylene, typically at ambient temperatures.

The present invention provides a process of preparing a pyrone diol having the structure:

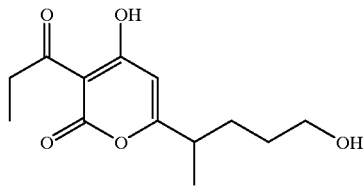

which comprises:

(a)(i) deprotonating an acyl pyrone having the structure:

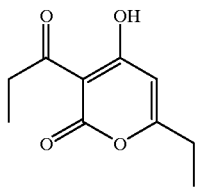

under suitable basic conditions to form an anion; and (ii) alkylating the anion formed in step (a)(i) with a siloxyalkyl halide having the structure:

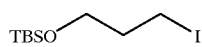

under suitable conditions to form an alkylated pyrone having the structure:

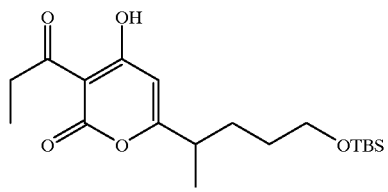

and (b) deprotecting the alkylated pyrone formed in step (a)(ii) under suitable conditions to form the pyrone diol. In one embodiment, the present invention provides a process as disclosed wherein the acyl pyrone in step (a)(i) is deprotonated using lithium diisopropylamide or lithium diethylamide. In another embodiment, the present invention provides a process as above wherein the alkylated pyrone in step (b) is deprotected with a weak acid. In a certain embodiment, the invention provides a process wherein the weak acid is acetic acid.

Deprotonating step (a)(i) is carried out using a strong non-nucleophilic base, such as LDA, lithium diethylamide, potassium t-butoxide, sodium amide, sodium hydride, etc., in a non-interacting organic dipolar solvent or solvent mixture, such as tetrahydrofuran (THF) and/or hexamethylphosphoramide (HMPA), at subambient temperatures, preferably at −78° C. The deprotonated dianion is used directly in the alkylation step (a)(ii) is performed at subambient temperatures, preferably −78° C.

The present invention provides a process of preparing a myxopyronin having the structure:

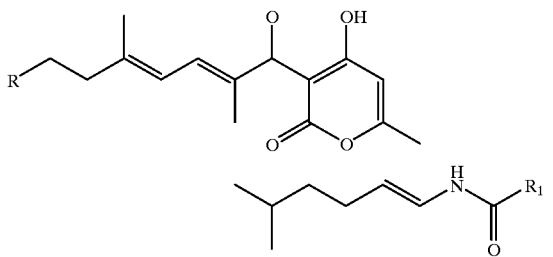

wherein R is $C_{1-9}$ alkyl, and wherein $R_1$ is $C_{1-9}$ alkoxy; which comprises:

(a) condensing an aldehyde having the structure:

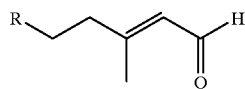

with a pyrone having the structure:

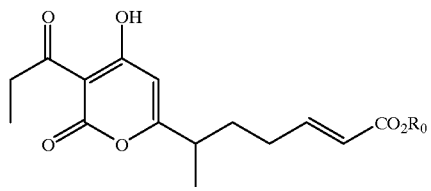

wherein $R_0$ is $C_{1-9}$ alkyl, under suitable conditions to form a pyrone ketone having the structure:

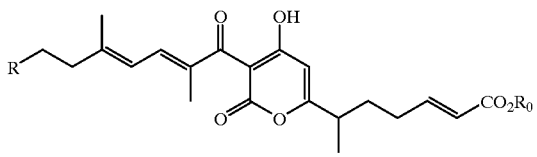

and (b) (i) saponifying the pyrone ketone formed in step (a) under suitable conditions to form a pyrone acid; and (ii) treating the pyrone acid under suitable Curtius conditions to form the myxopyronin.

In one embodiment, the subject invention provides a process as above wherein the pyrone is condensed with the aldehyde in the presence of a titanium(IV) reagent. In another embodiment, the pyrone ketone is saponified in the presence of a hydroxide salt. For example, the hydroxide salt is LiOH, NaOH, KOH, ammonium hydroxide, tetramethylammonium hydroxide, tetraethyl-ammonium hydroxide, tetra-n-propylammonium hydroxide or tetra-n-butylammonium hydroxide. In a certain embodiment, the present invention provides a process as above wherein the Curtius conditions comprise:

(a) acylating the pyrone acid to form a pyrone anhydride;
(b) treating the pyrone anhydride formed in step (a) with an azide salt to form a pyrone acyl azide; and
(c) heating the pyrone acyl azide formed in step (b) with an alcohol $R_1OH$ under conditions suitable to form the myxopyronin. In one embodiment, the process is carried out using methanol as the alcohol $R_1OH$. In another embodiment, the pyrone is treated with alkyl haloformate, and subsequently with an azide salt. The alkylhaloformate may favorably be methyl or ethyl chloroformate, and the azide salt may be $LiN_3$ or $NaN_3$. In addition, R may be methyl or ethyl. The present invention also provides a process of preparing an unsaturated aldehyde having the structure:

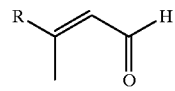

wherein R is $C_{1-9}$ alkyl; which comprises:

(a) treating an acetylene having the structure:

with a first organometallic reagent to form a first intermediate;

(b) reacting the first intermediate with a second organometallic reagent so as to form a second intermediate comprising a reactive (E)-trisubstituted vinylaluminate;

(c) condensing the second intermediate with paraformaldehyde under suitable conditions to form an allylic alcohol having the structure:

and (d) oxidizing the allylic alcohol formed is step (c) under suitable conditions to form the unsaturated aldehyde.

In one embodiment, the process may be effected wherein the first organometallic reagent comprises a zirconocene dihalide in the presence of a trialkylalane. In particular, the zirconocene dihalide is zirconocene dichloride and the trialane is trimethylaluminum. In another embodiment, the process may be effected wherein the second organometallic reagent is an alkyllithium reagent. In this process, the allylic alcohol is oxidized with any of a variety of oxidants suited for the purpose, for example, pyridinium chlorochromate, pyridine dichloride, manganese dioxide, a Swern reagent or tetrapropylammonium perruthenate in the presence of N-methylmorpholine N-oxide.

In treating step (a) disclosed above, the first organometallic reagent is typically prepared from a metallocene dihalide and a trialkylaluminum reagent, using an organic-miscible solvent such as dichloromethane or dichloroethane, at subambient temperatures, preferably at −5° C. to 5° C., more preferably at 0° C. The addition of the acetylenic reagent may be effected at a temperature between −20° C. and 30° C., preferably at 15° C. to 25° C., more preferably at room temperature. Prior to step (b), solvents are evaporated and the residue is extracted with a hydrocarbon solvent, such as n-pentane, n-hexanes or heptane. This extract is then treated with the second organometallic reagent, for example, an alkyl lithium such as n-butyl lithium, typically at subambient temperatures, preferably at 0° C. Condensing step (c) may be carried out by transferring the solution of the second intermediate to a suspension of paraformaldehyde in a non-aqueous dipolar solvent such as THF, at a temperature ranging from 0° C. to 35° C., but preferably at room temperature.

The present invention further provides a process of preparing a myxopyronin having the structure:

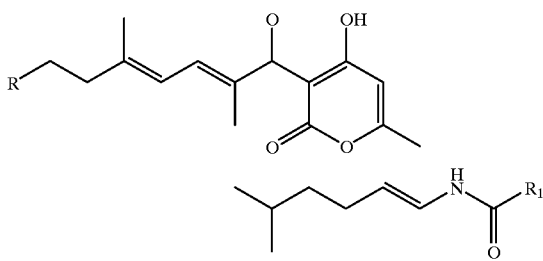

wherein R is $C_{1-9}$ alkyl, and wherein $R_1$ is $NH_2$, alkyl amine, dialkylamine, or optionally substituted phenylamine; which comprises:

(a) saponifying a pyrone ketone having the structure:

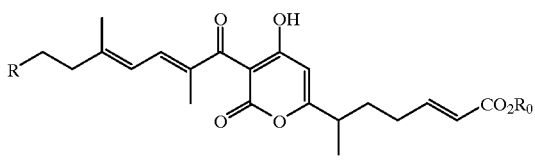

wherein $R_0$ is $C_{1-9}$ alkyl, under suitable conditions to form a pyrone acid; and (ii) treating the pyrone acid under suitable Curtius rearrangement conditions to form the myxopyronin. In one embodiment, the pyrone ketone is saponified in the presence of a hydroxide salt. The hydroxide salt may be LiOH, NaOH, KOH, ammonium hydroxide, tetramethylammonium hydroxide, tetraethylammonium hydrox-ide, tetra-n-propylammonium hydroxide or tetra-n-butyl-ammonium hydroxide. The process is favorably carried out wherein the Curtius conditions comprise:

(a) acylating the pyrone acid to form a pyrone anhydride;

(b) treating the pyrone anhydride formed in step (a) with an azide salt to form a pyrone acyl azide; and (c) treating the pyrone acyl azide formed in step (b) with an ammonia, alkylamine, dialkylamine or optionally substituted phenylamine under conditions suitable to form the myxopyronin. In one embodiment, the alkylamine is methylamine. In another embodiment, the pyrone is treated with an alkyl haloformate, and subsequently with an azide salt. In particular, the alkylhaloformate is favorably methyl or ethyl chloroformate, and the azide salt is $LiN_3$ or $NaN_3$. The process may be carried out wherein R is methyl or ethyl.

In saponifying step (a) the pyrone ketone is dissolved in a nonaqueous dipolar solvent such as THF and treated with a hydroxide salt such as lithium hydroxide, sodium hydroxide, or potassium hydroxide, preferably lithium hydroxide, at a temperature ranging from 0° C. to 45° C., and preferably at room temperature. In treating step (b) the azide salt may be any suitable azide salt, such as trimethyammonium azide, lithium azide, sodium azide or potassium azide, which is dissolved water with or without a miscible non-reactive cosolvent prior to addition to the product of step (a), favorably at subambient temperatures, preferably at 0° C. Treating step (c) is carried out in a non-reactive dipolar solvent such as THF at a temperature determined by the ammonia or amine component reacted, and may range from −78° C. to 120° C.

A composition of matter having the structure:

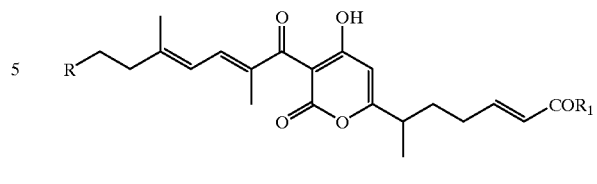

wherein R is $C_{1-9}$ alkyl, and wherein RP is H, $C_{1-9}$ alkyl, benzyl, optionally substituted phenyl, OH, $C_{1-9}$ alkoxy, $NH_2$, alkylamine, dialkylamine, or optionally substituted phenylamine.

The present also provides a composition of matter having the structure:

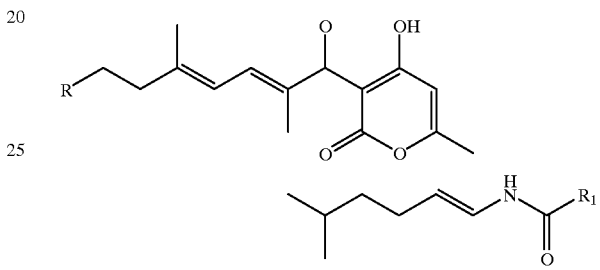

wherein R is $C_{1-9}$ alkyl, and wherein $R_1$ is H, $C_{1-9}$ alkyl, benzyl, optionally substituted phenyl, OH, $C_{1-9}$ alkoxy, $NH_2$, alkylamine, dialkylamine, or optionally substituted phenylamine; and wherein when R is methyl or ethyl, $R_1$ is not methoxy.

The present invention further provides the following compositions of matter, having the structures set forth below. These compounds are useful as intermediates in the synthesis of myxopyronins and coral lopyronins according to the present invention:

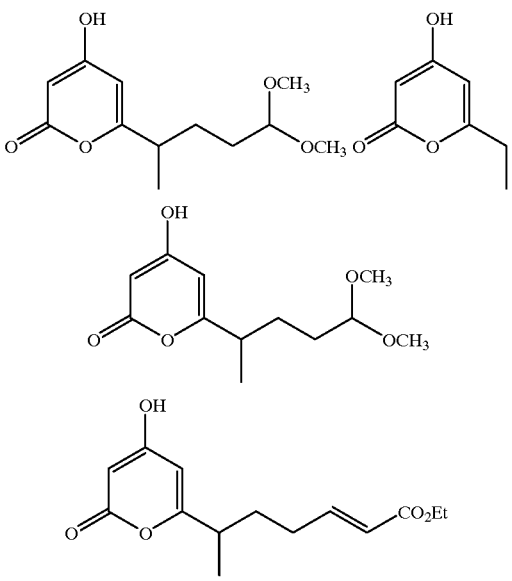

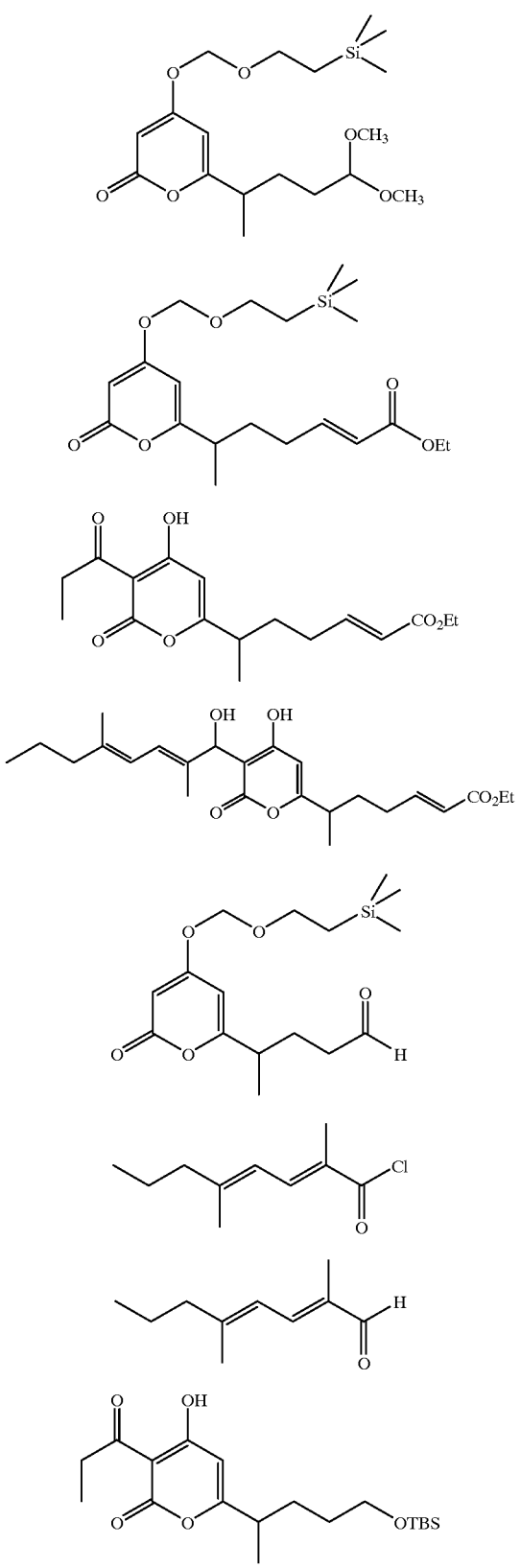
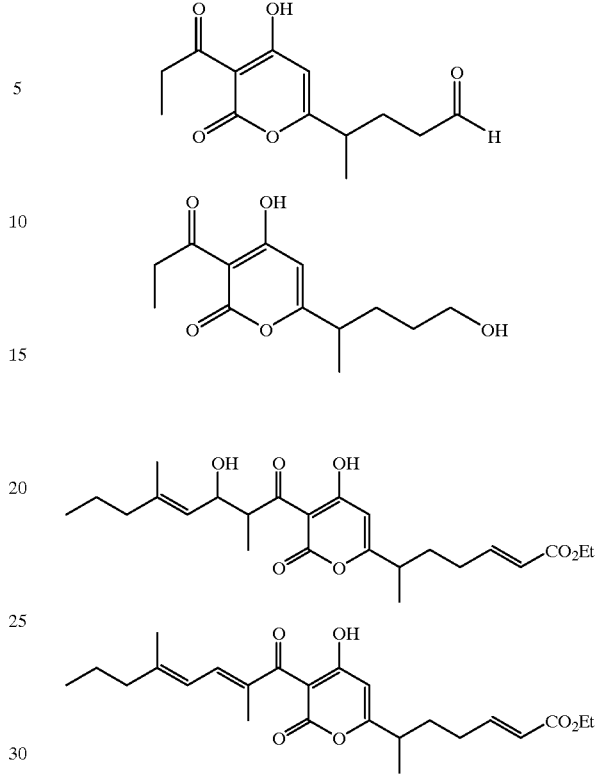

The scope of the present invention includes compositions of matter wherein the $C_\alpha$ carbon at the 6-position of the pyrone ring therein possesses either an R or S absolute configuration, as well as mixtures thereof. The processes of the present invention encompass the use of various alternate protecting groups known in the art. For example, in the preparation of unsaturated aldehyde 1, ethyl ester 16 may be equivalently replaced with a methyl, propyl, isobutyl, phenyl or benzyl ester, wherein the triethylphosphonoacetate or triethylphosphonopropionate may be replaced with the corresponding alternate ester. Similarly, in the preparation of intermediate pyrone ester 10 and of myxopyronin 18, the ethyl ester may be equivalently replaced with, for example, a methyl, propyl, isobutyl, phenyl, or benzyl ester, wherein the triethylphosphonoacetate used in the conversion from 8 to 9 may be replaced with the corresponding alternate ester. Furthermore, in the conversion from compound 6 to 7, the bromopropionaldehyde dimethyl acetal may be equivalently replaced with, for example, an ethyl, propyl, butyl, ethylene, or propylene acetal, and in the conversion from 7 to 8, SEM-Cl may be equivalently replaced with another protecting group, for example, methoxymethyl, methyl-thiomethyl, trimethylsilyl, t-butyldimethylsilyl, or tetrahydropyranyl.

The present invention will be better understood from the Experimental Details which follow. However, one skilled in the art will readily appreciate that the specific methods and results discussed are merely illustrative of the invention as described in the claims which follow thereafter.

General $^1$H and $^{13}$C NMR spectra were taken in $CDCl_3$ at 400 MHz and 75 MHz respectively unless specified otherwise. Chemical shifts are reported in parts per million using the solvent resonance internal standard (chloroform, 7.24 and 77.0 ppm respectively, unless specified otherwise). NMR data are reported as follows: chemical shift, multiplicity (app=apparent, par obsc=partially obscured, ovrlp=overlapping, s=singlet, d - doublet, t=triplet, q=quartet, m=multiplet, br=broad, abq=ab quartet), coupling constant, and integration. Infrared Resonance (IR) spectra were recorded on a Perkin-Elmer 1800 series FTIR spectrophotometer. High resolution mass spectra were obtained on a Finnegan MAT-90 spectrometer in the Boston University Mass Spectrometry Laboratory. Reversed phase preparative HPLC was conducted on a Varian/Rainin SD-200 equipped with Dynamax PDA-2 Diode Array detector, using 22×250 mm Vydac C18 column (218TP1022). Methylene chloride ($CH_2Cl_2$), methanol (MeOH), benzene ($C_6H_6$), toluene, and hexane were distilled from calcium hydride, and tetrahydrofuran (THF) and hexamethyl phosphoramide (HMPA) were distilled from sodium and benzophenone prior to use. Titanium tetrachloride ($TiCl_4$ was freshly distilled from copper powder under reduced pressure before each use. Anhydrous 1, 2-dichloro ethane ($ClCH_2CH_2Cl$), trimethyl aluminum ($AlMe_3$, 2.0M solution in hexanes) and zirconocene dichloride ($Cp_2ZrCl_2$) was purchased from Aldrich Chemical Company Inc. and used without further purification. All other reagents were used as supplied. All reactions were carried out in oven-dried glassware under argon atmosphere unless otherwise noted. Analytical thin layer chromatography was performed on Whatman Reagent 0.25 mm silca gel 60-A plates. Flash chromatography was performed on E. Merck silica gel 230–400 mesh.

EXAMPLE 1

Synthesis of 6-Ethyl Pyrone

Hydrolysis of the Ethyl Propionylacetate 4

To a flame-dried flask under flushing argon containing 25 g (1 75 mmol) of ethyl propionylacetate 4 was added 300 mL of 1.5M NaOH. The solution was stirred at room temperature for 18 hours. TLC indicated that the starting material was gone. The solution was placed in an ice/$H_2O$ bath and concentrated HCl was added until the pH of the solution was 1. The reaction was allowed to warm to room temperature. The solution was saturated with KCl and extracted with EtOAc (3×100 mL) and $CHCl_3$ (3×100 mL). The combined organic layers were dried with $Na_2SO_4$, filtered and evaporated on a rotary evaporator. This yielded 15.5 g (76%) of a white solid. The product needed no further purification and was used directly in the next step.
$^1$H NMR (300 MHz, $CDCl_3$): δ 1.1 (3H, t); 2.6 (2H, q); 3.5 (2H, s).
Dimerization of the acid to produce the pyrone 5
To a flame-dried flask under flushing argon containing 10.55 g (91 mmol, 1 eq) of the acid dissolved in 250 mL of freshly distilled THF was added 16.22 g (100 mmol, 1.1 eq) of carbonyldiimidazole. The reaction was left to stir for 12 hours. The solution was concentrated using a rotary evaporator. The residue was partitioned between 100 mL of $CHCl_3$ and 100 mL of 100% HCl. The aqueous layer was extracted with $CHCl_3$ (2×50 mL). The combined organic layers were dried with $Na_2SO_4$, filtered and evaporated on a rotary evaporator. The product needed no further purification as long as it was left on a vacuum pump long enough to remove any remaining starting acid. This yielded 8.8 g (98%) of 5 a tan solid.
$^1$H NMR (300 MHz, $CDCl_3$): δ 1.15 (3H, t); 1.25 (3H, t); 2.55 (2H, q); 3.1 (2H, q); 5.95 (1H, s).

Removal of the propionoyl group to produce 6
In a round-bottomed flask was placed 11.4 g (58.2 mmol, 1 eq) of the pyrone 5 and it was dissolved in 50 mL of concentrated $H_2SO_4$. The solution was heated to 130° C. in an oil bath for 15 minutes. The reaction was allowed to cool to room temperature. Approximately 50 g of ice was added with stirring. The solution was extracted with $Et_2O$ (3×50 mL). The combined organic layers were dried with $Na_2SO_4$, filtered and evaporated on a rotary evaporator. This yielded 7.7 g (94%) of 6 a tan solid. The product needed no further purification.
$^1$H NMR (300 MHz, $CDCl_3$): δ 1.2 (3H, t); 2.5 (2H, q); 5.65 (1H, d); 6.0 (1H, d).

EXAMPLE 2

Construction of 6-position side chain

3-Bromopropionaldehyde dimethyl acetal approach:

Alkylation of pyrone with 3-bromopropionaldehyde dimethyl acetal to produce 7

To a flame-dried flask under flushing argon containing 2.5 g (18 mmol, 1 eq) of the ethyl pyrone 6 dissolved in 40 mL of freshly distilled THF was added 8 mL of HMPT. The solution was slowly cooled to −78° C. in a dry ice/acetone bath, making sure the ethyl pyrone stayed in solution. Once the temperature had equilibrated, 24.6 mL (39 mmol, 2.2 eq) of 1.6M n-BuLi was added by syringe. The solution quickly became a maroon color. The dry ice/acetone bath was replaced with an ice/$H_2O$ bath and the solution allowed to stir for 30 minutes. At this point, the 3-bromopropionaldehyde dimethyl acetal was added by syringe. The solution was left to stir and warm to room temperature overnight. The reaction was quenched by the addition of 25 mL of $H_2O$. Addition of 1% HCl occurred until the solution was acidic. The solution was extracted with $Et_2O$ (3×50 mL). The combined organic layers were extracted with saturated brine solution, dried with $Na_2SO_4$, filtered and evaporated on a rotary evaporator. The product was 7 a brown oil (1.75 g) and was not purified at this time, and was used directly in the production of the SEM ether. Conversion of the 4-hydroxyl group of 7 into the SEM ether 8

To a flame-dried flask under flushing argon containing 1.75 g (12 mmol, 1 eq) of the crude alkylation product 7 dissolved in 40 mL of anhydrous $CH_2Cl_2$ was added 2.42 mL (12 mmol, 1 eq) of N,N-diisopropylethylamine (DIPEA) by syringe. The solution immediately became orange. The solution was cooled with a ice/$H_2O$ bath and 2.46 mL (12 mmol, 1 eq) of 2-(trimethylsilyl)ethoxymethyl chloride (SEM-Cl) was added by syringe. A white vapor formed. The reaction was allowed to stir for 2 hours at which time TLC showed that no starting material remained (5:2 benzene/ethyl acetate). The reaction was diluted with 150 mL of $Et_2O$ and the resulting solution extracted with saturated $NaHCO_3$ (2×50 mL). The organic layer was extracted with brine solution (1×50 mL). The organic layer was dried with $Na_2SO_4$, filtered and evaporated on a rotary evaporator. The residue was placed on a $SiO_2$ column and eluted with 5:2 benzene/ethyl acetate. This yielded 0.46 g (7% for the two steps combined) of a light yellow oil 8.
$^1$H NMR (300 MHz, $CDCl_3$): δ 0.0 (9H, s); 1.0 (2H, t); 1.2 (3H, d); 1.5–1.8 (4H, m); 2.5 (1H, m); 3.3 (6H, 2s); 3.7 (2H, t); 4.3 (1 H, t); 5.2 (2H, s); 5.6 (1H, d); 5.8 (1H, d).
Deprotection of the aldehyde
In a round-bottomed flask was placed 0.45 g (1.2 mmol, 1 eq) of the pyrone 8 and it was dissolved in 22 mL of a 10:1 mixture of THF/H$_2$O. To this solution was added 10 drops of concentrated H$_2$SO$_4$ and the reaction left to stir. After 3 hours, 3 more drops of H$_2$SO$_4$ were added. After 3 additional hours, TLC showed no more starting material (5:2 benzenel-ethyl acetate). The reaction was diluted with 20 mL of Et$_2$O and this solution extracted with saturated NaHCO$_3$ (1×10 mL) and brine (1×10 mL). The organic layer was dried with Na$_2$SO$_4$, filtered and evaporated on a rotary evaporator. This yielded 0.39 g (>98%) of a light yellow oil 12. The product needed no further purification.

$^1$H NMR (300 MHz, CDCl$_3$): δ 0.0 (9H, s); 1.0 (2H, t); 1.2 (3H, d); 1.8–2.0 (4H, m); 2.6 (1H, m); 3.7 (2H, t); 5.2 (2H, s); 5.6 (1H, d); 5.8 (1H, d) 9.75 (1H, t).

Horner-Emmons-Wadsworth reaction of the deprotected aldehyde to produce 9

To a flame-dried flask under flushing argon containing 0.236 mL (1.2 mmol, 1 eq) of the triethyl phosphonoacetate dissolved in 15 mL of freshly distilled toluene was added 50 mg (1.24 mmol, 1.05 eq) of NaH as a 60% mineral oil dispersion. Hydrogen evolution was witnessed. Once this subsided, 0.40 g (1.2 mmol, 1 eq) of the aldehyde dissolved in toluene (3 mL) was added by syringe. The syringe was washed with an additional 2 mL of toluene and the solution added to the reaction. Almost immediately, an orange oil came out of solution. The reaction was left to stir overnight. The reaction was stopped by the addition of 20 mL of H$_2$O and the solution made acidic with 1% HCl. The solution was extracted with Et$_2$O (3×10 mL). The combined organics were extracted with saturated NaHCO$_3$ (1×10 mL) and brine (1×10 mL). The organic layer was dried with Na$_2$SO$_4$, filtered and evaporated on a rotary evaporator. The residue was placed on a SiO$_2$ column and eluted with 2:1 hexane/ethyl acetate. This yielded 0.347 g (74%) of a clearoil 9.

$^1$H NMR (300 MHz, CDCl$_3$): δ 0.0 (9H, s); 0.9 (2H, t); 1.25 (3H, d); 1.25 (3H, t); 1.6 (2H, m); 1.9 (1H, m); 2.2 (2H, m); 2.6 (1H, m); 3.7 (2H, t); 4.2 (2H, q); 5.2 (2H, s); 5.6 (1H, d); 5.8 (1H, d); 5.85 (1H, d); 6.9 (1H, dt).

EXAMPLE 3

Allyl bromide approach:

Allylation of ethyl pyrone 6

To a flame-dried flask under flushing argon containing 0.108 g (0.77 mmol, 1 eq) of the ethyl pyrone 6 dissolved in 20 mL of freshly distilled THF was added 2 mL of HMPT. The solution was slowly cooled to −78° C. in a dry ice/acetone bath, making sure the ethyl pyrone stayed in solution. Once the temperature had equilibrated, 1.06 mL (1.7 mmol, 2.2 eq) of 1.6M n-BuLi was added by syringe. The solution quickly became a maroon color. The dry ice/acetone bath was replaced with an ice/H$_2$O bath and the solution allowed to stir for 2 hours. At this point, the allyl bromide was added by syringe. As the end of the addition was reached, the color of the solution became almost yellow. The reaction was allowed to stir for 1 hour. The contents of the reaction were partitioned between Et$_2$O and 1N HCl (25 mL of each). The layers were separated and the aqueous was extracted with Et$_2$O (2×25mL). The organics were combined and extracted with 25 mL of saturated KCl. The organic layer was dried with Na$_2$SO$_4$, filtered and evaporated on a rotary evaporator. This yielded 0.110 g (76%) of a light yellow oil, which needed no further purification.

$^1$H NMR (300 MHz, CDCl$_3$): δ 1.2 (3H, d); 2.25 (1H, m); 2.45 (1H, m); 2.6 (1H, m); 5.0 (1H, s); 5.05 (1H, d); 5.6 (1H, d);5.7 (1H, m); 5.9 (1H, d).

Conversion of the 4-hydroxyl group into the SEM ether 11

To a flame-dried flask under flushing argon containing 0.110 g (0.61 mmol, 1 eq) of the crude alkylation product dissolved in 3 mL of anhydrous CH$_2$Cl$_2$ was added 0.106 mL (0.61 mmol, 1 eq) of N,N-diisopropylethylamine (DIPEA) by syringe. The solution, which immediately became orange, was cooled with a iceIH$_2$O bath and 0.108 mL (0.61 mmol, 1 eq) of 2-(trimethylsilyl)ethoxymethyl chloride (SEM-Cl) was added by syringe whereupon a white vapor formed. The reaction was allowed to stir for 2 hours at which time TLC showed that no starting material remained (3:1 hexane/ ethyl acetate). The reaction was diluted with 15 mL of Et$_2$O and the resulting solution extracted with saturated NaHCO$_3$ (2×5 mL). The organic layer was extracted with brine solution (1×5 mL). The organic layer was dried with Na$_2$SO$_4$, filtered and evaporated on a rotary evaporator. The residue was placed on a SiO$_2$ column and eluted with 3:1 hexane/ethyl acetate. This yielded 0.83 g (45%) of 11 as a clear oil.

$^1$H NMR (300 MHz, CDCl$_3$): δ 0.0 (9H, s); 0.9 (2H, t); 1.2 (3H, d); 2.25 (1H, m); 2.45 (1H, m); 2.6 (1H, m); 3.7 (2H, t); 4.2 (2H, q); 5.0 (1H, s); 5.05 (1H, d); 5.2 (2H, s); 5.6 (1H, d);5.7 (1H, m); 5.8 (1H, d).

Hydroboration of the allyl group

To a flame-dried flask under flushing argon containing 0.74 g (2.4 mmol, 1 eq) of the allylation product 11 dissolved in 20 mL of freshly distilled THF and cooled to 0° C. in an ice/H$_2$O bath was added 1.25 mL (2.5 mmol, 1.05 eq) of BH$_3$.THF by syringe. The reaction was allowed to stir for two hours at which time TLC indicated the reaction was finished. The reaction was stopped by sequential addition of 8 mL of methanol, 3 mL of 5M NaOH and 3 mL of 30% H$_2$O$_2$. The solution was acidified to pH 4 with 1% HCl and extracted with Et$_2$O (3×20 mL). The combined organic layers were dried with Na$_2$SO$_4$, filtered and evaporated on a rotary evaporator. The residue was placed on a SiO$_2$ column and eluted with 2:1 ethyl acetate/ toluene. This yielded 0.30 g (38%) of a clear oil.

$^1$H NMR (300 MHz, CDCl$_3$): δ 0.0 (9H, s); 0.9 (2H, t); 1.25 (3H, d); 1.5–1.8 (4H, m); 2.55 (1H, m); 2.45 (1H, m); 2.6 (1H, m); 3.65 (2H, t); 3.75 (2H, t); 5.2 (2H, s); 5.6 (1H, d); 5.8 (1H, d).

Swern oxidation of the alcohol to produce 12

A flame-dried flask under flushing argon containing 0.105 mL (1.5 mmol, 2.55 eq) of DMSO dissolved in 5 mL of anhydrous CH$_2$Cl$_2$ was cooled to −78° C. in a dry ice/acetone bath. To this solution was added 0.058 mL (0.64 mmol, 1.14 eq) of oxalyl chloride by syringe. The solution was allowed to stir for 5 minutes. 0.19 g (0.58 mmol, 1 eq) of the alcohol dissolved in 5 mL of anhydrous CH$_2$Cl$_2$ was added to the solution slowly over the course of 5 minutes. The solution was allowed to stir for 30 minutes. The reaction was terminated by the addition of 0.209 mL (1.5 mmol, 2.6 eq) of triethylamine and stirring for 5 minutes before allowing the solution to warm to room temperature. The solution was diluted with 10 mL of H$_2$O and the aqueous and organic layers separated. The aqueous layer was extracted with CH$_2$Cl$_2$ (2×10 mL). The combined organic layers were dried with Na$_2$SO$_4$, filtered and evaporated on a rotary evaporator. The residue was placed on a SiO$_2$ column and eluted with 2:1 toluene/ethyl acetate. This yielded 0.15 g (80%) of 12 as a clear oil. $^1$H NMR showed this compound identical to the aldehyde prepared using the 3-bromopropionaldehyde dimethyl acetal pathway.

Horner-Emmons-Wadsworth reaction of the aldehyde

To a flame-dried flask under flushing argon in an ice/H$_2$O bath containing 0.223 g (1.1 mmol, 1.05 eq) of the triethyl phosphonoacetate dissolved in 15 mL of freshly distilled THF was added 45 mg (1.1 mmol, 1.05 eq) of NaH as a 60% mineral oil dispersion. Once hydrogen evolution subsided, the aldehyde dissolved in THF (3 mL) was added by syringe. The syringe was washed with an additional 2 mL of THF and the solution added to the reaction. Almost immediately, an orange oil formed. After stirring overnight, the reaction mixture was quenched by the addition of 20 mL of $H_2O$ and the solution was made acidic with 1% HCl. The solution was extracted with $Et_2O$ (3×10 mL). The combined organics were extracted with saturated $NaHCO_3$ (1×10 mL) and brine (1×10 mL). The organic layer was dried with $Na_2SO_4$, filtered and evaporated on a rotary evaporator. The residue was placed on a $SiO_2$ column and eluted with 2:1 hexane/ethyl acetate. This yielded 0.39 g (92%) of a clear oil. $^1H$ NMR showed this compound identical to the HEW adduct prepared using the 3-bromopropionaldehyde dimethyl acetal pathway.

Removal of the SEM protecting group to produce 10

In a round-bottomed flask was placed 0.55 g (1.4 mmol, 1 eq) of the pyrone and it was dissolved in 33 mL of a 10:1 mixture of THF/EtOH. To this solution was added 30 drops of concentrated $H_2SO_4$ and the reaction left to stir. After 6 hours, TLC indicated no starting material. The reaction was diluted with 30 mL of ethyl acetate. The solution was extracted with saturated $NaHCO_3$ (3×20 mL). The aqueous layer was acidified to <pH 4 with 10% HCl. The solution was extracted with ethyl acetate (3×30 mL). The combined organic layers were dried with $Na_2SO_4$, filtered and evaporated on a rotary evaporator. This yielded 0.37 g (>98%) of 10 as a clear oil. The product needed no further purification.
$^1H$ NMR (300 MHz, $CDCl_3$): δ 1.25 (3H, d); 1.25 (3H, t); 1.7 (1H, m); 1.9 (1H, m); 2.2 (2H, m); 2.6 (1H, m); 4.2 (2H, q); 5.5 (1H, d); 5.8 (1H, d); 5.95 (1H, d); 6.9 (1H, dt).

EXAMPLE 4

Synthesis of the 3-position sidechain:

Horner-Emmons-Wadsworth reaction of 2-pentanone with triethyl phosphonoacetate

To a flame-dried flask under flushing argon in an ice/$H_2O$ bath containing 7.48 mL (37.7 mmol, 1 eq) of the triethyl phosphonoacetate dissolved in 100 mL of freshly distilled toluene was added 0.95 g (40 mmol, 1.05 eq) of NaH as a 60% mineral oil dispersion. Once hydrogen evolution subsided, 2-pentanone was added. Almost immediately, an orange oil formed. After stirring overnight, the reaction was quenched by the addition of 50 mL of $H_2O$ and the solution was made acidic with 1% HCl and extracted with $Et_2O$ (3×20 mL). The combined organics were extracted with saturated $NaHCO_3$ (1×10 mL) and brine (1×10 mL). The organic layer was dried with $Na_2SO_4$, filtered and evaporated on a rotary evaporator. The residue was placed on a $SiO_2$ column and eluted with 15:1 hexane/ethyl acetate. This yielded 4.9 g (83%) of a clear oil.
$^1H$ NMR (300 MHz, $CDCl_3$): δ 0.9 (3H, t); 1.25 (3H, t); 1.5 (2H, m); 2.1 (2H, t) 2.15 (3H, s); 4.15 (2H, q); 5.65 (1H, s).

Alternate synthesis of the unsaturated ester 16

To a flask containing 45.7 g (240 mmol, 1 eq) of CuI suspended in 240 mL of diethyl ether cooled to 0° C. with an ice/$H_2O$ bath was added 343 mL (480 mmol, 2 eq) of a 1.4M solution of MeLi over the course of 1 hour. The solution was stirred for 5 minutes at 0° C. and then cooled to -78° C. with a dry ice/acetone bath. Initially, a yellow precipitate formed upon the addition of the MeLi but solubilized with time.

In a second flask, 18.98 g (120 mmol, 1 eq) of ethylbutyryl acetate in 160 mL of diethyl ether was added to a suspension of 5.28 g (132 mmol, 1.1 eq) of NaH in 80 mL of diethyl ether cooled to 0° C. over the course of 1 hour. The slurry that formed was stirred for 20 minutes at 0° C. 19.1 mL (132 mmol, 1.1. eq) of diethylphosphoro-chloridate was added over the course of 10 minutes. The solution was stirred at room temperature for 2 hours and then poured into 200 mL of ice/saturated $NH_4Cl$. The aqueous and organic layers were separated. The organic layer was washed with 300 mL of saturated $NaHCO_3$. The organic layer was dried with $Na_2SO_4$, filtered and evaporated on a rotary evaporator. This yielded the 35.4 g of the enol phosphonate which was used without further purification. The enol phosphonate was dissolved in 120 mL of diethyl ether and added to the first flask containing $LiMe_2Cu$ over the course of 20 minutes with the solution was being cooled to -78° C. The solution was stirred for 2.5 hours while being cooled at -78° C. The solution was poured into 300 mL of saturated $NH_4Cl$. The aqueous and organic layers were separated. The organic layer was washed with 2×200 mL of saturated $NaHCO_3$ and 300 mL of brine solution. The organic layer was dried with $Na_2SO_4$, filtered and evaporated on a rotary evaporator. This yielded 17 g of a light green liquid that was distilled to give 10.4 g (55%) yield of a colorless oil. The NMR was identical to that of 16 but contained a 10:1 ratio of E/Z isomers.

DIBAL reduction of the ethyl ester

A flame-dried flask under flushing argon containing 4.9 g (31.4 mmol, 1 eq) of the ethyl ester dissolved in 100 mL of freshly distilled THF was cooled to -78° C. with a dry ice/acetone bath. 78.5 mL (78.5 mmol, 2.5 eq) of a 1.0M solution of DIBAL was dripped into the solution by syringe over the course of 10 minutes. The solution was left to stir for 1 hour. Fifty milliliters of methanol were poured into the solution to quench the excess DIBAL. The solution was diluted with 200 mL of $H_2O$. 200 mL of $Et_2O$ was added to the solution followed by 100 mL of 5% HCl. The whole solution was poured into a separatory funnel and the aqueous and organic layers separated. The aqueous layer was extracted with $Et_2O$ (2×50 mL). The combined organic layers were dried with $Na_2SO_4$, filtered and evaporated on a rotary evaporator. The residue was placed on a $SiO_2$ column and eluted with 3:1 hexane/ethyl acetate. This yielded 1.2 g (34%) of a clear oil.
$^1H$ NMR (300 MHz, $CDCl_3$): δ 0.85 (3H, t); 1.4 (2H, m); 1.65 (3H, s); 1.9 (2H, t); 4.1 (2H, d); 5.4 (1H, t).

Swern oxidation of the alcohol to produce 14

A flame-dried flask under flushing argon containing 1.9 mL (26.8 mmol, 2.55 eq) of DMSO dissolved in 30 mL of anhydrous $CH_2Cl_2$ was cooled to -78° C. in a dry ice/acetone bath. To this solution was added 1.05 mL (12 mmol, 1.14 eq) of oxalyl chloride by syringe. The solution was allowed to stir for 5 minutes. 1.2 g (10.5 mmol, 1 eq) of the alcohol dissolved in 10 mL of anhydrous $CH_2Cl_2$ was added to the solution slowly over the course of 5 minutes. The syringe was washed with 10 mL of $CH_2Cl_2$ and this solution added to the reaction. The solution was allowed to stir for 30 minutes. The reaction was stopped by the addition of 3.81 mL (27.3 mmol, 2.6 eq) of triethylamine and stirring for 5 minutes before allowing the solution to warm to room temperature. The solution was diluted with 20 mL of $H_2O$ and the aqueous and organic layers separated. The aqueous layer was extracted with $CH_2Cl_2$ (2×10 mL). The combined organic layers were extracted with brine solution, dried with $Na_2SO_4$, filtered and evaporated on a rotary evaporator. The residue was placed on a $SiO_2$ column and eluted with 2:1 toluene/ethyl acetate. This yielded 0.45 g (38%) of a clear oil 14.

$^1$H NMR (300 MHz, CDCl$_3$): δ 0.9 (3H, t); 1.55 (2H, m); 2.15 (3H, s); 2.2 (2H, t); 5.9 (1H, d); 10.0 (1H, d).

Horner-Emmons-Wadsworth reaction of 14 with triethyl 2-phosphonopropionate

To a flame-dried flask under flushing argon in an ice/H$_2$O bath containing 0.86 mL (4.0 mmol, 1 eq) of the triethyl 2-phosphonopropionate dissolved in 100 mL of freshly distilled toluene was added 0.10 g (4.2 mmol, 1.05 eq) of NaH as a 60% mineral oil dispersion. Once hydrogen evolution subsided, the aldehyde 14 was added. Almost immediately, an orange oil came out of solution. The reaction was left to stir overnight. The reaction was stopped by the addition of 20 mL of H$_2$O and the solution made acidic with 10% HCl. The solution was extracted with Et$_2$O (3×20 mL). The combined organics were extracted with saturated NaHCO$_3$ (1×10 mL) and brine (1×10 mL). The organic layer was dried with Na$_2$SO$_4$, filtered and evaporated on a rotary evaporator. The residue was placed on a SiO$_2$ column and eluted with 11:1 hexane/ethyl acetate. This yielded 0.385 g (50%) of a clear oil.

$^1$H NMR (300 MHz, CDCl$_3$): δ 0.9 (3H, t); 1.3 (3H, t); 1.5 (2H, m); 1.85 (3H, s); 1.95 (3H, s); 2.15 (2H, t) 4.15 (2H, q); 6.1 (1H, d); 7.5 (1H, d).

DIBAL reduction of the ethyl ester

A flame-dried flask under flushing argon containing 1.86 g (9.5 mmol, 1 eq) of the ethyl ester dissolved in 40 mL of freshly distilled THF was cooled to −78° C. with a dry ice/acetone bath. 23.7 mL (23.7 mmol, 2.5 eq) of a 1.0M solution of DIBAL was dripped into the solution by syringe over the course of 5 minutes. The solution was left to stir for 2 hours. An additional 5 mL of DIBAL was added. One hour later, 20 mL of methanol was poured into the solution to quench the excess DIBAL. The solution was diluted with 50 mL of H$_2$O. Fifty milliliters of Et$_2$O were added to the solution followed by 25 mL of 5% HCl. The whole solution was poured into a separatory funnel and the aqueous and organic layers separated. The aqueous layer was extracted with Et$_2$O (2×20 mL). The combined organic layers were dried with Na$_2$SO$_4$, filtered and evaporated on a rotary evaporator. The residue was placed on a SiO$_2$ column and eluted with 3:1 hexane/ethyl acetate. This yielded 1.32 g (91%) of a clear oil.

$^1$H NMR (300 MHz, CDCl$_3$): δ 0.9 (3H, t); 1.45 (2H, m); 1.75 (3H, s); 1.8 (3H, s); 2.05 (2H, t); 4.1 (2H, d); 6.0 (1 H, d); 6.25 (1H, d).

DDQ oxidation of the alcohol to the aldehyde 1

To a flame-dried flask under flushing argon containing 0.7576 g (4.9 mmol, 1 eq) of the alcohol dissolved in 25 mL of freshly distilled THF was added 2.26 g (25 mmol, 2 eq) of DDQ. The reaction was allowed to stir for 2 hours. At this point, 5 g of SiO$_2$ were added and the volatiles evaporated on a rotary evaporator. The resulting solid was placed on top of a SiO$_2$ column and the product eluted with 7:1 hexanes/ ethyl acetate. This yielded 0.39 g (52%) of 1 as a clear oil.

$^1$H NMR (300 MHz, CDCl$_3$): δ 0.9 (3H, t); 1.55 (2H, m); 1.85 (3H, s); 1.95 (3H, s); 2.2 (2H, t) 6.3 (1H, d); 7.1 (1H, d); 9.45 (1H, s).

EXAMPLE 5

Attachment of the 3-position side chain:

Acid-catalyzed aldol reaction between pyrone 10 and aldehyde

To a flame-dried flask under flushing argon containing 0.172 g (650 μmol, 1 eq) of the pyrone 10 dissolved in 20 mL of anhydrous CH$_2$Cl$_2$ was added 34 μl (325 μmol, 0.5 eq) of TFA along with 1 g of 4Å sieves. The reaction was allowed to stir for 5 minutes. At this point, 100 μl (650 μl, 1 eq) of the aldehyde 1 was added. The reaction was capped and heated at 45° C. for 24 hours. An additional equivalent of TFA was added along with 2 mL of CH$_2$Cl$_2$. The reaction was heated for an additional 12 hours. The reaction was filtered. One gram of SiO$_2$ was added to the solution and the solvent evaporated. The product became adsorbed onto the SiO$_2$. The resulting solid was applied to the top of a SiO$_2$ column and eluted successively with 7:1 hexane/ethyl acetate, 2:1 hexane-ethyl acetate, 10:1 ethyl acetate/ chloroform with 2 drops of acetic acid for every 6 mL of eluent. This yielded 45 mg of the aldehyde, 1.5 mg of the product (1 %) 13 and 75 mg of the pyrone.

$^1$H NMR (300 MHz, CDCl$_3$): δ 0.85 (3H, t); 1.2 (3H, d); 1.25 (3H, t); 1.55 (2H, m); 1.65 (1H, m); 1.7 (3H, s); 1.75 (3H, s); 1.9 (1H, m); 2.05 (2H, t); 2.15 (2H, t); 2.55 (1H, m); 4.15 (2H, q); 5.4 (1H, d); 5.5 (1H, d); 5.75 (1H, s); 5.8 (1H, d); 6.2 (1H, s); 6.9 (1H, m).

Acylation of pyrone 10 with propionyl chloride

To a flame-dried flask under flushing argon containing 35 mg (130 μmol, 1 eq) of the pyrone 10 dissolved in 1 mL of anhydrous TFA was added 23 μl (260 μmol, 2 eq) of propionyl chloride. The reaction was heated to 50° C. for 1 hour. An additional 4 equivalents of propionyl chloride were added and the reaction was heated for 12 hours. An additional 4 equivalents of propionyl chloride were added and the reaction was heated for 3 hours. The reaction was partitioned between H$_2$O and ethyl acetate. The aqueous layer was extracted again with ethyl acetate and the organic layers were combined. The combined organic layers were dried with Na$_2$SO$_4$, filtered and evaporated on a rotary evaporator. The residue was placed on a SiO$_2$ column and eluted with 2:1 hexane/ethyl acetate. This yielded 21 mg (50%) of a light orange oil 15.

$^1$H NMR (300 MHz, CDCl$_3$): δ 1.15 (3H, t); 1.25 (3H, d); 1.25 (3H, t); 1.7 (1H, m); 1.9 (1H, m); 2.2 (2H, q); 2.6 (1H, m); 3.1 (2H, q); 4.2 (2H, q); 5.8 (1H, d); 5.95 (1H, s); 6.9 (1H, dt).

Base-catalyzed aldol reaction between pyrone and aldehyde to produce 17

To a flame-dried flask in a −78° C. dry ice/ acetone bath under flushing argon containing 21 mg (65 μmol, 1 eq) of the pyrone 15 dissolved in 3 mL of freshly distilled THF was added 2.9 mL (230 μmol, 3.6 eq) of 0.08M LDA by syringe. The reaction went from a light orange to a dark orange. The reaction was allowed to stir for 30 minutes. The aldehyde was added by syringe. The color of the solution became just a little lighter. After stirring for 90 minutes, the reaction was quenched by addition of saturated NH$_4$Cl solution. Ten milliliters of ethyl acetate were added to dilute the solution. 1% HCl solution was used to make the solution acidic. The aqueous and organic layers were separated. The aqueous layer was extracted with ethyl acetate (2×5 mL). The combined organic layers were dried with Na$_2$SO$_4$, filtered and evaporated on a rotary evaporator. The residue was placed on a SiO$_2$ column and eluted with 4:4:1 hexane/ ethyl acetate/methanol. This yielded 2 mg (8%) of a light yellow oil 17.

$^1$H NMR (300 MHz, CDCl$_3$): δ 0.9 (3H, t); 1.25 (3H, d); 1.25 (3H, t); 1.5 (2H, m); 1.7 (1H, m); 1.85 (3H, t); 1.9 (1H, m); 1.95 (3H, t); 2.15 (2H, t); 2.2 (2H, t); 2.6 (1H, m); 4.2 (2H, q); 5.8 (1H, d); 5.95 (1H, s); 6.15 (1H, d); 6.9 (1H, dt); 7.0 (1H, d).

Hydrolysis of the ester 17 to the acid

To a round-bottomed flask containing 4.0 mg (10 μmol, 1 eq) of the pyrone ester 17 dissolved in 5 mL of 2:2:1 methanol/THF/H$_2$O is added 4 mg (100 μmol, 10 eq) of LiOH.H$_2$O. The solution is stirred at room temperature for 6 hours. The volatiles are evaporated on the rotary evaporator. Any remaining base is quenched by the addition of 1% HCl solution. The aqueous solution is extracted with ethyl acetate (3×10 mL). The combined organic layers are dried with Na$_2$SO$_4$, filtered and evaporated on a rotary evaporator. 2 mg of an oily yellow residue is isolated and the residue is used in the next step without any further purification.

$^1$H NMR (300 MHz, CDCl$_3$): δ 0.9 (3H, t); 1.25 (3H, d); 1.5 (2H, m); 1.7 (1H, m); 1.85 (3H, t); 1.9 (1H, m); 1.95 (3H, t); 2.15 (2H, t); 2.2 (2H, t); 2.6 (1H, m); 5.8 (1H, d); 5.95 (1H, s); 6.15 (1H, d); 6.95 (1H, dt); 7.0 (1H, d).

Curtius sequence

To a flame-dried flask under flushing argon containing 2 mg (5.4 μmol, 1 eq) of the residue from the hydrolysis dissolved in 1 mL of acetone is added 1.8 μl (13 μmol, 2.4 eq) of DIPEA. The solution is cooled to 0° C. using an ice/H$_2$O bath. A solution of 0.83 μl (11 μmol, 2 eq) of methyl chloroformate dissolved in acetone is added dropwise over 30 minutes. After the reaction stirs for 30 minutes, a solution of 1.4 mg (2.2 mmol, 4.0 eq) of NaN$_3$ dissolved in H$_2$O was added. The solution is stirred for 15 minutes and then poured into 30 mL of ice H$_2$O. The acyl azide is extracted with 6-2 mL portions of toluene. The combined organic layers are dried with Na$_2$SO$_4$, filtered and concentrated to 2 mL on a rotary evaporator. This solution is added slowly over the course of 15 minutes to a vigorously refluxing solution of 250 μl of methanol in 1 mL dry toluene. Reflux is maintained for 30 minutes and the volatiles are evaporated on a rotary evaporator. The residue is placed on a SiO$_2$ prep plate and eluted with 95:5 CH$_2$Cl$_2$/methanol. This yields 0.5 mg of 18 as a light yellow oil.

$^1$H NMR (300 MHz, CDCl$_3$): δ 0.9 (3H, t); 1.25 (3H, d); 1.5 (2H, m); 1.7 (1H, m); 1.85 (3H, t); 1.9 (1H, m); 1.95 (3H, t); 2.15 (2H, t); 2.2 (2H, t); 2.6 (1H, m); 3.7 (3H, s); 4.9 (1H, m); 5.95 (1H, s); 6.15 (1H, d); 6.4 (1 H, m); 7.0 (1H, d).

EXAMPLE 6

Modified Curtius Rearrangement

Compound 17a (35 mg, 0.09 mmol), diphenylphosphoryl azide (124 mg, 0.45 mmol) and Et$_3$N (63 μL, 0.45 mmol) was dissolved in C$_6$H$_6$ (8.0 mL) and refluxed for 9.0 h. The reaction mixture was cooled to RT, and anhydrous MeOH (2.0 mL) was added. The reaction mixture was warmed to reflux for 6.0 h, and then concentrated in vacuo. The remaining organic residue was flash chromatographed (30% EtOAc in hexanes as eluant) to provide (±)-myxopyronin A (26.6 mg, 71% yield) as a yellow oil. $^1$H NMR (300 MHz, CDCl$_3$): δ 7.0 (d, J=11.6 Hz, 1H); 6.47 (m, 1H); 6.23 (m, 1H); 6.16 (d, J=11.5 Hz, 1H); 5.94 (s, 1H); 4.94 (m, 1H); 3.72 (s, 3H); 2.6 (m, 1H); 2.15 (t, J=7.7 Hz, 2H); 2.05 (m, 2H); 2.01 (s, 3H); 1.85 (s, 3H); 1.76 (m,1H); 1.57 (m,1H); 1.51 (m, 1H); 1.25 (d, J=6.8 Hz, 3H); 0.92 (t,J=7.3 Hz, 3H). $^1$H NMR (300 MHz, CD$_3$OD): 6 7.15 (d,J=12.0 Hz, 1H); 6.39 (d,J=14.2 Hz,1H); 6.27 (d, J=12.0 Hz, 1H); 6.10 (s,1H); 5.03 (dt,J=7.1, 14.0 Hz, 1H); 3.66 (s, 3H); 2.68 (m, 1H); 2.19 (t,J=7.4 Hz, 2H); 2.01 (m, 2H); 1.93 (s, 3H); 1.81 (s, 3H); 1.76 (m, 1H); 1.59 (m, 1H); 1.52 (m, 2H); 1.25 (d, J=6.9 Hz, 3H); 0.92 (t,J=7.2 Hz, 3H). MS (FABMS): (M+H) calc. 418, anal. 418. IR (Film, KBr): ν$_{max}$=3318 m (b), 2966 s, 2931 s, 2872 m, 1736 s, 1719 s, 1684 m, 1637 s, 1560 s, 1542 s, 1525 s, 1437 m, 1378 m, 1237 m, 1049 m. UV (methanol): λ$_{max}$ (log ε): 224 nm (4.17), 295 nm (4.04).

Saponification of pyrone ester 17

To a round-bottomed flask containing 25.8 mg (62 μmol, 1 equiv) of the pyrone ester 17 dissolved in 5 mL of 2:2:1 methanol/THF/H$_2$O was added 26 mg (620 μmol, 10 equiv) of LiOH.H$_2$O. The solution is stirred at RT for 24 h. The reaction was quenched by the addition of 1% HCl solution. The aqueous solution was extracted with ethyl acetate (3×10 mL). The combined organic layers were dried with Na$_2$SO$_4$, filtered and evaporated in vacuo to provide 25 mg of an oily yellow residue. The residue (compound 17a) was isolated and used in the next step without further purification. $^1$H NMR (400 MHz, CDCl$_3$): δ 7.03 (dt,J=6.9, 15.7 Hz,1H); 7.00 (d,J=11.7 Hz, 1H); 6.16 (d,J=11.6 Hz, 1H); 5.96 (s, 1H); 5.85 (d, J=15.7 Hz, 1 H); 2.61 (m, 1H); 2.25 (m, 2H); 2.15 (t, J=7.6 Hz, 2H); 2.00 (s, 3H); 1.91 (m, 1H); 1.85 (s, 3H); 1.69 (m, 1H); 1.49 (m, 2H); 1.27 (d,J=6.9 Hz, 3H); 0.91 (t,J=7.3 Hz, 3H). MS (FABMS): (M+H) calc. 389, anal. 389. IR (Film, KBr): ν$_{max}$=3436 m (b), 2966 s, 2931 s, 2872 m,1731 s,1713 s, 1613 s, 1548 s (b),1443 m, 1384 m, 1255 m.

Preparation of allyl alcohol 14

To a solution of freshly distilled COCl$_2$ (480 μL, 5.5 mmol) in CH$_2$Cl$_2$ (15 mL) was added DMSO (850 μL, 12 mmol) at −78 ° C. The reaction mixture was stirred at −78 ° C. for 30 min, then the starting alcohol 13a (570 mg, 5.0 mmol, dissolved in 3.0 mL CH$_2$Cl$_2$, plus 2.0 mL wash) was added. This whole reaction mixture was stirred at −78 ° C. for another 30 min then Et$_3$N (3.5 mL, 25 mmol) was added. The reaction was stirred for 1.0 h at −78° C., then warmed to RT for 1.0 h before being quenched by H$_2$O. The reaction mixture was extracted with CH$_2$Cl$_2$ (2×80 mL), dried (MgSO$_4$), filtered and concentrated in vacuo to afford the crude aldehyde. The crude product was purified by flash chromatography (10% EtOAc in hexanes as eluant) to provide viscous aldehyde 14 (548 mg, 98% yield) as a colorless oil. $^1$H NMR (400 MHz, CDCl$_3$): δ 0.91 (t, 3H); 1.51 (m, 2H); 2.14 (s, 3H); 2.2 (t, 2H); 5.9 (d, 1H); 10.0 (d, 1H). $^{13}$C NMR (67.5 MHz, CDCl$_3$): δ 14.01; 17.81; 20.69; 42.96; 127.75; 164.49; 191.67.

Preparation of pyrone 5

To a flame-dried flask under a fluching argon atmosphere containing carboxylic acid 4a (10.55 g, 91 mmol, 1 equiv dissolved in 250 mL of freshly distilled THF) was added carbonyldiimidazole (16.22 g, 100 mmol, 1.1 equiv). The reaction was left stirring for 12 h before being concentrated on a rotary evaporator. The residue was partitioned between 100 mL of CHCl$_3$ and 100 mL of 100% HCl. The aqueous layer was extracted with CHCl$_3$ (2×50 mL). The combined organic layers were dried with Na$_2$SO$_4$, filtered and evaporated on a rotary evaporator. The product needed no further purification provided it is left on a vacuum pump for sufficient duration to remove any remaining starting acid. This yielded compound 5 (8.8 g, 98%) as a tan solid. $^1$H NMR (300 MHz, CDCl$_3$): δ 5.91 (s, 1H); 3.10 (q,J=7.3 Hz, 2H); 2.53 (q,J=7.2 Hz, 2H); 1.24 (t,J=7.5 Hz, 3H); 1.15 (t, J=7.2 Hz, 3H). $^{13}$C NMR (75 MHz, CDCl$_3$): δ 208.36; 181.16; 173.52; 161.16; 99.92; 99.56; 35.372; 27.52; 10.49; 7.78. MS (EI): calc. 196.0, anal. 196.0. IR (Film, KBr): ν$_{max}$=3400 m (b), 3020 s, 1710 s (b), 1625 m (b), 1555 s (b), 1430 w (b), 1315 vs, 760 vs (b).

Preparation iodide 8b

To a solution of imidazole (10.2 g, 150 mmol) and triphenylphosphine (14.4 g, 55 mmol) in CH$_2$Cl$_2$ (200 mL) at 0° C. was added 1$_2$ (14.0 g, 55 mmol). After 10 min, a solution of alcohol 8a (9.5 g, 50 mmol) in CH$_2$Cl$_2$ (100 mL) was added over 5 min. The mixture was warmed to RT, covered in aluminum foil, and stirred for an additional 15 h in the dark. The reaction was then diluted with 2.0 mL saturated Na$_2$S$_2$O$_4$ aqueous solution before further dilution with water (150 mL). The organic layer was separated and the aqueous layer was back extracted with $CH_2Cl_2$ (2×80 mL). The combined organic layers were dried ($MgSO_4$), filtered, and concentrated in vacuo. The crude product was purified by flash chromatography (2% EtOAc in hexanes as eluant) to afford iodide 8b (14.4 g, 96% yield) as a pale oil. $^1$H NMR (400 MHz, $CDCl_3$): δ 3.64 (t, 2H); 3.25 (t, 2H); 1.96 (m, 2H); 0.87 (s, 9H); 0.05 (s, 6H). $^{13}$C NMR (67.5 MHz, $CDCl_3$): δ 62.32; 36.14; 25.90; 8.26; 3.61; -5.33.

Preparation of allyl alcohol 13a

To a white slurry solution of zirconocene dichloride (11.7 g, 40 mmol) in 100 mL $(CH_2)_2Cl_2$ was added $AlMe_3$ (40 mL, 2.0M in hexanes, 80 mmol) at 0° C., stirred for 45 min, and then warmed to RT for 1.5 h. To this lemon-yellow solution was added 1-pentyne (2.72 g, 40 mmol, dissolved in 20 mL $(CH_2)_2Cl_2$) at RT. The reaction was allowed to stir for 3.0 h. Then the solvent and the unreacted trimethylalane were evaporated under reduced pressure (maximum 50° C., 0.3 mm Hg, 2~3 h). The remaining orange-yellow organic residue was extracted with dry hexanes (4×30 mL), and the yellow extract was transferred to a 500 mL round-bottom flask via a cannula. To this was added n-BuLi (16 mL, 2.5M in hexanes, 40 mmol) at 0° C. This orange-yellow slurry/solution was stirred from 0° C. to RT for 1.5 h, and then THF (70 mL) was added to dissolve the precipitate. The resulting solution (homogeneous, brown-yellow color) was cannulated to a suspension of paraformaldehyde in THF under a $N_2$ atmosphere. This orange-yellow suspension solution was allowed to stir at RT for 20 min.

The reaction was cooled to 0° C. (ice water bath), ice was added to quench the reaction, and then saturated $NH_4Cl$ (100 mL) was added. The ice bath was removed and the reaction was further acidified with 3M HCl until the reaction turned to a clear yellow (homogeneous) solution. At this time, the reaction pH was 2~3. The organic layer was separated, and the aqueous layer was extracted with ether (2×150 mL). The organic extracts were combined and washed with a saturated solution $NaHCO_3$ (200 mL), then dried with $Na_2SO_4$, filtered and concentrated under reduced pressure to provide crude allylic alcohol 13a. The crude product was purified by flash chromatography (20% EtOAc in hexanes as eluant) to afford alcohol 13a (3.37 g, 74% yield) as a colorless oil. $^1$H NMR (400 MHz, $CDCl_3$): δ 5.4 (t,1H); 4.1 (d, 2H); 1.9 (t, 2H); 1.65 (s, 3H); 1.4 (m, 2H); 0.85 (t, 3H). $^{13}$C NMR (75 MHz, $CDCl_3$): δ 139.15; 123.33; 59.01; 58.97; 41.54; 41.50; 20.61; 15.88; 13.57.

Preparation of acid 4a

Ethyl propionate (25 g, 175 mmol) was dissolved in 30 mL of 1.5M solution NaOH and stirred at RT for 38 h. The reaction was cooled to 0° C., and 3M HCl was slowly added until the reaction system reached a pH ~1, then solid KCl was added to saturate the reaction, followed by EtOAc extraction (3×100 mL), and $CHCl_3$ (2×100 mL). The combined organic layers were dried with $Na_2SO_4$, filtered and evaporated on a rotary evaporator. This protocol afforded the carboxylic acid 4a (15.5 g, 76% yield) as a white solid. The product was used in the next step without further purification. $^1$H NMR (300 MHz, $CDCl_3$): δ 3.52 (s, 2H); 2.60 (q, J=7.3 Hz, 2H); 1.10 (t, J=7.3 Hz, 3H). $^{13}$C NMR (75 MHz, $CDCl_3$): δ 204.28; 172.32; 47.87; 36.60; 7.45. MS (EI): calc. 116.1, anal. 116.1. IR (Film, KBr): $v_{max}$=3400 m (b), 3020 s, 1708 s (b), 1620 w, 1410 m, 1300 m, 1218 vs, 1110 w,1040 w, 925 w, 760 vs.

Preparation of alcohol 8a

To a suspension of NaH (4.0 g, 100 mmol, 60% dispension in mineral oil) in THF (100 mL) at RT was added 1,3-propane diol (7.6 g, 100 mmol, dissolved in 50 mL of THF) via a cannula. The resulting mixture was stirred at RT for 45 min, then a solution of TBSCl (15.0 g, 100 mmol) in 50 mL THF was added to the reaction mixture by cannula. This resulting mixture was stirred for 1.0 h at RT. The reaction was quenched with saturated $NaHCO_3$ aqueous solution (200 mL), and extracted with ether (2×200 mL). The combined organic layers were dried ($MgSO_4$), filtered, and concentrated in vacuo. The crude product was purified by flash chromatography (20% EtOAc in petroleum ether as eluant) to afford the pure mono-protected alcohol 8a (18.1 g, 98% yield) as a clear oil. $^1$H NMR (400 MHz, $CDCl_3$): δ 3.73–3.80 (m, 4H); 2.71 (br s, 1H); 1.74 (m, 2H); 0.86 (s, 9H); 0.04 (s, 6H). $^{13}$C NMR (75 MHz, $CDCl_3$): δ 62.70; 62.16; 34.22; 25.89; 25.81; 25.76; 18.13; -5.55.

Preparation of pyrone 5a

To a stirred solution of diisopropylamine (3.34 mL, 24 mmol) in 25 mL THF at –78° C. under an argon atmosphere was added n-butyl lithium (9.45 mL, 2.5M solution in hexanes, 23.6 mmol). The mixture was allowed to warm to 0° C. for 30 min and then recooled to –78° C. The resulting solution was treated with a solution of pyrone 5 (1.47 g, 7.5 mmol) in 10 mL of THF, and stirred for 1.0 h at –78° C. The derived dianion was treated with iodide 8b (2.5 g, 8.25 mmol) in 10 mL THF, followed by the addition of HMPA (4.0 mL, 23.2 mmol). The reaction mixture was allowed to stir for 30 min at –78° C., before being diluted with saturated $NH_4Cl$ aqueous solution (50 mL). The organic layer was separated, and the aqueous layer was extracted with ether (2×50 mL). All organic layers were combined and dried ($MgSO_4$), filtered, and concentrated in vacuo. The resulting crude oil was purified by flash chromatography (20% EtOAc in hexanes as eluant) to afford the pure alkylation product 5a (2.4 g, 87% yield) as a yellow oil. $^1$H NMR (400 MHz, $CDCl_3$): δ 5.90 (s, 1H); 3.57 (t, 2H); 3.08 (q, 2H); 2.56 (m, 1H); 1.43–1.73 (m, 3H); 1.22 (d, J=7.3 Hz, 3H); 1.13 (t, 3H); 0.86 (s, 9H); 0.01 (s, 6H). $^{13}$C NMR (67.5 MHz, $CDCl_3$): δ 207.81; 180.57; 175.56; 160.64; 99.28; 62.16; 38.27; 34.81; 29.99; 29.72; 25.44; 1 7.82; 1 7.48; 7.27; -5.82.

Preparation of diol 5b

A solution of TBS ether 5a (1.66 g, 4.5 mmol) in 50 mL of AcOH, THF, and water (3:1:1) was stirred at RT for 15 h. The reaction was diluted with 50 mL water, extracted with $CHCl_3$ (2×100 mL). The combined organic layers were washed with a $NaHCO_3$ saturated solution (1×200 mL). The organic layer was separated, and the aqueous layer was back extracted with $CHCl_3$ (1×100 mL). All combined organic layers were dried ($MgSO_4$), filtered, and concentrated in vacuo. The crude product was purified by flash chromatography (40% EtOAc in hexanes as eluant) to afford diol 5b (1.04 g, 91% yield) as a yellow oil. $^1$H NMR (400 MHz, $CDCl_3$): δ 5.90 (s, 1H); 3.63 (br s, 1H); 3.08 (q, 2H); 2.58 (m, 1H); 1.71–1.80 (m, 1H); 1.50–1.62 (m, 3H); 1.33 (br s, 1H); 1.23 (d,J=7.33 Hz, 3H); 1.13 (t, 3H). $^{13}$C NMR (67.5 MHz, $CDCl_3$): 6 180.45; 175.20; 160.62; 99.30; 99.03; 61.62; 38.14; 34.71; 29.83; 29.46; 17.32; 7.14; 1.51.

Preparation of aldehyde 5c

To a solution of alcohol 5b (483 mg, 1.9 mmol) in $CH_2Cl_2$ (20 mL) was added pyridine (845 μL, 10.45 mmol), followed by Dess-Martin periodinate reagent (2.8 mg, 6.65 mmol) in one portion. The resulting reaction mixture was stirred at RT for 2.0 h before being quenched with saturated $NaHCO_3$ aqueous solution. The reaction mixture was extracted with $CH_2Cl_2$ (2×60 mL), dried ($MgSO_4$), filtered, and concentrated in vacuo. The crude product was flash chromatographed (15% EtOAc in hexanes as eluant) to afford aldehyde 5c (417 mg, 87% yield) as yellow oil. $^1$H NMR (400 MHz, $CDCl_3$): δ 5.90 (s, 1H); 3.07 (q, 2H); 2.59

(m, 1H); 2.46 (t, 2H); 1.83–2.02 (m, 2H); 1.23 (d, J=7.33 Hz, 3H); 1.12 (t, 3H). $^{13}$C NMR (67.5 MHz, CDCl$_3$): δ 200.73; 180.69; 174.35; 160.62; 99.93; 99.45; 40.82; 37.82; 35.00; 25.87; 17.52; 7.43; 1.81.

Preparation of acyl pyrone ester 15

To a solution of triethyl phosphonoacetate (1.4 g, 6.24 mmol) in C$_6$H$_6$ (20 mL) at room temperature was added NaH (210 mg, 5.2 mmol, 60% dispersion in mineral oil). The resulting reaction mixture was stirred at RT for 15 min, before aldehyde 5c (525 mg, 2.08 mmol) in 15 mL C$_6$H$_6$ was added via cannula. The reaction was allowed to stir at RT for 1 h before being diluted with aqueous NH$_4$Cl solution (50 mL). The mixture was extracted with EtOAc (2×100 mL), dried (MgSO$_4$), filtered, and concentrated in vacuo. The crude product was flash chromatographed (15% EtOAc in hexanes as eluant) to afford compound 15 (596 mg, 89% yield) as a yellow oil. $^1$H NMR (400 MHz, CDCl$_3$): δ 6.89 (dt, J=6.8, 15.6 Hz,1H); 5.93 (s,1H); 5.82 (d, J=15.6 Hz, 1H); 4.17 (q, J=7.1 Hz, 2H); 3.11 (q, J=7.1 Hz, 2H); 2.60 (m, 1 H); 2.21 (ddd, J=7.2, 7.3, 7.4 Hz, 2H); 1.89 (m, 1H); 1.69 (m, 1H); 1.28 (t,J=7.1 Hz, 3H); 1.25 (d,J=6.9 Hz, 3H); 1.16 (t, J=7.1 Hz, 3H). $^{13}$C NMR (75 MHz, CDCl$_3$): δ 208.38; 180.98; 174.93; 166.37; 161.00; 147.16; 122.38; 100.17; 99.78; 60.37; 38.36; 35.40; 32.32; 29.59; 17.86; 14.29; 7.77. IR (film, KBr): ν$_{max}$=2978 s, 2942 s, 1731 s (b), 1637 s, 1631 s, 1554 s, 1443 s, 1272 m, 1178 m, 1043 m.

Preparation of pyrone diol 14a

Compound 15 (55 mg, 0.17 mmol) was dissolved in 3.5 mL CH$_2$Cl$_2$ and stirred at −78° C. under argon atmosphere. To this yellow homogeneous solution was added freshly distilled TiCl$_4$ (75 μl, 0.68 mmol); the reaction mixture became an orange-yellow slurry instantly. After stirring for 30 min at −78 ° C., Et$_3$N (104 μL, 0.75 mmol) was added, and the reaction mixture became dark red. After stirring at −78° C. for 3.0 h, aldehyde 14 (57 mg, 0.51 mmol) dissolved in 2.0 mL CH$_2$Cl$_2$ was added via a cannula. This dark red mixture was stirred at −78° C. for 17 h before it was quenched with distilled water, and extracted with CHCl$_3$ (3×30 mL). The organic layers were dried (Na$_2$SO$_4$), and concentrated in vacuo. The crude product was flash chromatographed (25% EtOAc in hexanes as eluant) to provide diol 14a (53 mg, 71% yield) as a sticky yellow oil. $^1$H NMR (400 MHz, CDCl$_3$): δ 6.86 (dt, 1H); 5.90 (s, 1H); 5.80 (d, J=15.87 Hz, 1H); 5.21 (d, J=8.55 Hz, 1H); 4.74 (m, 1H); 4.08-1.18 (m, 3H); 2.57 (m, 1H); 2.42 (br s, 1H); 2.19 (dt, 2H); 1.94 (t, 2H); 1.83–1.90 (m, 1H); 1.65 (s, 3H); 1.60–1.70 (m, 1H); 1.30–1.43 (m, 2H); 1.19–1.27 (m, 9H); 0.82 (t, 3H).

Preparation of pyrone ester 17

A stirred solution of diol 14a (52 mg, 0.12 mmol) in 4 mL CH$_2$Cl$_2$ was cooled to −15° C. To this solution was added Et$_3$N (67 μL, 0.48 mmol), followed by MsCl (28 μL, 0.36 mmol). The yellow solution was stirred at −15° C. for 30 min, and then warmed to 0° C. over 15 h. To this was added DBU (108 μL, 0.72 mmol), the resulting reaction mixture was stirred from 0° C. to RT over a 12 h time period before being diluted with 2% HCl aqueous solution (10 mL). The mixture was stirred for 5 min then extracted with EtOAc (2×15 mL), dried (Na$_2$SO$_4$), filtered and concentrated in vacuo. The crude product was flash chromatographed (20% EtOAc in hexanes as eluant) to provide compound 17 (36 mg, 72% yield) as yellow oil. $^1$H NMR (400 MHz, CDCl$_3$): δ 7.00 (d,J=11.6 Hz, 1H); 6.91 (dt,J=6.8, 15.6 Hz, 1H); 6.16 (d,J=11.6 Hz, 1H); 5.95 (s, 1H); 5.83 (d,J=15.6 Hz, 1H); 4.19 (q,J=7.1 Hz, 2H); 2.61 (m, 1H); 2.24 (m, 2H); 2.15 (t,J=7.6 Hz, 2H); 1.91 (m, 1H); 2.01 (s, 3H); 1.85 (s, 3H); 1.69 (m, 1 H); 1.49 (m, 2H); 1.29 (t, J=7.1 Hz, 3H); 1.27 (d, J=6.9 Hz, 3H); 0.91 (t, J=7.3 Hz, 3H). $^{13}$C NMR (75 MHz, CDCl$_3$):δ δ 201.72; 180.83; 174.82; 166.42; 160.39; 149.17; 147.25; 133.65; 133.04; 122.37; 120.67; 100.06; 99.17; 60.38; 42.93; 38.27; 32.25; 29.62; 21.04; 17.81; 17.30; 14.29; 13.88; 13.55. MS (FABMS): (M+H) calc. 417, anal. 417. IR (Film, KBr): ν$_{max}$=2966 m, 2931 m, 2872 m, 1748 s, 1736 s, 1719 s, 1701 s, 1560 s, 1542 s, 1454 s.

EXAMPLE 7

Preparation of Compound 15a 3-(1-Propionyl)-4-hydroxy-6-ethyl-2-pyrone (5). Ethyl propionate (5.0 g, 35 mmol) was dissolved in 30 mL of 1.5M solution NaOH and stirred at RT for 30 h. The reaction mixture was cooled to 0° C., and 3M HCl was slowly added until the mixture reached a pH of about 1; then solid KCl was added to saturate the solution. The reaction mixture was extracted with EtOAc (3×100 mL), and CHCl$_3$ (2×100 mL), and the combined organic layers were dried with Na$_2$SO$_4$, filtered and concentrated in vacuo to afforded the crude ethyl propionic acid (3.1 gm, 76% yield) as a white solid. The material was used without further purification in the next step: $^1$H NMR (300 MHz, CDCl$_3$) δ 3.52 (s, 2H), 2.60 (1, J=7.3 Hz, 2H), 1.10 (t, J=7.3 Hz, 3H); $^{13}$C NMR (75 MHz, CDCl$_3$) δ 204,3, 172.3, 47.9,36.6, 7.5; IR (neat) x max: 3400, 3020, 1708, 1620, 1410, 1300, 1218, 1110, 1040, 925, 760.

To a stirring solution of the above ethyl propionic acid (3.1 g, 26.7 mmol) in 50 mL THF was added carbonyldiimidazole (5.6 gm, 34.7 mmol). The reaction was left stirring for 18 h before being quenched with 2% HCl aq. solution (20 mL, pH 2 to 3), and was extracted with EtOAc (3×50 mL). The organic layers were dried (Na$_2$SO$_4$), filtered and then concentrated in vacuo. The product needed no further purification as long as it was left on a vacuum pump for sufficient duration to remove any remaining starting acid. This protocol affords compound 5 (2.22 g, 86%) as a pale yellow solid: $^1$H NMR (400 MHz, CDCl$_3$) δ 5.91 (s, 1H); 3.10 (1, J=7.3 Hz, 2H); 2.53 (q, J=7.2 Hz, 2H); 1.24 (t, J=7.5 Hz, 3H); 1.15 (t, J=7.2 Hz, 3H). $^{13}$C NMR (75 MHz, CDCl$_3$) δ 208.4, 181.2, 1 73.5, 161.2, 99.9, 99.6; 35.4, 27.5, 10.5, 7.8; IR (neat) δ max: 3420, 2980,1731,1640,1437, 1014, 760 cm$^{-1}$.

1-Iodo-3-(tert-butyldimethylsilyloxy)-propane (8c). To a suspension of NaH (4.0 g, 100 mmol, 60% dispersion in mineral oil) in THF (100 mL) at RT was added 1,3-propanediol (7.6 g, 100 mmol, dissolved in 50 mL of THF) via a cannula. The resulting mixture was stirred at RT for 45 min, before a solution of TBSCl (15.0 g, 100 mmol) in 50 mL THF was added by cannula. This resulting reaction was stirred for 1.0 h at RT. The reaction was quenched with saturated aqueous NaHCO$_3$ solution (200 mL), and extracted with ether (2×200 mL). The combined organic layers were dried (MgSO$_4$), filtered, and concentrated in vacuo. The crude product was purified by flash chromatography (20% EtOAc in petroleum ether as eluant) to afford the pure mono-protected alcohol (18.1 g, 98% yield) as a clear oil: $^1$H NMR (400 MHz, CDCl$_3$) δ 3.73–3.80 (m, 4H); 2.71 (br s, 1H); 1.74 (m, 2H); 0.86 (s, 9H); 0.04 (s, 6H); $^{13}$C NMR (67.5 MHz, CDCl$_3$) δ 62.7, 62.2, 34.2, 25.9, 25.8, 25.8, 18.1, -5.6; IR (neat) δ max: 3371,2929, 2853, 1473, 1389, 1361, 1257, 1099, 1006, 837, 776, 662 cm$^{-1}$.

To a solution of imidazole (10.2 g, 150 mmol) and triphenylphosphine (14.4 gm, 55 mmol) in CH$_2$Cl$_2$ (200 mL) at 0° C. was added 12 (14.0 g, 55 mmol). After 10 min, a solution of the above mono-protected alcohol (9.5 g, 50 mmol) in CH$_2$Cl$_2$ (100 mL) was added over 5 min. The mixture was warmed to RT, covered in aluminum foil, and stirred for an additional 15 h in the dark. The reaction was then diluted with 2.0 mL saturated $Na_2S_2O_4$ aqueous solution before further dilution with water (150 mL). The organic layer was separated and the aqueous layer was back extracted with $CH_2Cl_2$ (2×15 80 mL). The combined organic layers were dried (MgSO), filtered, and concentrated in vacuo. The crude product was purified by flash chromatography (2% EtOAc in hexanes as eluant) to afford the primary iodide 8c (14.4 gm, 96% yield) as a pale yellow oil: $^1$H NMR (400 MHz, $CDCl_3$): δ 3.64 (t, J=5.7 Hz, 2H), 3.25 (t, J=6.6 Hz, 2H), 1.96 (m, 2H), 1.96 (m, 2H), 0.87 (s, 9H), 0.05 (s, 6H); $^{13}$C NMR (67.5 MHz, $CDCl_3$) δ 62.3, 36.1, 25.9, 8.3, 3.6, -5.3; IR (neat) δ max: 2929, 2857, 1472, 1101, 835, 776 $cm^{-1}$.

3-(1-Propionyl)-4-hydroxy-6-[4-methyl-1-(tert-butyidimethylsilyloxy)-butane]-2-pyrone (5a). To a stirred solution of diisopropylamine (3.34 mL, 24 mmol) in 25 mL THF at -78° C. under argon was added n-butyl lithium (9.45 mL, 2.5M solution in hexanes, 23.6 mmol). The mixture was allowed to warm to 0° C. for 30 min, recooled to -78° C., and then treated with a solution of pyrone 5 (1.47 gm, 7.5 mmol) in 10 mL of THF. After stirring for 1.0 h at -78° C., the derived dianion was treated with iodide 8c (2.5 gm, 8.25 mmol) in 10 mL THF, followed by the addition of HMPA (4.0 mL, 23.2 mmol). The reaction mixture was allowed to stir for 30 min at -78° C., before being diluted with saturated $NH_4Cl$ aqueous solution (50 mL). The organic layer was separated, and the aqueous layer was extracted with ether (2×50 mL). The organic layers were combined and dried ($MgSO_4$), filtered, and concentrated in vacuo. The resulting crude oil was purified by flash chromatography (20% EtOAc in hexanes as eluant) to afford the pure alkylation product 5a (2.4 gm, 87% yield) as a yellow oil: $^1$H NMR (400 MHz, $CDCl_3$) δ 5.90 (s, 1H), 3.57 (t, J=6.0 Hz, 2H), 3.08 (q, J=7.3 Hz, 2H), 2.56 (m, 1H), 1.43–1.73 (m, 4H), 1.22 (d, J=7.3 Hz, 3H), 1.13 (t, 3H), 0.86 (s, 9H), 0.01 (s, 6H); $^{13}$C NMR (67.5 MHz, $CDCl_3$) δ 207.8, 180.6, 175.6, 160.6, 99.3, 62.2, 38.3, 34.8, 30.0, 29.7, 25.4, 17.8, 17.5, 7.3, -5.8; IR (neat) δ max: 2936, 2858, 1743, 1636, 1561, 1445, 1256, 1100, 1006, 835, 776, $cm^{-1}$; CIHRMS ($NH_3$ gas) calcd for $C_{19}H_{33}SiO_6$ (M+H$^+$) 369.2085.

3-(1-Propionyl)-4-hydroxy-6-(4-methyl-butan-1-ol)-2-pyrone. A solution of TBS ether 5a (1.66 gm, 4.5 mmol) in 40 mL of AcOH, THF, and water (3:1:1) was stirred at RT for 22 h. The reaction was diluted with 50 mL water, extracted with EtOAc (2×100 mL). The combined organic layers were washed with $NaHCO_3$ saturated solution (1×100 mL). The organic layer was separated, and the aqueous layer was back extracted with EtOAc (1×100 mL). The organic layer was separated, and the aqueous layer was back extracted with EtOAc (1×100 mL). The combined organic layers were dried ($MgSO_4$), filtered, and concentrated in vacuo. The crude product was purified by flash chromatography (40% EtOAC in hexanes as eluant) to afford dialcohol (1.04 gm, 91% yield) as a yellow oil: $^1$H NMR (400 MHz, $CDCl_3$) δ 5.90 (s, 1H), 3.63 (br t, 2H), 3.08 (q, J=7.3 Hz, 2H), 2.58 (m, 1H), 1.75 (m, 1 H), 1.50–1.62 (m, 3H), 1.33 (br s, 1H), 1.23 (d, J=7.3 Hz, 3H), 1.13 (t, J=7.3 Hz, 3H); $^{13}$C NMR (67.5 MHz, $CDCl_3$) δ 180.5, 175.2, 160.6, 99.3, 99.0, 61.6, 38.1, 34.7, 29.8, 29.5, 17.3, 7.1, 1.51; IR (neat) δ max: 3425, 2940,1734, 1636,1559, 1448,1063, 1014 $cm^{-1}$; CIHRMS ($NH_3$gas) calcd for $C_{13}H_{19}O_5$ (M+H$^+$) 255.1232, found: 255.1252.

3-1-Propionyl)-4-hydroxy-6(4-methyl-butanol)-2pyrone (5c). To a solution of dialcohol (483 mg, 1.9 mmol) in $CH_2Cl_2$ (20 mL) was added pyridine (845 μL, 10.45 mmol), followed with Dess-Martin periodinate reagent (2.8 mg, 6.65 mmol) in one portion. The resulting reaction mixture was stirred at RT for 2.0 h before being quenched with saturated $NaHCO_3$ aqueous solution. The reaction mixture was extracted with $CH_2Cl_2$ (2×60 mL), dried ($MgSO_4$), filtered, and concentrated in vacuo. The crude product was flash chromatographed (15% EtOAc in hexanes as eluant) to afford aldehyde 5c (426 mg, 89% yield) as yellow oil: $^1$H NMR (400 MHz, $CDCl_3$) δ 9.73 (s, 1H), 5.90 (s, 1H), 3.07 (q, J=7.3 Hz, 2H), 2.59 (m, 1H), 2.46 (t, J=7.3 Hz, 2H), 1.83–202 (m, 2H), 1.23 (d, J=7.3 Hz, 3H), 1.12 (t, J=7.3 Hz, 3H); $^{13}$C NMR (67.5 MHz, $CDCl_3$) δ 200.7, 180.7, 174.4, 160.6, 99.9, 99.5, 40.8, 37.8, 35.0, 25.9, 17.5, 7.4, 1.8; IR (neat) δ max: 3096, 2978, 1727, 1636, 1560, 1446, 1391, 1235, 1070, 1014, 832 $cm^{-1}$; CIHRMS ($NH_3$ gas) calcd for $C_{13}H_{17}O_6$ (M+H$^+$) 253.1076, found: 253.1076.

(E)(1-Propionyl)-4-hydroxy-6-(methyl 6-methyl-hex-2-enoate)2-pyrone (15a). To a solution of trimethyl phosphonoacetate (1.7 gm, 9.3 mmol) in THF (20 mL) at room temperature was added NaH (360 mg, 8.95 mmol, 60% dispension in mineral oil). The resulting reaction was stirred at RT for 15 min, before aldehyde 5c (906 mg, 3.58 mmol) in 10 mL THF was added via cannula. The reaction was allowed to stir at RT for 3.0 h before being diluted with aqueous $NH_4Cl$ solution (50 mL). The mixture was extracted with EtOAc (2×100 mL), dried ($MgSO_4$), filtered, and concentrated in vacuo. The crude product was flash chromatographed (20% EtOAc in hexanes as eluant) to afford compound 15a (904 mg, 82% yield) as a yellow oil: $^1$H NMR (400 MHz, $CDCl_3$) δ 6.79 (dt, J=6.8, 15.6 Hz, 1H), 5.83 (s, 1H), 5.70 (d, J=15.6 Hz, 1H), 3.57, (s, 3H), 2.97 (q, J=7.1 Hz, 2H), 2.49 (m,1H), 2.11 (m, 2H); 1.78 (m,1H), 1.58 (m,1H), 1.14 (d,J=6.7 Hz, 3H), 1.02 (t, J=7.1 Hz, 3H); $^{13}$C NMR (75 MHz, $CDCl_3$) δ 208.2, 180.8,174.8, 166.6, 160.8, 147.4, 121.8, 100.0, 99.6, 51.4, 38.2, 35.2, 32.1,29.5, 17.7, 7.6; IR (neat) δ max: 2980, 1726, 1637, 1560, 1438, 1279, 1206, 1045, 832 $cm^{-1}$; CIHRMS ($NH_3$ gas) calcd for $C_{16}H_{20}O_6$ (M+H$^+$) 308.1260, found: 308.1234.

EXAMPLE 8

Preparation of Compound 14b/c (E3-Methyl-hex-2-en-1-ol (13b). To a white slurry of zirconocene dichloride (11.7 g, 40 mmol) in 100 mL of $(CH_2)_2Cl_2$ was added $AlMe_3$ (40 mL, 2.0M in hexanes, 80 mmol) at 0° C., stirred for 45 min, and then warmed to RT for 1.5 h. To this lemon-yellow solution was added 1-pentyne 19a (2.72 g, 40 mmol, dissolved in 20 mL $(CH_2)_2Cl_2$ at RT. The reaction was allowed to stir for 3.0 h. The volatile components were evaporated under reduced pressure (maximum 50° C., 0.3 mm Hg, 2.5 h). The remaining orange-yellow organic residue was extracted with dry hexanes (4×30 mL), and the yellow extract was transferred to a 500 mL round-bottom flask via a cannula. To this was added n-BuLi (16 mL, 2.5M in hexanes, 40 mmol) at 0° C. This orange-yellow slurry was stirred from 0° C. to RT for 1.5 h, and then THF (70 mL) was added to dissolve the precipitate. The resulting solution (homogeneous, brown-yellow color) was cannulated to a suspension of paraformaldehyde (6.0 g, 200 mmol) in THF (100 mL) under a $N_2$ atmosphere. This orange-yellow mixture was allowed to stir at RT for 20 h before it was cooled to 0° C. (ice water bath). Ice was added to dilute the reaction, and then saturated $NH_4Cl$ (100 mL)

was added. The ice bath was removed and the reaction was acidified with 3M HCl until the reaction mixture turned clear yellow (and became lhomogeneous). At this time, the reaction pH was measured at 2–3. The organic layer was separated, and the aqueous layer was extracted with ether (2×150 mL). The organic extracts were combined and washed with a saturated NaHCO$_3$ solution (200 mL), then dried with Na$_2$SO$_4$, filtered and concentrated under reduced pressure to provide the crude allylic alcohol 13a. This material was purified by flash chromatography (20% EtOAc in hexanes as eluant) to afford alcohol 13a (3.37 g, 74% yield) as a colorless oil: $^1$H NMR (400 MHz, CDCl$_3$) δ 5.39 (t, J=7.0 Hz, 1H); 4.13 (d, 7.0 Hz, 2H); 1.97 (t, J=7.3 Hz, 2H); 1.64 (s, 3H); 1.4 2(m, 2H), 1.15(br, 1H), 0.85 (t, J=7.3 Hz, 3H); $^{13}$C NMR (67.5 MHz, CDCl$_3$) δ 139.2, 123.3, 59.0, 59.0, 41.5, 20.6, 15.9, 13.6; IR (neat) δ max: 3353, 2959, 1669, 1457, 1003 cm$^{-1}$; CIHRMS (NH$_3$ gas) calcd for C$_7$H$_{14}$O$_1$ (M$^+$) 114.1045, found: 114.1035.

(E)-3-Methyl-hept-2-en-1-ol (13b). To a white slurry solution of zirconocene dichloride (7.3 g, 25 mmol) in 60 mL (CH$_2$)$_2$Cl$_2$ was added AlMe$_3$ (25 mL, 2.0M in hexanes, 50 mmol) at 0° C, stirred for 30 min, and then warmed to RT for 1.0 h. To this lemon-yellow solution was added 1-hexyne 19b (2.05 gm, 25 mmol, dissolved in 20 mL (CH$_2$)$_2$Cl$_2$ at RT. the reaction was allowed to stir at RT for 16 h. The volatile components were evaporated under reduced pressure (maximum 50° C., 0.3 mmHg, 12 h). The remaining orange-yellow organic residue was extracted with dry hexanes (4×30 mL), and the yellow extract was transferred to a 500 mL round-bottom flask via cannula. To this was added n-BuLi (10 mL, 2.5M in hexanes, 25 mmol) at 0° C. The resulting orange-yellow slurry was stirred from 0° C. to RT for 1.5 h, and then THF (50 mL) was added to dissolve the precipitate. The resulting solution (which was homogeneous and brown-yellow in color) was cannulated to a suspension of paraformaldehyde (3.75 g, 125 mmol) in THF (50 mL) under a N$_2$ atmosphere. This orange-yellow suspension was allowed to stir at RT for 20 h before it was cooled to 0° C. (ice water bath). Ice was added to dilute the reaction, and then saturated NH$_4$Cl (100 mL) was added. The ice bath was removed and the reaction was further acidified with 3 M HCl until the reaction turned to a clear yellow (homogeneous) solution. At this time, the reaction pH was measured as 2–3. The organic layer was separated, and the aqueous layer was extracted with ether (2×150 mL). The organic extracts were combined and washed with a saturated solution NaHCO$_3$ (200 mL), then dried with Na$_2$SO$_4$, filtered and concentrated under reduced pressure to provide crude allylic alcohol 13b. The crude product was purified by flash chromatography (20% EtOAc in hexanes as eluant) to afford alcohol 13b. (2.46 g, 77% yield) as a colorless oil: $^1$H NMR (400 MHz, CDCl$_3$) δ 5.37 (t, J=7.1 Hz,1H), 4.11 (d, J=7.1 Hz, 2H), 1.98 (t, J=7.5 Hz, 2H), 1.64 (s, 3H), 1.37 (m, 2H), 1.28 (m, 2H), 0,87 (t,J=7.3 Hz, 3H); $^{13}$C NMR (67.5 MHz, CDCl$_3$) δ 139.9, 123.1, 59.2, 39.2, 29.8, 22.3, 16.1, 13.9; IR (neat) δ max: 3330, 2958, 2930, 1670, 1467, 1000 cm$^{-1}$; CIHRMS (NH$_3$ gas) calcd for C$_8$H$_{16}$O$_1$ (M+) 128.1201, found: 128.1199.

(E)3-Methyl-hex-2-en-1-al (14b). To a suspension solution of alcohol 13b (892 mg, 7.82 mmol), 4 Å molecular sieves (4.0 g, activated), and NMO (1.83 g, 15.64 mmol) in CH$_2$Cl$_2$ (12 mL) at 0° C., was added TPAP (165 mg,0.47 mmol) in one-portion. The resulting dark reaction mixture was allowed to stir at 0° C. for 30 min, before it was diluted with CH$_2$Cl$_2$ (20 mL), and then filtrated through a short pad of silica gel. The eluent was concentrated in vacuo to afford aldehyde 14b (823 mg, 94% yield) as a viscous, colorless oil. This unstable aldehyde was sufficiently pure, and used immediately without further purification: $^1$H NMR (400 MHz, CDCl$_3$) δ 9.98 (d, J=8.2 Hz, 1H), 5.85 (d, J=8.2 Hz, 1H), 2.17 (t, J=7.3 Hz, 2H), 2,14 (s, 3H), 1.52 (m, 2H), 0.91 (t, J=7.3 Hz, 3H); $^{13}$C NMR (67.5 MHz, CDCl$_3$) δ 191.7, 164.5, 127.8, 43.0, 20.7, 17.8, 14.0; IR (neat) δ max: 2961, 2932, 2870, 1678, 1458,1190, 1131 cm$^{-1}$.

(E)-3-Methyl-hept-2-en-1-al (14c). To a suspension solution of alcohol 13b (739 mg, 5.7 mmol), 4 Å molecular sieves (2.9 g, activated), and NMO (1.33 g, 11.4 mmol) in CH$_2$Cl$_2$ (12 mL) at 0° C., was added TPAP (120 mg,0.34 mmol) in one-portion. The resulting dark reaction mixture was allowed to stir at 0° C. for 30 min, before being diluted with CH$_2$Cl$_2$ (20 mL), and then filtered through a short pad of silica gel. The filtrate was concentrated in vacuo to afford aldehyde 14c (704 mg, 98% yield) as a colorless oil. The aldehyde is sufficiently pure for immediate use without further purification: $^1$H NMR (400 MHz, CDCl$_3$) δ 9.94 (d, J=8.1 Hz, 1H), 5.82 (d, J=8.1 Hz, 1H), 2.16 (t,J=7.6 Hz, 2H), 2.11 (s, 3H), 1.44 (m, 2H), 1.28 (m, 2H), 0.87 (t, J=7.3 Hz, 3H); $^{13}$C NMR (75 MHz, CDCl$_3$) δ 191.3, 164.5, 127.2, 40.3, 29.2, 22.3, 17.4, 13.8; IR (neat) δ max: 2959, 2933, 2863, 1676, 1467, 1195, 1131 cm$^{-1}$.

EXAMPLE 8

Preparation of Myxopyronin A/B

3-[(E,E)-2,5-Dimethyl-2,4-octadienoyl]-4-hydroxy-6 (methyl 6 methyl-hex-2-enoate)2-pyron (17c). Compound 15a (58 mg, 0.188 mmol) was dissolved in CH$_2$Cl$_2$ (2.5 mL) and stirred at −78 ° C. under argon atmosphere. To this yellow solution was added freshly distilled TiCl$_4$ (82 μl, 0.75 mmol), the reaction turned to an orange-yellow slurry mixture immediately. After stirring for 45 min at −78° C., DIPEA (144 μL, 0.83 mmol) was added, and the reaction became a red-dark reaction mixture. This reaction mixture was allowed to stir at −78° C. for 4.0 h, then aldehyde 14b (84 mg, 0.75 mmol) dissolved in 1.0 mL CH$_2$Cl$_2$ was added via a cannula. This dark red reaction mixture was stirred at −78° C. for 50 h and then 0° C. for 5–10 min, before it was quenched with distilled water. The reaction was extracted with CH$_2$Cl$_2$ (3×20 mL), dried (Na$_2$SO$_4$), and concentrated in vacuo. The crude product was flash chromatographed (20% EtOAc in hexanes as eluant) to provide diene 17c (44 mg, 58% yield) as a sticky yellow oil: $^1$H NMR (400 MHz, CDCl$_3$): δ 6.97 (d, J=11.4 Hz, 1H), 6,89 (dt, J=6.5, 15.3 Hz, 1H), 6.13 (d, J=11.4 Hz, 1H), 5.92 (s, 1H); 5.83 (d, J=15.3 Hz, 1H), 3.70 (s, 3H), 2.58 (m, 1H), 2.21 (m, 2H), 2.13 (t, J=7.3 Hz, 2H), 1.98 (s, 3H), 1.90 (m, 1H), 1.82 (s, 3H), 1.66 (m, 1H), 1.48 (m, 2H), 1.24 (d, J=7.3 Hz, 3H), 0.89 (t, J =7.3 Hz, 3H). $^{13}$C NMR (75 MHz, CDCl$_3$): δ 201.6, 180.7, 174.7, 166.7, 160.3, 149.1, 147.5, 133.6, 132.9, 121.9, 120.6, 100.0, 99.1, 51.5, 42.8, 38.2, 32.2,29.6, 21.0, 17.7,17.2,13.8,13.5; IR (neat) δ max: 2958, 1726, 1637, 1547, 1436, 1383, 1329, 1266, 1205, 1044, cm$^{-1}$; CIHRMS (NH$_3$ gas) calcd for C$_{23}$H$_{31}$O$_6$ (M=H$^+$) 403.2120, found: 403.2108.

3-[(E,E)-2,5-Dimethyl-2,4-nonadienoyl]-4-hydroxy-6-(methyl 6-methyl-hex-2-enoate)-2-pyrone (17d). Compound 15a (178 mg, 0.578 mmol) was dissolved in CH$_2$Cl$_2$ (10 mL) and stirred at −78° C. under argon atmosphere. To this was added freshly distilled TiCl₄ (254 μL, 2.31 mmol); the reaction became a yellow slurry immediately. After stirring for 20 min at −78° C., DIPEA (483 μL, 2.77 mmol) was added, and the reaction mixture became dark red. After stirring at −78° C. for 3.0 h, aldehyde 14c (254 mg, 2.0 mmol) dissolved in 2.0 mL CH₂Cl₂ was added via cannula. The dark red reaction mixture was stirred at −78° C. for 48 h and then warmed to 0° C. for 5 min, before being quenched with distilled water. The reaction mixture was extracted with CH₂Cl₂ (3×20 mL). The organic layer was dried (Na₂SO₄), filtered, and concentrated in vacuo. The crude product was flash chromatographed (25% EtOAc in hexanes as eluant) to provide diene 17d (147 mg, 61% yield) as a sticky yellow oil: ¹H NMR (400 MHz, CDCl₃): δ 6.97 (d, J=11.6Hz,1H), 6.88 (dt,J=6.7,15.3Hz,1H), 6.13 (d,J=11.6Hz,1H), 5.91, (s, 1H), 5.81 (d, J=15.3 Hz,1H), 3.70 (s, 3H), 2.58 (m,1H), 2.20 (m, 2H), 2.14 (t, J=7.3 Hz, 2H), 1.98 (s, 3H), 1.88 (m, 1H), 1.82 (s, 3H), 1.66 (m, 1H), 1.45 (m, 2H), 1.30 (m 2H), 1.24 (d, J=6.7 Hz, 3H), 0.89 (t, J=7.3 Hz, 3H); ¹³C NMR (75 MHz, CDCl₃) δ 201.6, 180.7, 174.7, 166.7, 160.3, 149.4, 147.5, 133.6, 132.9, 121.9, 120.4, 100.0, 99.1, 51.5, 40.5, 38.2, 32.2., 30.0, 29.6, 22.4, 17.7, 17.3, 14.0, 13.5; IR (neat) δ max: 2932, 2872, 1726, 1636, 1546, 1436, 1383, 1329, 1268, 1206, 1175, 1045 cm⁻¹; CIHRMS (NH₃ gas) calcd for C₂₄H₃₂O₆ (M⁺) 416.2199, found: 416.2208.

3-[(E,E)-2,5-Dimethyl-2,4-octadienoyl]-4-hydroxy-6-(6methyl-hex-2-enoic acid)-2-pyrone (21a). To a stirred solution of 17c (60 mg, 0.15 mmol) in THF (8.0 mL) was added LiOH aqueous solution (2.0 mL, 1.0M, aq., 2.0 mmol) at RT, the resulting reaction mixture (THF/H₂O=4:1) was allowed to stir at RT for 20 h before it was diluted with EtOAc (10 mL), and then quenched by saturated NH₄Cl solution (10 mL). The reaction mixture was acidified to pH 2 by slow addition of 5% HCl. The solution was extracted with EtOAc (3×15 mL), dried (Na₂SO₄), filtered through a short pad of silica gel, and concentrated in vacuo to afford the crude acid 21a (58 mg, 100% yield) as a yellow, sticky oil. This material was used in the subsequent reaction without further purification: ¹H NMR (400 MHz, CDCl₃): δ 7.03–6.96 (m, 2H), 6.14 (d, J=11.6 Hz, 1H), 5.92 (s, 1H), 5.82 (d, J=15.9 Hz, 1H), 2.59 (m, 1H), 2.24 (m, 2H), 2.13 (t, J=7.6 Hz, 2H), 1.98 (s, 3H), 1.89 (m, 1H), 1.82 (s, 3H), 1.68 (m, 1H), 1.48 (m, 2H), 1.30 (m 2H), 1.24 (3, J=6.7 Hz, 3H), 0.89 (t, J=7.3 Hz, 3H); ¹³C NMR (75 MHz, CDCl₃) δ 201.6, 180.7, 174.5, 171.4, 160.4, 150.2, 149.1, 133.6, 132.9, 128.3, 121.6, 120.6, 10 100.1, 9.1, 42.8, 38.2, 32.0, 29.7, 20.9, 17.7, 17.2, 13.8, 13.4; IR (neat) δ max: 2960, 1724, 1636, 1561, 1446, 1383, 1249, 973, 831 cm⁻; CIHRMS (NH₃ gas) calcd for C₂₂H₂₉O₆ (M+H⁺) 389.1964, found: 389.1968.

3-[E,E-2,5-Dimethyl-2,4-nonadienoyl]-4hydroxy-6-(6methyl-hex-2-enoic acid)-2-pyrone (21b). To a stirred solution of 17d (42 mg, 9.10 mmol) in THF (6.0 mL) was added LiOH aqueous solution (1.5 mL, 1.0M aq., 1.5 mmol) at RT, the resulting reaction mixture (THF/H₂O=4:1) was allowed to stir at RT for 35 h before it was diluted with EtOAc (10 mL) and then quenched with saturated NH₄Cl aq. (10 mL). The reaction mixture was acidified to pH 2 by slow addition of 5% HCl, and extracted with EtOAc (3×15 mL). The organic layer was dried (Na₂SO₄), filtered through a short pad of silica gel, and then concentrated in vacuo to afford the crude acid 21b (40 mg, 100% yield) as a sticky yellow oil. This material was used without further purification: ¹H NMR (270 MHz, CDCl₃): δ 7.05–6.94 (m, 2H), 6.14 (d, J=11.5 Hz, 1H), 5.92 (s, 1H), 5.81 (d, J=15.4 Hz, 1H), 2.59 (m, 1H), 2.24 (m, 2H), 2.14 (t, J=7.3 Hz, 2H), 1.97 (s, 3H), 1.89 (m,1H), 1.82 (s, 3H), 1.68 (m, 1H), 1.43 (m, 2H), 1.28 (m, 2H), 1.24 (d, J=6.8 Hz, 3 H), 0.89 (t, J=7.3 Hz, 3H); ¹³C NMR (75 MHz, CDCl₃) δ 201.6, 180.7, 174.5, 171.4, 160.4, 150.2, 149.1, 133.6, 132.9, 128.3, 121.6, 120.6, 100.1, 99.1, 42.8, 38.2, 32.0, 29.7, 20.9, 17.7, 17.2, 13.8, 13.4; IR (neat) δ max: 3434, 2960, 1724, 1636, 1561, 1446, 1383, 1249, 973, 831; IR (neat) δ max: 2931, 1697, 1637, 1544, 1439, 1383, 1249, 972, 914 831 cm⁻¹; CIHRMS (NH₃ gas) calcd for C₂₃H₃₁O₆ (M+H⁺) 403.2121, found: 403.2136.

(±)-Myxopyronin A (18). To a stirred solution of acid 21a (34 mg, 0.0876 mmol) in dry acetone (1.5 mL) was added DIPEA (37 μL, 0.21 mmol) and then ethyl chloroformate (18 μL, 0.193 mmol) at 0° C. The reaction mixture was stirred at 0° C. for 1.5 h, then NaN₃ (17 mg, 0.263 mmol, dissolved in 300 μL distilled H₂O) was added via syringe. The resulting reaction mixture was stirred at 0° C. for 45 min before being diluted with ice water (5 mL). The reaction mixture was extracted with distilled toluene (8×5 mL), dried, (MgSO₄), filtered, and concentrated in vacuo. The organic residue was taken up by dry toluene (6 mL) and refluxed for 2.5 h before fresh distilled MeOH (3.0 mL) was added to trap the isocyanate intermediate. The resulting solution was refluxed for an additional 8.0 h and then concentrated in vacuo to provide crude (±)-myxopyronin A (18) as a yellow oil. The crude material was purified by preparative reversed phase HPLC (70:30:4 MeOH/H₂O/AcOH) to provide pure (±)-myxopyronin A (18, 26 mg, 71%) as a sticky yellow oil: ¹H NMR (400 MHz, CD₃OD, 3.31 ppm) δ 7.17 (d,J=11.6 Hz,1H), 6.40 (d, J=14.0 Hz, 1H), 6.27 (d, J=11.6 Hz, 1H), 6.08 (s, 1H), 5.04 (dt, J=7.3, 14.0 Hz, 1H), 3.66 (s, 3H), 2.66 (m, 1H), 2.20 (t, J=7.3 Hz, 2H), 2.01 (m, 2H), 1.94 (s, 3H), 1.81 (s,3H), 1.76 (m,1H), 1.59 (m, 1 H), 1.53 (m, 2H), 1.25 (d, J=6.7 Hz, 3H), 0.93 (t, J=7.6 Hz, 3H); ¹³C NMR (75 MHz, CD₃OD, 49.15 ppm) δ 199.0, 174.9, 173.5, 164.8, 156.9, 151.4, 138.3, 135.2, 126.2, 122.4, 110.7, 102.5, 101.4, 52.8, 44.0, 44.0, 39.3, 35.9, 28.7, 22.2, 18.6,17.4,14.2, 12.0; IR (neat) δ max: 3313, 2931, 1717, 1681, 1636, 1537, 1439, 1381, 1247, 1052, 953 cm⁻¹; UV (methanol): max (logξ)=213, 298 nm; CIHRMS (NH₃ gas) calcd for C₂₃H₃₂N₁O₆ (M=H⁺) 418.2230, found: 418.2198.

(±)-Myxopyronin B (18a). To a stirred solution of acid 21b (22 mg, 0.0547 mmol) in dry acetone (1.0 mL) was sequentially added DIPEA (23 μL, 0.13 mmol) and ethyl chloroformate (11 μL, 0.12 mmol) at 0° C. The reaction mixture was stirred at 0° C. for 1.5 h, then NaN₃ (17 mg, 0.263 mmol, dissolved in 300 μL distilled H₂O) was added via syringe. The resulting mixture was stirred at 0° C. for 70 min before being quenched with ice water (3 mL), and extracted with distilled toluene (6×5 mL). The organic layer was dried (MgSO₄), filtered, and concentrated in vacuo. The organic residue was taken up with dry toluene (6 mL), and refluxed for 2.0 h before freshly distilled MeOH (3.0 mL) was added to trap the isocyanate intermediate. The resulting solution was further refluxed for 12 h and then concentrated in vacuo to provide crude (±)-myxopyronin B (18a) as a yellow oil. This crude material was purified by preparative reversed phase HPLC (70:30:4 MeOH/H₂O/AcOH) to provide pure (±)-myxopyronin β (18a, 15.6 mg, 66%) as a yellow sticky oil: ¹H NMR (400 MHz, CD₃OD, 3.27 ppm) δ 7.15 (d, J=11.6 Hz, 1H), 6.36 (d,J=14.0 Hz, 1H), 6.23 (d,J=11.6

Hz, 1H), 6.01 (s, 1H), 5.02 (dt,J=7.3, 14.0 Hz,1H), 3.62 (s, 3H), 2.61 (m, 1H), 2.18 (t, J=7.3 Hz, 2H), 1.97 (m, 2H), 1.90 (s, 3H), 1.78 (s, 3H), 1.72 (m, 1H), 1.55 (m, 1H), 1.49 (m, 2H), 1.31 (m, 2H), 1.21 (d, J=7.3 Hz, 3H), 0.90 (t, J=7.0 Hz. 3H); $^{13}$C NMR (75 MHz, CD$_3$OD, 49.15 ppm) δ 199.1, 175.2, 173.2, 165.0, 156.9, 151.6, 138.4, 135.2, 126.1, 122.3, 110.7, 102.6, 101.9, 52.8, 41.6, 39.2, 35.9, 31.3, 29.7, 23.6, 18.6, 17.4, 14.4, 11.9; IR (neat) max: 3315, 2931,1734, 1681, 1635, 1539, 1448, 1382, 1237, 1051, 953 cm$^{-1}$; UV (methanol): λmax (logξ)=213, 298 nm; CIHRMS (NH$_3$ gas) calcd for $C_{24}H_{34}N_1O_6$ (M+H$^+$) 432.2386, found: 432.2377.

EXAMPLE 9

In vitro transcription reactions. [α$^{32}$P] UTP-incorporated RNA was synthesized in 50 μl reaction volumes containing transcription buffer (50 mM Tris-HCl, pH 8.0, 200 mM KCl, 10 mM MgCl2, 10 mM DTT and 1.5 μM BSA), 1 μg of DNA template, 4 μM UTP containing 5 μCi of [α$^{32}$P] UTP, 400 μM each of ATP, GTP, and CTP. After incubation for 60 minutes at 25° C., the reaction is terminated with 100 μl 10% TCA, which also precipitates the newly transcribed RNA.
Microdilution Minimal Inhibitory Concentration (MIC) and
  Minimum Bactericidal Concentration (MBC) Assays The minimal inhibitory concentration (MIC) is defined as the lowest concentration of antimicrobial agent that completely inhibits growth of the organism in the microliter plate. The MIC is reported as a range between the concentration at which no growth is observed and the concentration of the dilution which immediately followed. Selected inhibitors from the RNA polymerase screen described above were tested for their ability to inhibit bacterial growth in a broth microdilution assay as follows. Mueller-Hinton broth containing 20–25 mg/L Ca2+ and 10–12.5 mg/L Mg2+ (Difco #0757-07-8) is recommended as the medium (pH 7.2 and 7.4 at room temperature) of choice by the NCCLS for rapidly growing or facultative organisms and it demonstrates good batch-to-batch reproducibility for susceptibility testing; is low in sulfonamide, trimethoprim, and tetracycline inhibitors; and yields satisfactory growth of most pathogens. Dilution of antimicrobial agents is performed in a sterile, covered 96-well microliter plate with flat bottom wells (Costar #9017), and each well contains 100 μL of both +/- antimicrobial agent. The final concentrations of the small molecule antimicrobial agents are 100, 50, 25, 12.5, 6.25, 3.12, 1.56, 0.78, 0.39, 0.20, 0.10, and 0.05 μg/mL, respectively. Different dilutions are performed for natural product extracts. They are first diluted 100-fold with Mueller-Hinton broth. The final dilutions of the natural product extracts are 200, 400, 800, 1600, 3200, 6400, 12800, 25600, 51200, 1×105, 2×105, and 4×105 -fold. A 1 % DMSO (no-drug) row is prepared in Mueller-Hinton broth as a control for 100% growth on each plate. A Mueller-Hinton broth only with no bacteria growth is also included as a negative control for each plate. Ampicillin and rifampin are used as positive controls against all bacterial strains in every experiment.

The overnight culture of a single colony is diluted in sterile Mueller-Hinton broth so that, after inoculation, each well contains approximately 5×105 CFU/mL. Within 15 minutes of preparation, 50 mL of the adjusted inoculum suspension is added to the microliter plate. Each well is diluted with an equal volume of the antimicrobial agent/control substance diluted with sterile Mueller-Hinton broth. The inoculated microliter plate is incubated at 35° C. for 16–20 hours. The turbidity of each well is determined by measuring the absorbance at 595 nm on the BioRad Model 3550-UV microplate reader. The rows containing broth only (no cells) serve as a control, and the rows containing the titration of 1% DMSO serve as a control for 100% growth. The average of the broth only controls is subtracted from the average of each duplicate. This value is subsequently normalized to the average of the DMSO controls.

The minimum bactericidal concentration (MBC) is defined as the concentration of antimicrobial agent from which no colonies grow on petri plates or in the medium. In practice, the MBC is arbitrarily defined as the concentration at which a 1000-fold reduction in colony forming units is observed with respect to the original inoculum (survival of 0.1%). The broth dilution method consists of inoculating the wells from an MIC microliter plate using a 96-well inoculation grid into a fresh microliter plate containing 100 μL Mueller-Hinton broth per well. The MBC plates are incubated at 37° C. for 16–20 hrs and the MBC values are determined.

Figure 2:
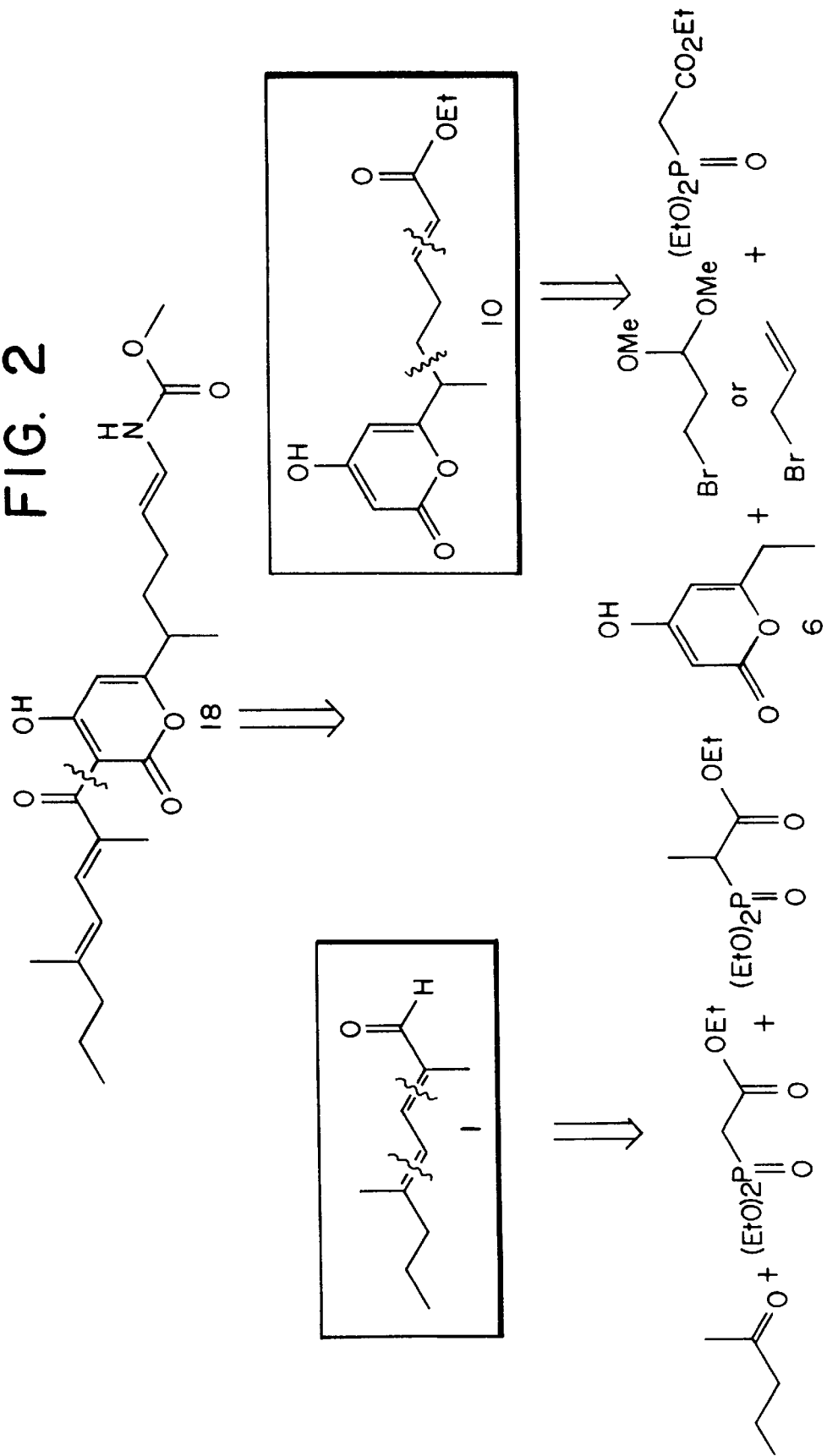
FIG. 2 illustrates a retrosynthetic analysis for the preparation of myxopyronin A.

The MIC data suggest that these compounds, like rifampicin, do not penetrate E. coli efficiently since it does inhibit the growth of a permeabilized E. coli. An attractive feature of this series is the activity against strains that are resistant to rifampicin. The MIC for rifampicin is 10 μM against susceptible strains, but inhibitory activity is greatly reduced against rifampicin resistant strains (>100 μM), illustrating the limitation of rifampicin and the need for discovery of new agents. Myxopyronins, however, are equi-active against rifampicin susceptible and rifampicin resistant S. aureus (FIG. 20(a) and (b).
Discussion The total synthesis of myxopyronin A was approached in several ways. The first is shown in the retrosynthesis provided in FIG. 2.

Attachment of the 3-position side chain was accomplished through an aldol condensation. Ester 1 is available from 2-pentanone through Wadsworth-Emmons chemistry (Wadsworth, W., Emmons, W., Org. Synth., 1965, 45, 44) and commercially available triethylphosphonates (FIG. 3). The anion of triethyl phosphonacetate is created by stirring with NaH in THF, and is condensed with 2-pentanone to create unsaturated ester 16. The ester 16 is reduced with DIBAL to the alcohol and then oxidized to the aldehyde 14 with DDQ. Compound 1 is produced by going through another cycle of Wadsworth-Emmons chemistry, DIBAL reduction and DDQ oxidation. Intermediate 13 can also be made using lithium dimethyl cuprate chemistry (Sum and Weiler, Can. J. Chem., 1979, 57, 1431), which procedure produces 13 in a higher E/Z ratio.

The other half of the molecule containing the 6-substituted pyrone is dissected in the following manner. This scheme requires a pyrone functionalized at the 6-position (Douglas, J., Money, T., Can. J. Chem., 1968, 46, 695) and commercially available reagents shown in FIG. 2. The three necessary segments can be joined by an additional Wadsworth-Emmons olefination and a simple alkylation. The terminal methyl carbamate can then be introduced by the use of a modified Curtius rearrangement. Overman, L., Taylor, G., Petty, C., Jessup, P., J. Org. Chem., 1978, 43, 2164.

Two different pathways are provided for the synthesis of compound 10. The first pathway is based on the known alkylation of the commercially available compound 3 at the 7-postion using n-BuLi and an alkyl halide. Groutas, W., Stanga, M., Brubaker, M., Huang, T., Moi, M., Carroll, R., J. Med. Chem., 1985, 28, 1106. (see FIG. 4) A model pyrone containing an ethyl group was alkylated at the 7-position in a similar manner by constructing the 6-position side chain after the desired methyl group (C-8) was already in place at C-7. (The synthetic approach used to synthesize the 6-ethyl pyrone was developed by Cook and co-workers. Cook, L., Ternai, B., Ghosh, P., *J. Med. Chem.*, 1987, 30, 1017.) The present invention provides a means of installing alkyl chains of varying sizes at the 6-position by dimerization of various ethyl malonates and subsequent deacylation of the 3-position (FIGS. 5 and 15). Thereby, pyrone 6 is prepared where R is ethyl.

Pyrone 6 is then alkylated with 3-bromopropionaldehyde dimethyl acetal and the 4-hydroxyl group protected as its SEM ether (FIG. 6). The dimethyl acetal is removed with dilute $H_2SO_4$. The Wadsworth-Emmons reaction (Wadsworth, W., Emmons, W., *Org. Synth.*, 1965, 45, 44) introduces the unsaturated ester, and the SEM group is removed with TBAF to produce key intermediate 10. The 3-position side chain is introduced by use of an aldol reaction. The ester on the 6-position side chain is hydrolyzed, and a Curtius rearrangement installs a vinyl carbamate moiety to complete the synthesis of myxopyronin A.

In a preferred embodiment, the present invention provides an improved route to intermediate 10. Allyl bromide alkylates pyrone 6 in a higher yield (FIG. 7). This modification combined with the use of dilute $H_2SO_4$ in place of TBAF to remove the SEM group substantially increases the overall yield of 10.

FIG. 8 schematically demonstrates the completion of the myxopyronin A synthesis from key intermediate 10. Aldol condensation with 1 to produce 13 is followed by oxidation with any reagent effective for oxidizing alcohols at allylic or benzylic positions, including DDQ, $MnO_2$, $K_2CrO_7$, etc., to afford ketone 17. Conversion of the ethyl ester to the acid is effected by saponification with LiOH. Finally, installation of the vinyl carbamate is effected by modified Curtius conditions.

In addition, the present invention provides an alternate pathway for the total synthesis of myxopyronin A. Formation of the bond between C-3 and C-15 has proven to be a difficult synthetic step. A study of alternative ways of appending the 3-position side chain demonstrated that attachment of a portion of the 3-position alkyl chain is effectively performed by acylation of the pyrone. This process is based on acylation of 6-alkyl-4-hydroxy-2-pyrones by acyl chlorides. Cook, L., Ternai, B., Ghosh, P., *J. Med. Chem.*, 1987, 30, 1017. However, acylation of pyrone 10 with acyl chloride 19 using conditions set forth by Cook (FIG. 9) did not provide the expected product: no evidence of the double bonds were observed by NMR; only compound 10 was recovered.

Acylation of pyrones is successful when acid chlorides with saturated alkyl chains are used. A retrosynthetic analysis of the preparation of myxopyronin A taking advantage of this reaction is shown, in FIG. 10. Pyrone 10 was synthesized as shown in FIGS. 5–7. At this point, the pyrone is acylated with propionyl chloride. The rest of the 6-position side chain is then attached using a base-catalyzed aldol reaction with aldehyde 14, an intermediate in the synthesis of 1 (FIG. 3) and the 3-propionyl pyrone 15. The synthesis is completed with a Curtius rearrangement as illustrated in FIG. 8.

The alternate route works effectively as disclosed herein. Pyrone intermediate 10 is acylated with propionyl chloride in TFA to give compound 15. An aldol reaction using LDA in THF condenses aldehyde 14 with 15. Subsequent treatment with MsCl and DBU gives the desired diene in the side chain and yields intermediate 17.

Analogs of Myxopyronins

As will be apparent to one of skill in the art, various isomers (including stereoisomers), analogs, and derivatives of the pyronins are made accessible by the subject invention by appropriate modification. For example, the total synthesis of myxopyronin B is easily carried out by simple modification of the pathway shown in FIG. 3, i.e., by substituting 2-hexanone for 2-pentanone at the beginning of the synthesis. As disclosed herein, the synthetic pathways provide a mixture of enantiomers which can be prepared in purified form by any of a variety of methods well known in the art, including but not limited to chiral HPLC, resolution of one of the intermediates set forth herein, or separation of a diastereomeric derivative. In addition, the routes may be modified by those of ordinary skill in the art to provide derivatives from the isocyanate intermediate other than carbamates. For example, instead of reacting with an alcohol, reaction with ammonia or an alkylamine would lead to a substituted urea analog. Satchell, *Chem. Soc. Rev.*, 1975, 4, 231. Also, hydrolysis generates a primary amine myxopyronin analog.

Convergent Synthesis of Myxopyronin A

Pyrones have been used to elicit a biological effect in a few instances but in none of them have they been used as an antibacterial agent. 2H-Pyran-2,6(3H)-dione derivatives are reported to be active at reasonable doses in a passive cutaneous anaphylaxis model in rats when administered by either the intravenous or oral route. Snader, K. M. et al., *J. Med. Chem.*, 1979, 22, 706; Chahrin, L. W., Snader, K. M., Williams, C. R., 2H-Pyran-2,6(3H)-dionederivate, German Patent 25 33 843. In a second case, simple 3-(1-oxoalkyl)-4-hydroxy-6-alkyl-2-pyrones were found to be effective in vitro in the inhibition of human sputum elastase. Cook, L., Ternai, B., Ghosh, P., *J. Med. Chem.*, 1987, 30, 1017. Lastly, a series of coumarin derivatives were found to be effective inhibitors of HIV protease in both enzymatic assays and cell culture (FIG. 1(*b*)). Skulnick, H. I., et al., *J. Med. Chem.*, 1995, 38, 4968. No synthetic investigations of pyronin antibacterials have been reported in the literature. The total synthesis of myxopyronin A was approached in a highly convergent manner. The retrosynthesis of myxopyronin A is shown in FIG. 11.

Preparation of compound 14 (FIG. 12(*a*)) was started from commercially available 1-pentyne. Regioselective and ster-eospecific carboalumination of 1-pentyne in the presence of 2.0 equiv of $AlMe_3$ and 1.0 equiv of $Cp_2ZrCl_2$ (Cp=η-$C_5H_5$) afforded the organoalane species, which was treated with 1.0 equiv of $^n$-BuLi, and quenched with paraformaldehyde to give geometrically pure (E) allylic alcohol 13a with 74% yield. Swern oxidation of alcohol 13a cleanly generated versatile aldehyde 14, which is not very stable and used immediately after flash chromatography.

A synthetic approach to pyrone 5 (R=Et) (FIG. 12(*b*)) was based on a known procedure reported by Cook and co-workers (supra). Commercially available ethyl propionyl-acetate was hydrolyzed under basic conditions (1.5M aqueous NaOH) to provide acid 4a (76% yield), which was dimerized, in the presence of carbonyldiimidazole, to afford pyrone 5 (R=Et) in 98% yield. This sequence of reactions easily provided a quantitative amount of pyrone 5 (R=Et), which is the core structure in the myxopyronin A structure.

Preparation of compound 8b (FIG. 12(*c*)) is straight forward. Monoprotection of 1,3-propane diol was achieved by using 1.0 equiv of NaH and 1.0 equiv of TBSCl, and it cleanly generated alcohol 8a in 98% isolated yield. Iodination of alcohol 8a under the condition of $I_2$/$PPh_3$/imidazole provided iodide 8b as a single product with 96% yield.

Subsequent research has led to an improved synthetic approach to the intermediate 15 (FIG. 13(a)). Pyrone 5 (R=Et) was lithiated (3.2 equiv of LDA) at −78° C., the derived anion was treated with iodide 8b to afford compound 5a as a single alkylated product in 80–87% isolated yield. Compound 5a was deprotonated (AcOH/THF/$H_2O$, 2:2:1 mixture solution) at RT to provide alcohol 5b (91 % yield), which was oxidized in the presence of the Dess-Martin periodinate reagent to yield aldehyde 5c. Wadsworth-Emmons homologation of aldehyde 5c (triethyl phosphonoacetate, NaH, $C_6H_6$) cleanly generated α,β-unsaturated ester 15 as a single isomer with a 89% yield. FIG. 13(b) schematically demonstrates the completion of the myxopyronin A synthesis from key intermediate 15.

Aldol condensation of ethyl ketone 15 with aldehyde 14 in the presence of $TiCl_4$ was investigated. Titanium enolate was generated at −78° C. by the treatment of ethyl ketone 15 with 4.0 equiv of $TiCl_4$ and 4.4 equiv of $Et_3N$. The derived (Z)-enolate was condensed with an excess of freshly prepared aldehyde 14 to produce diol 14a in 71.3% isolated yield. Treatment of diol 14a with methane sulfonyl chloride, followed by elimination mediated by DBU, furnished the trisubstituted diene 17 in a 72% yield. Conversion of 17 to the α,β-unsaturated acid 17a was accomplished with LiOH. Finally, installation of the vinyl carbamate functional group was effected through modified Curtius condition. Acid 17a was combined with diphenylphosphoryl azide ($PhO_2P(O)N_3$) and $Et_3N$ and refluxed in $C_6H_6$ for 9.0 h. The derived azide intermediate was treated with anhydrous MeOH and was refluxed for another 6.0 h to produce (±)myxopyronin A, compound 18.

Myxopyronin A Synthesis Aldolization of an Acyl Pyrone

Acylation of pyrones at the 3-position is successful when the acid chlorides of short, saturated alkyl chains are used. Douglas, J., Money, T., Can. *J. Chem.*, 1968, 46, 695. Acylation of 10 with propionyl chloride is followed by a base-catalyzed aldol with the appropriate aldehyde to attach the rest of the native side-chain. The necessary aldehyde 14 (FIG. 14) is generated by way of the ester 16. (Sum, F. W., Weiler, L., Can. *J. Chem.*, 1979, 57, 431) Reaction of ethyl butyrylacetate with diethyl chlorophosphite and $LiMe_2Cu$ gave predominantly the E, isomer of 16 after distillation. DIBAL reduction to the alcohol followed by Swern oxidation produced the aldehyde 14.

With aldehyde 14 in hand, the route shown in FIG. 11 was used to complete the synthesis of myxopyronin A. Pyrone intermediate 10 is acylated with propionyl chloride in TFA to give compound 15. The overall conversion is efficient since unreacted starting material can be recovered by chromatography. An aldol reaction between the pure regioisomer of 14 and 15 was performed using LDA in THF. The crude alcohol was converted to the mesylate and then eliminated using DBU. This yielded the desired diene 17.

To complete the synthesis, 17 was saponified to the acid using LiOH. A modified Curtius sequence (Overman, L., Taylor, G., Petty, C., Jessup, P., *J. Org. Chem.*, 1978, 43, 2164) was then used to install the unusual vinyl carbamate moiety and thereby afford the desired myxopyronin A. The identity of the product was confirmed by comparison of spectral data for the synthetic product with that of an authentic sample of the natural product. Resolution of the enantiomers generated at C-7 may be achieved by means of chiral HPLC.

Synthesis of Myxopyronin A and B

The absolute stereochemistry of myxopyronin A and B (Kohl, W., et al., *Liebigs Ann. Chem.* 1983, 1656–1667; Kohl, W., et al., *Liebigs Ann. Chem.* 1984, 1088–1093; Jansen, R., et al., *Liebigs Ann. Chem.* 1985, 822–836) has been determined by careful degradative and spectroscopic methods and was assigned as the (R)-configuration[1] (FIG. 16). Riechenbach determined those molecules to be broad spectrum antibiotics and selective inhibitors of bacterial DNA-dependent RNA polymerase. Irschik, H., et al., *J. Antibiot.* 1983, 36, 1651–1658. The broad spectrum of activity and selectivity for bacterial RNA polymerase over the human polymerase established the myxopyronins as promising candidates for development as antibacterial agents. The exhibition of activity against rifampicin or streptolydigin resistant bacteria by the myxopyronins suggest that these agents target a region of RNA polymerase distinct from the one by rifampicin. No prior synthetic methods have been reported concerning this class of natural products. The present convergent synthesis makes use of a 3-propionyl-4hydroxy-α-pyrone as the central building block from which both side chains are introduced. An alkylation strategy was used for the installation of the lower side chain followed by a titanium(IV) promoted aldol condensation introducing the (E,E)-dienone of the upper side chain. A retrosynthetic analysis of the myxopyronins is illustrated in FIG. 16 with the first disconnection removing the terminal unsaturated carbamate. This detachment produced the advanced intermediate 21 bearing an unsaturated carboxylate functionality. The second disconnection produced the aldol synthons in the form of the pyrone 15a and the unsaturated aldehydes. Further disconnection of 15a produced the starting 3-propionyl-4-hydroxy-α-pyrone 5. (Pyrone 5 was prepared from commercial available ethyl propionate see: Cook, L., et al., *J. Med. Chem.* 1987, 30, 1017–1022.)

Preparation of the O1- C12 Fragment. The synthesis of this material relied on a selective alkylation of the C6 ethyl group of pyrone 5 (FIG. 17). In the presence of LDA (3.2 equiv), the regioselective alkylation with primary iodide 8c proceeds through the trianion intermediate to give the alkylated pyrone 5a in good yield. Intermediate 5a was deprotected under mild acidic conditions to afford the corresponding primary alcohol in 90% yield. (Alkyl iodide 8c was prepared from 1,3-propane diol by a two step reaction sequence: (i) selective protection with TBSCI (1.0 equiv), NaH (1.0 equiv), 98% yield; (ii) $I_2$, $PPh_3$, imidazole, 96% yield; satisfactory spectroscopic data ($^1H$ and $^{13}C$-NMR, IR, CIMS and CIHRMS) were obtained for all new compounds.) Oxidation of the primary hydroxyl with freshly prepared Dess-Martin reagent (2.0 equiv, 0° C., 2 h) gave aldehyde 5c. (Dess, D. B.; Martin, J. C. *J. Org. Chem.* 1983, 48, 4155–4156; Dess, D. B.; Martin, J. C. *J. Am. Chem. Soc.* 1991, 113, 7277–7287. Improved procedures for the preparation of DMP are found in Ireland, R.E.; Liu, L. *J. Org. Chem.* 1993, 58, 2899, and Meyer, S. D.; Schreiber, S. L. *J. Org. Chem.* 1994, 59, 7549–7552.) Subsequent Horner-Emmons-Wadsworth homologation using trimethyl phosphonoacetate (2.2 equiv NaH, 2.2 equiv THF, rt) afforded the α,β-unsaturated ester 15a with a E:Z isomer ratio greater than 20:1, after silica gel chromatography to provide geometrically pure 15a in 82% yield. This sequence completed the preparation of the O1-C12 fragment now set for the subsequent aldol condensation for the introduction of the C15–C24 and C25 side chains of 10 myxopyronin A and B.

Synthesis of the α,β-Unsaturated Aldehydes 14b and 14c. The synthesis of these subunits relied on the Negishi's carbon alumination of the terminal alkynes 19a and 19b (FIG. 18). Negishi, E., et al., *J. Am. Chem. Soc.* 1996, 118, 9577–9588; Okukado, N.; Negishi, E. *Tetrahedron Lett.* 1978, 27, 2357–2360. Treatment of alkyne 19a/b with zirconocene dichloride (1.0 equiv) in the presence of AlMe$_3$ (2.0 equiv) afforded the (E)-trisubstituted vinyl aluminate 20, which was then directly converted to the more reactive aluminate complex by addition of n-BuLi (1.0 equiv, THF). This intermediate was trapped with excess paraformaldehyde affording the (E)-trisubstituted allylic alcohol 13b/c in good overall yield. Oxidation of this material with TPAP (0.06 equiv; tetrapropylammonium perruthenate; Ley, S., et al., *Synthesis* 1994, 639–666; Griffith, w.; Ley, S. *Aldrichimica Acta* 1990, 23, 13–19) with NMO (N-methylmorpholine oxide) as the secondary oxidant (2.0 equiv) afforded the corresponding aldehydes 14b and 14c, respectively. These procedures completed the preparation of the volatile and sensitive aldehydes which were used in the subsequent aldol condensations for installing the C15–C24/25 upper side chain of the myxopyronins.

Titanium (IV) Promoted Aldol Condensation and Completion of the Syntheses. The introduction of the upperside chains of myxopyronin A and B was carried out utilizing a Ti(IV) tetrachloride promoted aldol condensation between the ethyl ketone of 15a and aldehydes 14b and 14c (FIG. 19). The titanium enolate was generated at −78° C. by treatment of ethyl ketone 15a with TiCl$_4$ (4.0 equiv) and DIPEA (4.8 equiv). The derived enolate was condensed with freshly prepared aldehyde 14b/c at −78° C. for 48–56 h to directly afford after in situ dehydration the respective (E, E)-dienones 17c and 17d. With both side chains installed onto the a-pyrone core, completion of the individual syntheses required the conversion of the α,β-unsaturated methyl ester to the methylcarbamate. This was initiated by a LiOH (10 equiv, THF/H$_2$O 4:1, 15 h) promoted hydrolysis of the methylesters which afforded the free carboxylic acids 17c and 17d in quantitative yield. The vinyl carbamate was introduced by a modified Curtius rearrangement (Overman, L., et al., *J. Org. Chem.* 1978, 43, 21 642167) employing ethylchloroformate and NaN$_3$. This sequence completed the assembly of the lower side and achieved the synthesis of (±)-myxopyronin A and B.

Biological Evaluation of (±)-Myxopyronin A & B. The biological activities of the myxypyronins were evaluated with an in vitro transcription assay using *E. coli* RNA polymerase (FIG. 20a,b). The myxopyronins A/B were isolated as a mixture of natural products containing a 9:1 ratio of A and B. The synthetic (±)-myxopyronin A (FIG. 20a) is equally potent as the natural product mixtures. As a validation of the in vitro transcription assay, a known transcription inhibitor, rifampicin, was included in the assay. As a comparison, the synthetic myxypyronin A and B were tested against *E. coli* RNA polymerase separately and myxopyrorin B is shown to be a more potent molecule than A (FIG. 20b).

Table II summarizes in vitro IC$_{50}$ and MIC values obtained from the cell-based evaluation of the myxopyronins using both gram-positive and gram-negative bacteria. The data show that myxopyronins have in vivo cell-based activities against rifampicin-resistant bacteria. In complement to the in vitro transcription activities, myxopyronin B is also shown to have up to 30 fold more potent cell-based activities than A (Table II).

TABLE II

In vitro transcription assays (IC$_{50}$) and MIC values of the synthetic myxopyronins and the mixture of natural products

| Compound | In vitro transcription (*E.coli* RNAP) IC$_{50}$ (µg/mL) | MIC (µg/mL) *E. coli* | MIC (µg/mL) *E. coli*\* | MIC (µg/mL) *S. aureus* | MIC (µg/mL) *S. aureus*\* |
|---|---|---|---|---|---|
| (R)-Myxo A/B (natural mixture) | 8 | 200 | 5 | 4 | 5 |
| (±)-Myxo B | 5 | >30 | 2 | 0.5 | 0.5 |
| (±)-Myxo A | 20 | >30 | 4–8 | 15 | 8 |

\* Mutant strain that has permeabilized cell wall.

The present invention therefore provides a highly convergent synthetic pathways to myxopyronin A and B, as well as analogs and derivatives thereof. Biological evaluation of these agents against RNA polymerase for a variety of bacteria including mammalian culture cells demonstrates their considerable utility as antibacterial agents.

What is claimed is:

1. A process of preparing a myxopyronin having the structure:

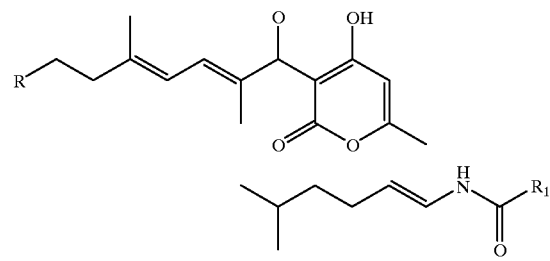

wherein R is C$_{1-3}$ alkyl, and wherein R$_1$ is C$_{1-9}$ alkoxy; which comprises;

(a) condensing an aldehyde having the structure:

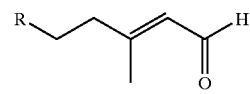

with a pyrone having the structure:

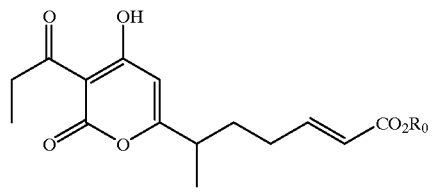

wherein $R_0$ is $C_{1-9}$ alkyl, to form a pyrone ketone having the structure:

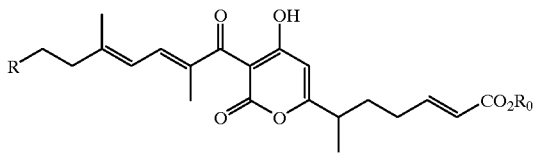

and (b) saponifying the pyrone ketone formed in step
   (a) to form a pyrone acid; and
(c) activating the pyrone acid to form a pyrone anhydride;
   (ii) reacting the pyrone anhydride formed in step (i) with an azide salt to form a pyrone acyl azide; and
   (iii) reacting the pyrone acyl azide formed in steD (ii) with an alcohol $R_1OH$ to form the myxopyronin.

2. The process of claim 1 wherein the pyrone is condensed with the aldehyde in the presence of a titanium(IV) reagent.

3. The process of claim 1 wherein the pyrone ketone is saponified in the presence of a hydroxide salt.

4. The process of claim 3 wherein the hydroxide salt is LiOH, NaOH, KOH, ammonium hydroxide, tetramethylammonium hydroxide, tetraethyl-ammoniuum hydroxide, tetra-n-propylammonium hydroxide or tetra-n-butylammonium hydroxide.

5. The process of claim 1 wherein the alcohol $R_1OH$ is methanol.

6. The process of claim 1 wherein in step (c)(i) the pyrone is reacted with alkyl haloformate, and subsequently with an azide salt.

7. The process of claim 6 wherein the alkylhaloformate is methyl or ethyl chloroformate, and the azide salt is $LiN_3$ or $NaN_3$.

8. The process of claim 1 wherein R is methyl.

9. The process of claim 1 wherein R is ethyl.

10. A process of preparing an unsaturated aldehyde having the structure:

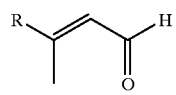

wherein R is $C_{1-9}$ alkyl;

which comprises:

(a) reacting an acetylene having the structure:

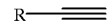

with a first organometaliic reagent to form a first intermediate;

(b) reacting the first intermediate with a second organometallic reagent so as to form a second intermediate comprising a reactive (E)-trisubstituted vinylaluminate;

(c) condensing the second intermediate with paraformaldehyde to form an allylic alcohol having the structure:

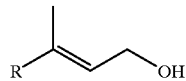

and (d) oxidizing the allylic alcohol formed in step (c) to form the unsaturated aldehyde.

11. The process of claim 10 wherein the first organometallic reagent comprises a zirconocene dihalide in the presence of a trialkylalane.

12. The process of claim 11 wherein the zirconocene dihalide is zirconocene dichloride and the trialane is trimethylaluminum.

13. The process of claim 10 wherein the second organometallic reagent is an alkyllithium reagent.

14. The process of claim 10 wherein the allylic alcohol is oxidized with pyridinium chlorochromate, pyridine dichloride, manganese dioxide, a Swern reagent or tetrapropylammonium perruthenate in the presence of N-methylmorpholine N-oxide.

15. A compound having the structure:

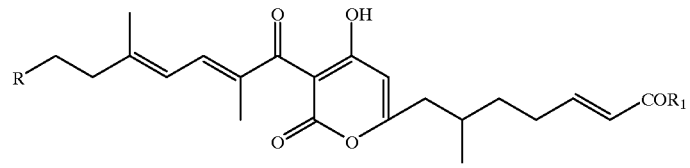

wherein R is $C_{1-3}$ alkyl, and wherein $R_1$ is H, $C_{1-9}$ alkyl, benzyl, optionally substituted phenyl, OH, $C_{1-9}$ alkoxy, $NH_2$ alkylamine, dialkylamine, or optionally substituted phenylamine.

* * * * *